(12) United States Patent
Atkins et al.

(10) Patent No.: US 12,226,567 B2
(45) Date of Patent: *Feb. 18, 2025

(54) LEAK-RESISTANT VAPORIZER DEVICE

(71) Applicant: Pax Labs, Inc., San Francisco, CA (US)

(72) Inventors: Ariel Atkins, San Francisco, CA (US); Adam Bowen, San Mateo, CA (US); Steven Christensen, Burlingame, CA (US); Nicholas Jay Hatton, Oakland, CA (US); Esteban Leon Duque, Berkeley, CA (US); James Monsees, San Francisco, CA (US)

(73) Assignee: Pax Labs, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/124,249

(22) Filed: Mar. 21, 2023

(65) Prior Publication Data

US 2023/0218836 A1     Jul. 13, 2023

Related U.S. Application Data

(63) Continuation of application No. 15/396,584, filed on Dec. 31, 2016, now Pat. No. 11,660,403.

(Continued)

(51) Int. Cl.
    *A61M 11/00*     (2006.01)
    *A24F 7/00*     (2006.01)
    (Continued)

(52) U.S. Cl.
    CPC ............... *A61M 11/00* (2013.01); *A24F 7/00* (2013.01); *A24F 40/40* (2020.01); *A24F 40/42* (2020.01); *A24F 40/44* (2020.01); *A24F 40/46* (2020.01); *A24F 40/485* (2020.01); *A61M 11/042* (2014.02); *A61M 11/044* (2014.02); *A61M 15/06* (2013.01); *A24F 40/10* (2020.01);

(Continued)

(58) Field of Classification Search
None
See application file for complete search history.

(56) References Cited

U.S. PATENT DOCUMENTS

| 1,671,185 A | 5/1928 | Flynn |
| 1,950,542 A | 3/1934 | Copell |

(Continued)

FOREIGN PATENT DOCUMENTS

| AT | 507187 A4 | 3/2010 |
| CA | 2920973 C | 9/2018 |

(Continued)

OTHER PUBLICATIONS

U.S. Appl. No. 15/396,584, filed Dec. 31, 2016, US 20180077967 A1.

(Continued)

*Primary Examiner* — Phu H Nguyen
(74) *Attorney, Agent, or Firm* — Mintz Levin Cohn Ferris Glovsky and Popeo, P.C.

(57) ABSTRACT

Vaporizer cartridges and vaporizer apparatuses, and methods for making, using and delivering vapor to a user, that are leak-resistant for use with cannabinoids. In particular, described herein are leak-resistant vaporizer cartridges and apparatuses adapted for use with oil-based vaporizable materials including *cannabis* oils.

20 Claims, 26 Drawing Sheets

Related U.S. Application Data

(60) Provisional application No. 62/398,494, filed on Sep. 22, 2016.

(51) Int. Cl.

| | |
|---|---|
| *A24F 40/10* | (2020.01) |
| *A24F 40/40* | (2020.01) |
| *A24F 40/42* | (2020.01) |
| *A24F 40/44* | (2020.01) |
| *A24F 40/46* | (2020.01) |
| *A24F 40/485* | (2020.01) |
| *A61M 11/04* | (2006.01) |
| *A61M 15/00* | (2006.01) |
| *A61M 15/06* | (2006.01) |

(52) U.S. Cl.
CPC ... *A61M 15/0021* (2014.02); *A61M 2205/121* (2013.01); *A61M 2205/123* (2013.01); *A61M 2205/8206* (2013.01)

(56) References Cited

U.S. PATENT DOCUMENTS

| | | |
|---|---|---|
| 2,900,989 A | 8/1959 | Davidson |
| 4,945,931 A | 8/1990 | Gori |
| 6,516,796 B1 | 2/2003 | Cox et al. |
| 6,637,430 B1 | 10/2003 | Voges et al. |
| 6,717,088 B2 | 4/2004 | Kawamoto et al. |
| 7,284,553 B2 | 10/2007 | Hochrainer |
| 7,802,569 B2 | 9/2010 | Yeates et al. |
| 8,109,267 B2 | 2/2012 | Villax et al. |
| 8,499,766 B1 | 8/2013 | Newton |
| 8,528,569 B1 | 9/2013 | Newton |
| 8,579,107 B2 | 11/2013 | Egued |
| 8,714,161 B2 | 5/2014 | Liu |
| 8,752,545 B2 | 6/2014 | Buchberger |
| 8,770,187 B2 | 7/2014 | Murphy |
| 8,833,364 B2 | 9/2014 | Buchberger |
| 8,899,240 B2 | 12/2014 | Mass |
| 8,948,578 B2 | 2/2015 | Buchberger |
| 9,010,335 B1 | 4/2015 | Scatterday |
| 9,078,474 B2 | 7/2015 | Thompson |
| 9,089,166 B1 | 7/2015 | Scatterday |
| 9,089,168 B2 | 7/2015 | Liu |
| 9,155,336 B2 | 10/2015 | Liu |
| 9,247,773 B2 | 2/2016 | Memari et al. |
| 9,289,014 B2 | 3/2016 | Tucker et al. |
| 9,332,787 B2 | 5/2016 | Liu |
| 9,351,522 B2 | 5/2016 | Safari |
| 9,364,025 B2 | 6/2016 | Liu |
| 9,427,022 B2 | 8/2016 | Levin et al. |
| 9,497,998 B2 | 11/2016 | Chen |
| 9,510,623 B2 | 12/2016 | Tucker et al. |
| 9,526,272 B2 | 12/2016 | Liu |
| 9,538,788 B2 | 1/2017 | Cyphert et al. |
| 9,648,908 B1 | 5/2017 | Rinehart et al. |
| 9,668,520 B2 | 6/2017 | Boldrini |
| 9,668,522 B2 | 6/2017 | Memari et al. |
| 9,681,688 B1 | 6/2017 | Rinehart et al. |
| 9,763,475 B2 | 9/2017 | Liu |
| 9,763,478 B2 | 9/2017 | Cameron et al. |
| 9,770,055 B2 | 9/2017 | Cameron et al. |
| 9,795,168 B2 | 10/2017 | Zhu |
| 9,833,021 B2 | 12/2017 | Perez et al. |
| 9,839,237 B2 | 12/2017 | Chang et al. |
| 9,844,234 B2 | 12/2017 | Thorens et al. |
| 9,861,135 B2 | 1/2018 | Chen |
| 9,877,519 B2 | 1/2018 | Xiang |
| 9,918,496 B2 | 3/2018 | Kane et al. |
| 9,943,109 B2 | 4/2018 | Chen |
| 9,955,726 B2 | 5/2018 | Brinkley et al. |
| 9,986,762 B2 | 6/2018 | Alarcon et al. |
| 9,993,025 B2 | 6/2018 | Alarcon et al. |
| 10,039,318 B2 | 8/2018 | Daryani |
| 10,058,124 B2 | 8/2018 | Monsees et al. |
| 10,058,128 B2 | 8/2018 | Cameron et al. |
| 10,070,668 B2 | 9/2018 | Li et al. |
| 10,080,387 B2 | 9/2018 | Phillips et al. |
| 10,085,481 B2 | 10/2018 | Verleur et al. |
| 10,085,484 B2 | 10/2018 | Li et al. |
| 10,085,486 B2 | 10/2018 | Cameron |
| 10,130,123 B2 | 11/2018 | Hatton et al. |
| 10,131,532 B2 | 11/2018 | Murison et al. |
| 10,143,232 B2 | 12/2018 | Talon |
| 10,159,282 B2 | 12/2018 | Monsees et al. |
| 10,206,429 B2 | 2/2019 | Davis et al. |
| 10,279,934 B2 | 5/2019 | Christensen et al. |
| 10,299,513 B2 | 5/2019 | Perez et al. |
| 10,383,368 B2 | 8/2019 | Larson |
| 10,426,199 B2 | 10/2019 | Turner et al. |
| 10,492,542 B1 | 12/2019 | Worm et al. |
| 10,792,685 B2 | 10/2020 | Tong |
| 10,863,772 B2 | 12/2020 | Borkovec et al. |
| 10,905,162 B2 | 2/2021 | Alarcon et al. |
| 11,111,127 B2 | 9/2021 | Scott et al. |
| RE49,160 E | 8/2022 | Zhou |
| 11,660,403 B2 | 5/2023 | Atkins et al. |
| 2003/0154991 A1 | 8/2003 | Fournier et al. |
| 2007/0215168 A1 | 9/2007 | Banerjee et al. |
| 2009/0255534 A1 | 10/2009 | Paterno |
| 2010/0186757 A1 | 7/2010 | Crooks et al. |
| 2010/0200008 A1 | 8/2010 | Taieb |
| 2012/0018529 A1 | 1/2012 | Gammon et al. |
| 2012/0318882 A1 | 12/2012 | Abehasera |
| 2013/0192615 A1 | 8/2013 | Tucker et al. |
| 2013/0199528 A1 | 8/2013 | Goodman et al. |
| 2013/0312742 A1 | 11/2013 | Monsees et al. |
| 2014/0041655 A1 | 2/2014 | Barron et al. |
| 2014/0041658 A1 | 2/2014 | Goodman et al. |
| 2014/0150810 A1 | 6/2014 | Hon |
| 2014/0158129 A1 | 6/2014 | Pratt, Jr. |
| 2014/0182612 A1 | 7/2014 | Chen |
| 2014/0202454 A1 | 7/2014 | Buchberger |
| 2014/0238421 A1 | 8/2014 | Shapiro |
| 2014/0261399 A1 | 9/2014 | Murphy |
| 2014/0261408 A1 | 9/2014 | DePiano et al. |
| 2014/0261487 A1 | 9/2014 | Chapman et al. |
| 2014/0290677 A1 | 10/2014 | Liu |
| 2014/0345635 A1 | 11/2014 | Rabinowitz et al. |
| 2014/0355969 A1 | 12/2014 | Stern |
| 2015/0007836 A1 | 1/2015 | Li et al. |
| 2015/0040929 A1 | 2/2015 | Hon |
| 2015/0136158 A1 | 5/2015 | Stevens et al. |
| 2015/0144147 A1 | 5/2015 | Li et al. |
| 2015/0150305 A1 | 6/2015 | Shenkal |
| 2015/0157054 A1 | 6/2015 | Liu |
| 2015/0164147 A1 | 6/2015 | Verleur et al. |
| 2015/0181941 A1 | 7/2015 | Liu |
| 2015/0184846 A1 | 7/2015 | Liu |
| 2015/0189919 A1 | 7/2015 | Liu |
| 2015/0201674 A1 | 7/2015 | Dooly et al. |
| 2015/0208729 A1 | 7/2015 | Monsees et al. |
| 2015/0216236 A1 | 8/2015 | Bless et al. |
| 2015/0223521 A1 | 8/2015 | Menting et al. |
| 2015/0223522 A1 | 8/2015 | Ampolini et al. |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0257451 A1 | 9/2015 | Brannon et al. |
| 2015/0272217 A1 | 10/2015 | Chen |
| 2015/0282530 A1 | 10/2015 | Johnson et al. |
| 2015/0289565 A1 | 10/2015 | Cadieux et al. |
| 2015/0305406 A1 | 10/2015 | Li et al. |
| 2015/0313287 A1 | 11/2015 | Verleur et al. |
| 2015/0320116 A1 | 11/2015 | Bleloch et al. |
| 2015/0327595 A1 | 11/2015 | Scatterday |
| 2015/0328415 A1 | 11/2015 | Minskoff et al. |
| 2015/0342258 A1 | 12/2015 | Chen |
| 2015/0366267 A1 | 12/2015 | Liu |

(56) References Cited

U.S. PATENT DOCUMENTS

| | | |
|---|---|---|
| 2016/0000147 A1 | 1/2016 | Li et al. |
| 2016/0000149 A1 | 1/2016 | Scatterday |
| 2016/0007655 A1 | 1/2016 | Li et al. |
| 2016/0044965 A1 | 2/2016 | Liu |
| 2016/0057811 A1 | 2/2016 | Alarcon et al. |
| 2016/0073692 A1 | 3/2016 | Alarcon et al. |
| 2016/0081394 A1 | 3/2016 | Alarcon et al. |
| 2016/0095357 A1 | 4/2016 | Burton |
| 2016/0100632 A1 | 4/2016 | Debono et al. |
| 2016/0120226 A1 | 5/2016 | Rado |
| 2016/0120227 A1 | 5/2016 | Levitz et al. |
| 2016/0128384 A1 | 5/2016 | Luciani |
| 2016/0129205 A1 | 5/2016 | Shahaf et al. |
| 2016/0135504 A1 | 5/2016 | Li et al. |
| 2016/0150823 A1 | 6/2016 | Liu |
| 2016/0150824 A1 | 6/2016 | Memari et al. |
| 2016/0157524 A1 | 6/2016 | Bowen et al. |
| 2016/0174611 A1 | 6/2016 | Monsees et al. |
| 2016/0193434 A1 | 7/2016 | Gleixner et al. |
| 2016/0198767 A1 | 7/2016 | Verleur |
| 2016/0198769 A1 | 7/2016 | Liu |
| 2016/0198770 A1 | 7/2016 | Alarcon |
| 2016/0213866 A1 | 7/2016 | Tan |
| 2016/0219934 A1 | 8/2016 | Li et al. |
| 2016/0219937 A1 | 8/2016 | Rado |
| 2016/0235120 A1 | 8/2016 | Liu |
| 2016/0235125 A1 | 8/2016 | Safari |
| 2016/0249684 A1 | 9/2016 | Liu |
| 2016/0262452 A1 | 9/2016 | Zhu |
| 2016/0262459 A1 | 9/2016 | Monsees et al. |
| 2016/0278163 A1 | 9/2016 | Chen |
| 2016/0286860 A1 | 10/2016 | Flayler |
| 2016/0286863 A1 | 10/2016 | Lin |
| 2016/0286865 A1 | 10/2016 | King et al. |
| 2016/0302487 A1 | 10/2016 | Chen |
| 2016/0309785 A1 | 10/2016 | Holtz |
| 2016/0324217 A1 | 11/2016 | Cameron |
| 2016/0325055 A1 | 11/2016 | Cameron |
| 2016/0331022 A1 | 11/2016 | Cameron |
| 2016/0331023 A1 | 11/2016 | Cameron |
| 2016/0331024 A1 | 11/2016 | Cameron |
| 2016/0331025 A1 | 11/2016 | Cameron |
| 2016/0331026 A1 | 11/2016 | Cameron |
| 2016/0331034 A1 | 11/2016 | Cameron |
| 2016/0331037 A1 | 11/2016 | Cameron |
| 2016/0332754 A1 | 11/2016 | Brown et al. |
| 2016/0334847 A1 | 11/2016 | Cameron |
| 2016/0337141 A1 | 11/2016 | Cameron |
| 2016/0337444 A1 | 11/2016 | Cameron |
| 2016/0338413 A1 | 11/2016 | Li et al. |
| 2016/0345621 A1 | 12/2016 | Li et al. |
| 2016/0356751 A1 | 12/2016 | Blackley |
| 2016/0360789 A1 | 12/2016 | Hawes et al. |
| 2016/0363570 A1 | 12/2016 | Blackley |
| 2016/0363917 A1 | 12/2016 | Blackley |
| 2016/0366936 A1 | 12/2016 | Liu |
| 2016/0366943 A1 | 12/2016 | Li et al. |
| 2016/0366945 A1 | 12/2016 | Rado |
| 2016/0366947 A1 | 12/2016 | Monsees et al. |
| 2016/0367925 A1 | 12/2016 | Blackley |
| 2016/0370335 A1 | 12/2016 | Blackley |
| 2016/0374393 A1 | 12/2016 | Chen |
| 2016/0374399 A1 | 12/2016 | Monsees et al. |
| 2017/0006922 A1 | 1/2017 | Wang et al. |
| 2017/0013885 A1 | 1/2017 | Qiu |
| 2017/0018000 A1 | 1/2017 | Cameron |
| 2017/0020188 A1 | 1/2017 | Cameron |
| 2017/0020195 A1 | 1/2017 | Cameron |
| 2017/0020196 A1 | 1/2017 | Cameron |
| 2017/0020197 A1 | 1/2017 | Cameron |
| 2017/0035110 A1 | 2/2017 | Keen |
| 2017/0042229 A1 | 2/2017 | Liu |
| 2017/0042246 A1 | 2/2017 | Lau et al. |
| 2017/0049153 A1 | 2/2017 | Guo et al. |
| 2017/0055586 A1 | 3/2017 | Liu |
| 2017/0055588 A1 | 3/2017 | Cameron |
| 2017/0071249 A1 | 3/2017 | Ampolini et al. |
| 2017/0108210 A1 | 4/2017 | Meinhart et al. |
| 2017/0112193 A1 | 4/2017 | Chen |
| 2017/0119057 A1 | 5/2017 | Liu |
| 2017/0119060 A1 | 5/2017 | Li et al. |
| 2017/0196265 A1 | 7/2017 | Liu |
| 2017/0196272 A1 | 7/2017 | Li et al. |
| 2017/0208857 A1 | 7/2017 | Branton et al. |
| 2017/0224013 A1 | 8/2017 | Huang |
| 2017/0231282 A1 | 8/2017 | Bowen et al. |
| 2017/0231286 A1 | 8/2017 | Borkovec et al. |
| 2017/0233114 A1 | 8/2017 | Christensen et al. |
| 2017/0245546 A1 | 8/2017 | Huang |
| 2017/0259170 A1 | 9/2017 | Bowen et al. |
| 2017/0347706 A1 | 12/2017 | Aoun et al. |
| 2017/0360093 A1 | 12/2017 | Fernando |
| 2018/0000157 A1 | 1/2018 | Batista et al. |
| 2018/0016040 A1 | 1/2018 | Ewing et al. |
| 2018/0022516 A1 | 1/2018 | Liu |
| 2018/0064169 A1 | 3/2018 | Biel et al. |
| 2018/0160733 A1 | 6/2018 | Leadley et al. |
| 2018/0161525 A1 | 6/2018 | Liu et al. |
| 2018/0168227 A1 | 6/2018 | Fraser et al. |
| 2023/0354907 A1 | 11/2023 | Biel et al. |

FOREIGN PATENT DOCUMENTS

| | | |
|---|---|---|
| CN | 101263935 A | 9/2008 |
| CN | 100589726 C | 2/2010 |
| CN | 201430916 Y | 3/2010 |
| CN | 201683029 U | 12/2010 |
| CN | 203538388 U | 4/2014 |
| CN | 203851804 U | 10/2014 |
| CN | 204180941 U | 3/2015 |
| CN | 204217907 U | 3/2015 |
| CN | 204426692 U | 7/2015 |
| CN | 204444246 U | 7/2015 |
| CN | 204888741 U | 12/2015 |
| CN | 105249536 A | 1/2016 |
| CN | 105614954 A | 6/2016 |
| CN | 205390306 U | 7/2016 |
| CN | 104305526 B | 8/2016 |
| CN | 205456063 U | 8/2016 |
| CN | 105962419 A | 9/2016 |
| DE | 202014001717 U1 | 5/2015 |
| DE | 202015009688 U1 | 3/2019 |
| EP | 0535695 A2 | 4/1993 |
| EP | 1093936 A1 | 4/2001 |
| EP | 2789248 A1 | 10/2014 |
| EP | 3031339 A1 | 6/2016 |
| EP | 3042579 A1 | 7/2016 |
| EP | 3143884 A2 | 3/2017 |
| EP | 3158883 A2 | 4/2017 |
| EP | 3195738 A2 | 7/2017 |
| EP | 3024344 B1 | 9/2018 |
| EP | 3313215 B1 | 6/2019 |
| EP | 3409597 B1 | 6/2019 |
| JE | P-2614731 A1 | 7/2013 |
| JP | 2002231420 A | 8/2002 |
| KR | 20110006928 U | 7/2011 |
| KR | 200461404 Y1 | 7/2012 |
| KR | 20-0462610 Y1 | 9/2012 |
| KR | 20120006582 U | 9/2012 |
| KR | 200473510 Y1 | 8/2014 |
| KR | 101541750 B1 | 8/2015 |
| KR | 101634882 B1 | 6/2016 |
| KR | 200481405 Y1 | 10/2016 |
| KR | 101774283 B1 | 9/2017 |
| KR | 101995956 B1 | 7/2019 |
| WO | WO-2006021153 A1 | 3/2006 |
| WO | WO-2007145644 A1 | 12/2007 |
| WO | WO-2009135729 A1 | 11/2009 |
| WO | WO-2010045671 A1 | 4/2010 |
| WO | WO-2010118644 A1 | 10/2010 |
| WO | WO-2012040512 A2 | 3/2012 |
| WO | WO-2012134117 A2 | 10/2012 |
| WO | WO-2012173322 A1 | 12/2012 |
| WO | WO-2012174677 A1 | 12/2012 |

(56) References Cited

FOREIGN PATENT DOCUMENTS

| | | |
|---|---|---|
| WO | WO-2013089358 A1 | 6/2013 |
| WO | WO-2013089551 A1 | 6/2013 |
| WO | WO-2013110209 A1 | 8/2013 |
| WO | WO-2014020953 A1 | 2/2014 |
| WO | WO-2014071747 A1 | 5/2014 |
| WO | WO-2014101734 A1 | 7/2014 |
| WO | WO-2014185937 A1 | 11/2014 |
| WO | WO-2015070398 A1 | 5/2015 |
| WO | WO-2015070405 A1 | 5/2015 |
| WO | WO-2015100361 A1 | 7/2015 |
| WO | WO-2015106440 A1 | 7/2015 |
| WO | WO-2015107552 A1 | 7/2015 |
| WO | WO-2015117703 A1 | 8/2015 |
| WO | WO-2015120589 A1 | 8/2015 |
| WO | WO-2015128665 A1 | 9/2015 |
| WO | WO-2015144057 A1 | 10/2015 |
| WO | WO-2015149311 A1 | 10/2015 |
| WO | WO-2015149403 A1 | 10/2015 |
| WO | WO-2015154309 A1 | 10/2015 |
| WO | WO-2015157900 A1 | 10/2015 |
| WO | WO-2015161407 A1 | 10/2015 |
| WO | WO-2015161553 A1 | 10/2015 |
| WO | WO-2015161557 A1 | 10/2015 |
| WO | WO-2015165081 A1 | 11/2015 |
| WO | WO-2015165083 A1 | 11/2015 |
| WO | WO-2015165105 A1 | 11/2015 |
| WO | WO-2015172331 A1 | 11/2015 |
| WO | WO-2015172368 A1 | 11/2015 |
| WO | WO-2015176230 A1 | 11/2015 |
| WO | WO-2015176580 A1 | 11/2015 |
| WO | WO-2015180061 A1 | 12/2015 |
| WO | WO-2015180088 A1 | 12/2015 |
| WO | WO-2015184747 A1 | 12/2015 |
| WO | WO-2015188295 A1 | 12/2015 |
| WO | WO-2015192377 A1 | 12/2015 |
| WO | WO-2015196463 A1 | 12/2015 |
| WO | WO-2016000206 A1 | 1/2016 |
| WO | WO-2016000214 A1 | 1/2016 |
| WO | WO-2016019353 A1 | 2/2016 |
| WO | WO-2016023212 A1 | 2/2016 |
| WO | WO-2016023824 A1 | 2/2016 |
| WO | WO-2016026104 A1 | 2/2016 |
| WO | WO-2016029344 A1 | 3/2016 |
| WO | WO-2016061730 A1 | 4/2016 |
| WO | WO-2016061859 A1 | 4/2016 |
| WO | WO-2016074229 A1 | 5/2016 |
| WO | WO-2016090303 A1 | 6/2016 |
| WO | WO-2016090602 A1 | 6/2016 |
| WO | WO-2016095220 A1 | 6/2016 |
| WO | WO-2016103202 A1 | 6/2016 |
| WO | WO-2016106476 A1 | 7/2016 |
| WO | WO-2016106500 A1 | 7/2016 |
| WO | WO-2016108694 A1 | 7/2016 |
| WO | WO-2016109931 A1 | 7/2016 |
| WO | WO-2016109965 A1 | 7/2016 |
| WO | WO-2016115701 A1 | 7/2016 |
| WO | WO-2016119098 A1 | 8/2016 |
| WO | WO-2016119101 A1 | 8/2016 |
| WO | WO-2016119167 A1 | 8/2016 |
| WO | WO-2016119225 A1 | 8/2016 |
| WO | WO-2016120177 A1 | 8/2016 |
| WO | WO-2016122417 A1 | 8/2016 |
| WO | WO-2016123764 A1 | 8/2016 |
| WO | WO-2016123780 A1 | 8/2016 |
| WO | WO-2016123781 A1 | 8/2016 |
| WO | WO-2016127360 A1 | 8/2016 |
| WO | WO-2016127406 A1 | 8/2016 |
| WO | WO-2016141508 A1 | 9/2016 |
| WO | WO-2016145611 A1 | 9/2016 |
| WO | WO-2016149932 A1 | 9/2016 |
| WO | WO-2016154798 A1 | 10/2016 |
| WO | WO-2016172898 A1 | 11/2016 |
| WO | WO-2016179828 A1 | 11/2016 |
| WO | WO-2016184247 A1 | 11/2016 |
| WO | WO-2016201602 A1 | 12/2016 |
| WO | WO-2016202304 A1 | 12/2016 |
| WO | WO-2017001818 A1 | 1/2017 |
| WO | WO-2017001819 A1 | 1/2017 |
| WO | WO-2017021536 A2 | 2/2017 |
| WO | WO-2017028167 A1 | 2/2017 |
| WO | WO-2017035720 A1 | 3/2017 |
| WO | WO-2017055799 A1 | 4/2017 |
| WO | WO-2017055802 A1 | 4/2017 |
| WO | WO-2017055803 A1 | 4/2017 |
| WO | WO-2017066955 A1 | 4/2017 |
| WO | WO-2017070871 A1 | 5/2017 |
| WO | WO-2017082728 A1 | 5/2017 |
| WO | WO-2017093452 A1 | 6/2017 |
| WO | WO-2017093535 A1 | 6/2017 |
| WO | WO-2017107546 A1 | 6/2017 |
| WO | WO-2017109448 A2 | 6/2017 |
| WO | WO-2017113106 A1 | 7/2017 |
| WO | WO-2017124662 A1 | 7/2017 |
| WO | WO-2017137554 A1 | 8/2017 |
| WO | WO-2017153270 A1 | 9/2017 |
| WO | WO-2017156696 A1 | 9/2017 |
| WO | WO-2017163046 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017166263 A1 | 10/2017 |
| WO | WO-2019210402 A1 | 11/2019 |

OTHER PUBLICATIONS

U.S. Appl. No. 17/199,370, filed Mar. 11, 2021, US 20210268206 A1.
U.S. Appl. No. 17/199,377, filed Mar. 11, 2021, U.S. Pat. No. 11,369,755.
U.S. Appl. No. 17/204,148, filed Mar. 17, 2021, U.S. Pat. No. 11,369,756.
U.S. Appl. No. 17/364,436, filed Jun. 30, 2021, U.S. Pat. No. 11,369,757.
U.S. Appl. No. 18/173,712, filed Feb. 23, 2023.
U.S. Appl. No. 18/173,715, filed Feb. 23, 2023.
Brown, C.J. et al, "Electronic cigarettes: product characterisation and design considerations." Tobacco control 23.suppl 2 (2014): ii4-ii10.
Kanger Protank 2 Hardware Review. God of Steam. (Available at https://godofsteam.wordpress.com/2013/08/22/hardware- review-kanger-protank-2/). Accessed Sep. 5, 2024, 6 pages.
Kanger Protank 4 Hardware Review. Jonny. (Avalaible at https://www.ecigclick.co.uk/kanger-protank-4-review/). Accessed Sep. 5, 2024, 7 pages.
Tiku, N. "Startup behind the Lambo of vaporizers just launched an intelligent e-cigarette." (Available at https://www.theverge.com/2015/4/21/8458629/pax-labs- e-cigarette-juul). Accessed Sep. 5, 2024, 4 pages.
Anatomy of a Juul. (Available at https://www.youtube.com/watch?v=7uDQVMTfzFQ). 11 pages.
Juul Pods—How to disassemble and clean for refil(I). (Available at https://www.youtube.com/watch?v=OHF7lv0p5Ms). 22 pages.
Ripping Apart Juul Pods! Whats inside? (Available at https://www.youtube.com/watch?v=MDY1shsTTYQ). 10 pages.
Vaping The Juul. (Available at https://www.youtube.com/watch?v=7NyXFxV6514). 10 pages.
United States International Trade Commission, "Order No. 19: Construing Certain Claim Terms," In the Matter of Certain Oil Vaporizing Devices, Components Thereof, and Products Containing the Same, Inv. No. 337-TA-1392, Aug. 30, 2024, 43 pages.

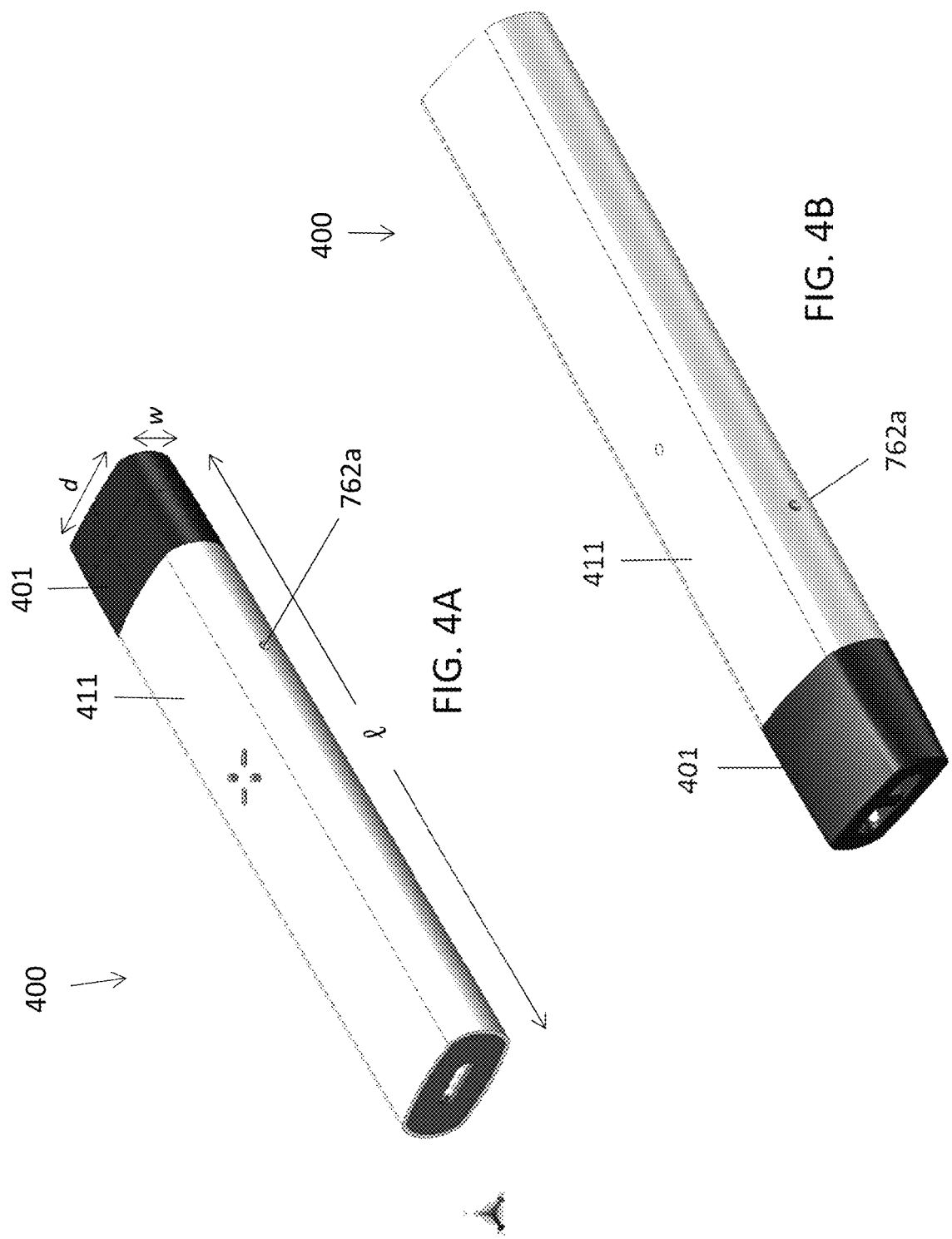

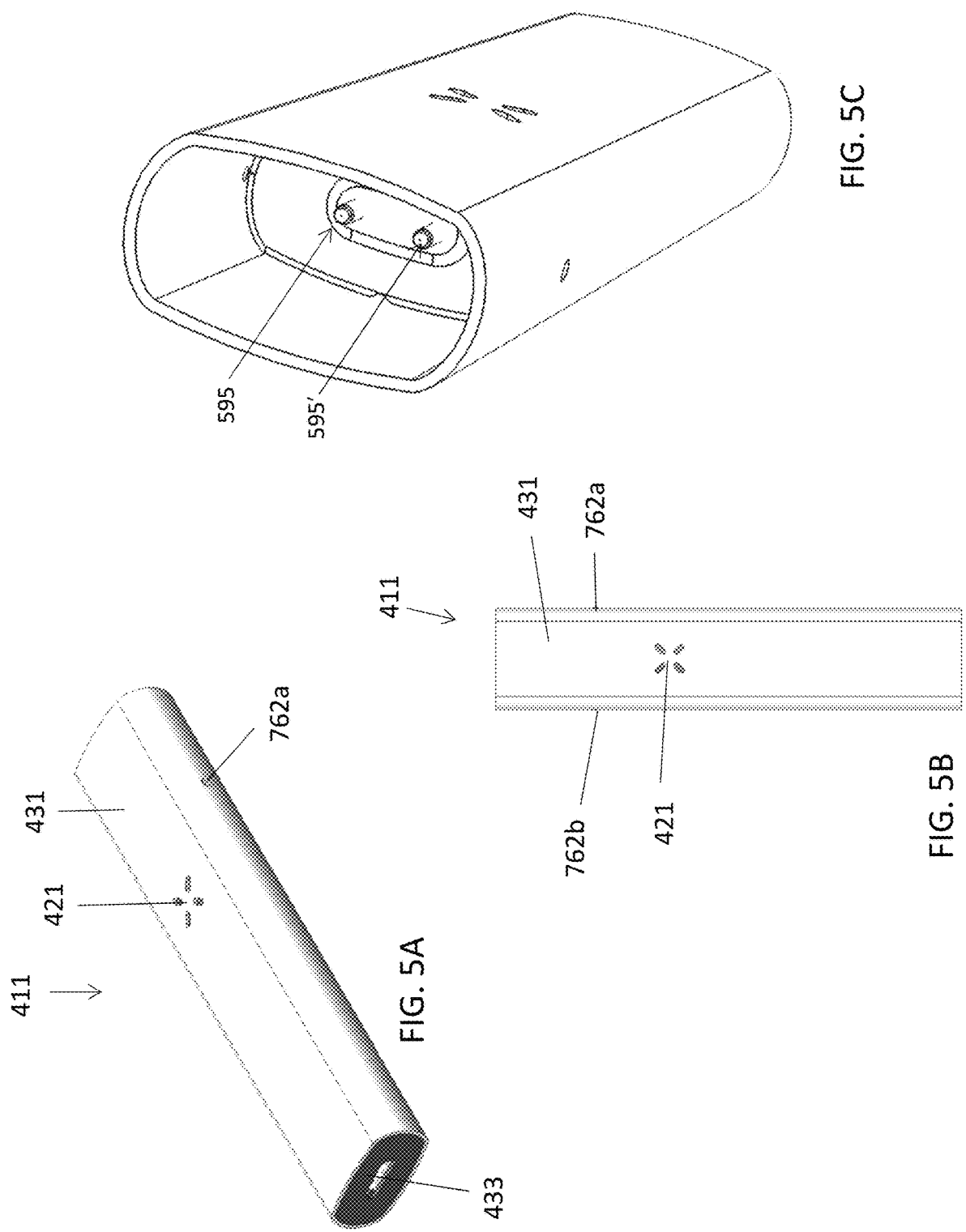

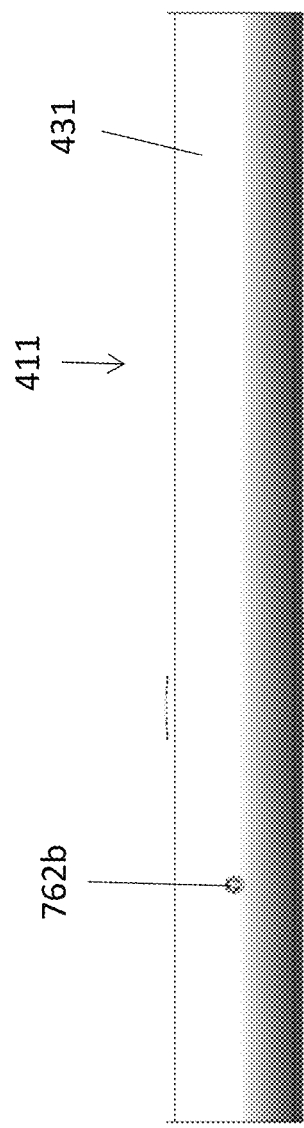
FIG. 5D
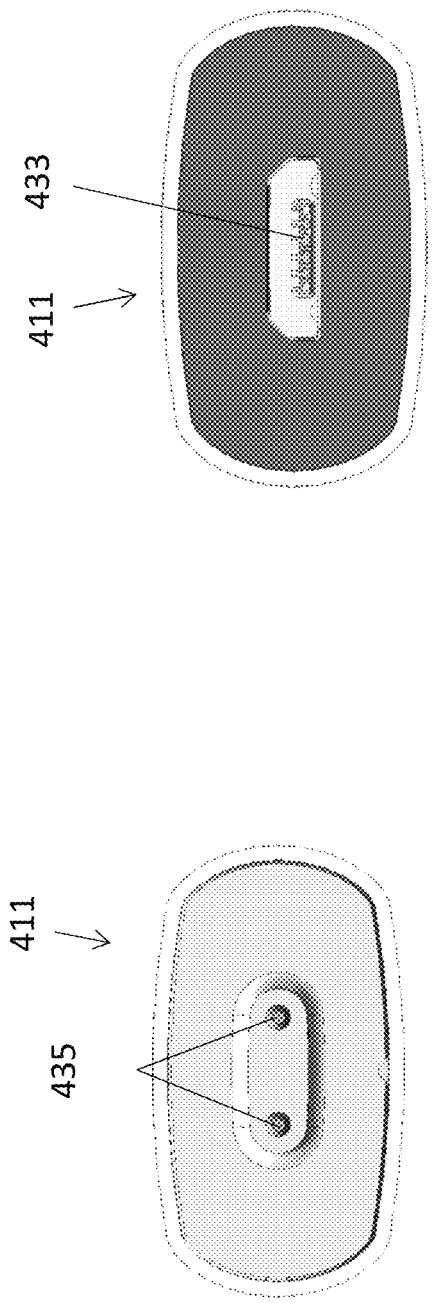
FIG. 5F
FIG. 5E

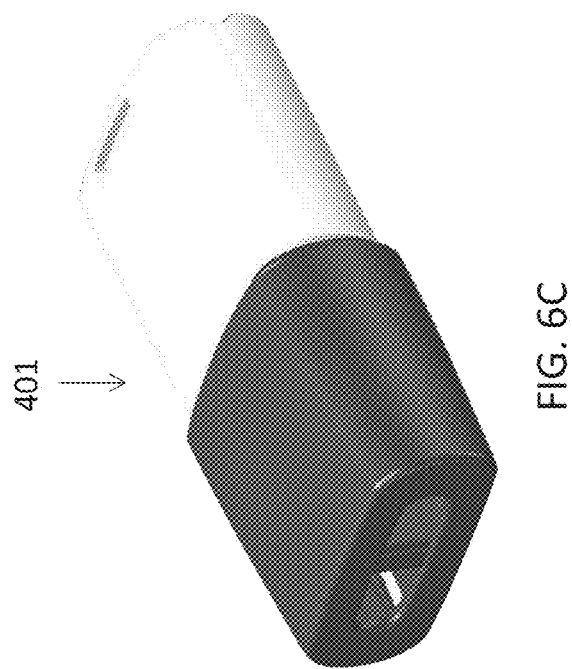
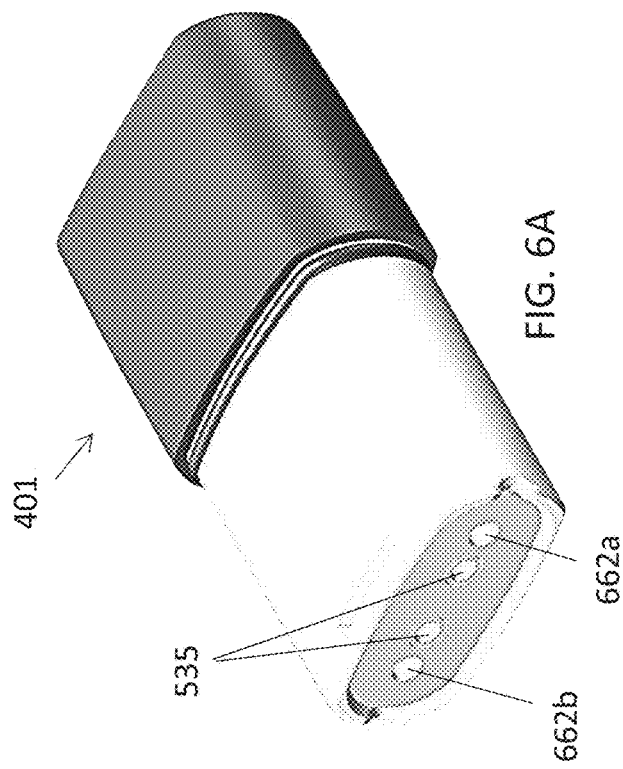
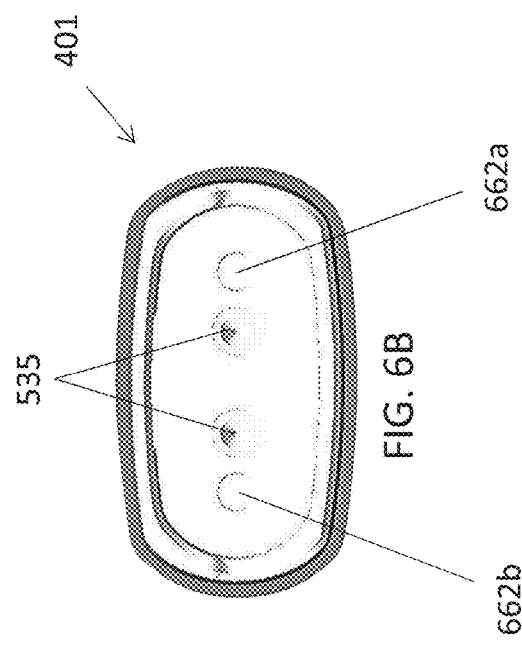

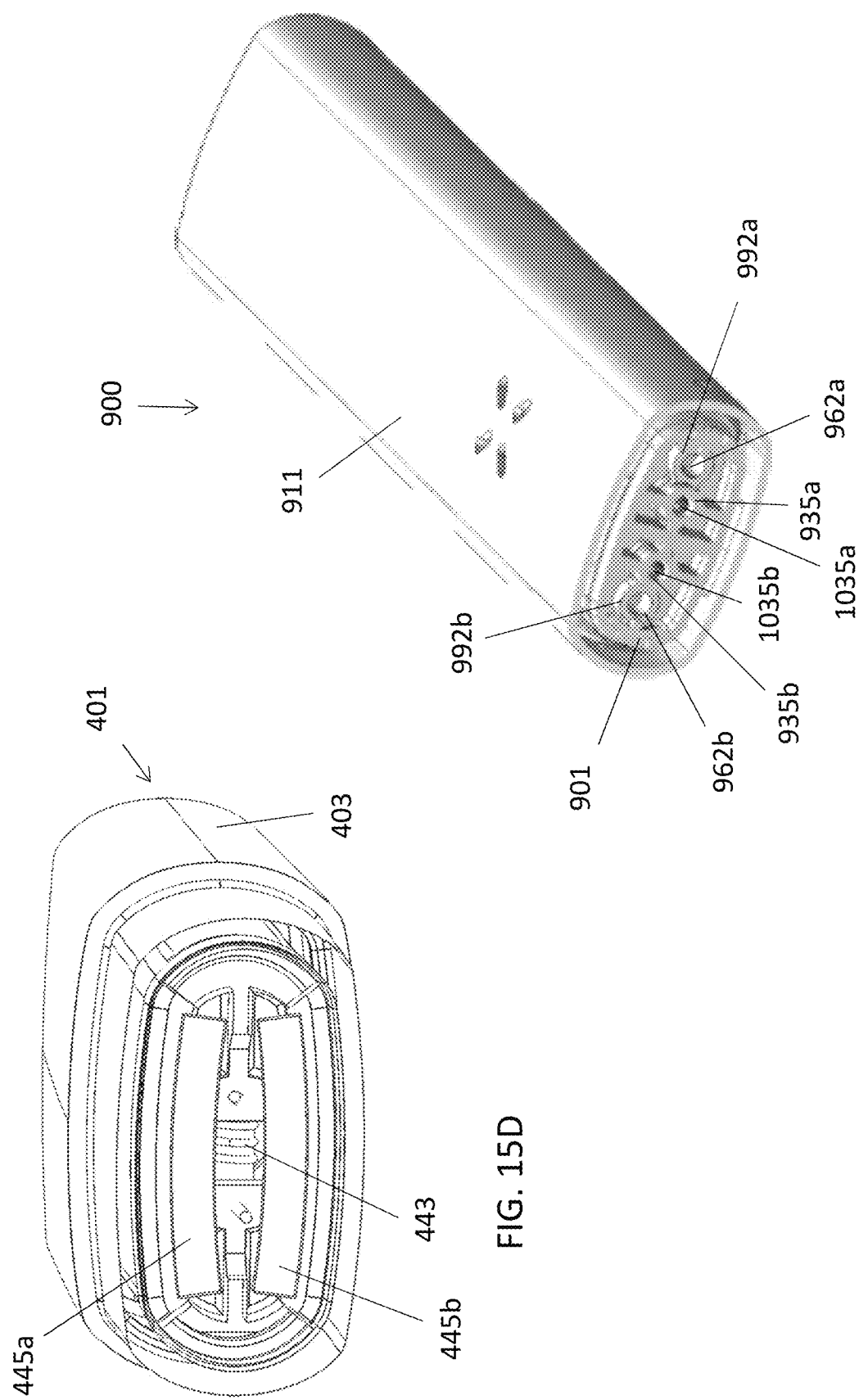

LEAK-RESISTANT VAPORIZER DEVICE

CROSS REFERENCE TO RELATED APPLICATIONS

This application is a continuation of U.S. application Ser. No. 15/396,584, filed on Dec. 31, 2016 and titled "LEAK-RESISTANT VAPORIZER DEVICE", which claims priority to U.S. Provisional Patent Application No. 62/398,494, titled "VAPORIZER APPARATUSES FOR USE WITH CANNABINOIDS", filed on Sep. 22, 2016, the disclosures of which are incorporated by reference herein in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are vaporizer apparatuses, including vaporizer or vaporization devices and vaporizer systems, and methods for making, using and delivering vapor to a user. In particular, vaporizer apparatuses adapted for use with oil-based vaporizable materials including *cannabis* oils.

BACKGROUND

Electronic devices that produce an inhalable aerosol (e.g., inhalable aerosol devices or alternatively referred to as vaporizers, vaporizer devices, vaporization devices, electronic vaping devices, etc.) typically utilize a vaporizable material that is heated to create an aerosol vapor capable of delivering an active ingredient to a user. Vaporizers have been described for vaporizing solids (herbs, tobacco, *cannabis*, etc.), liquids (extracts, waxes, etc.) and combinations of both solids and liquids.

Current market inhalable aerosol devices often consist of a tank or cartridge, vaporizable liquid in the tank or cartridge, an air tube, and a wick/coil subassembly that generates the vapor. Air commonly enters the cartridge through the distal end of the product and is forced through the heated zone where the immediate air becomes fully saturated. As the vapor continues its way through the air tube, it comes in contact with cooler surfaces, causing moisture to collect throughout its use. Depending on the complexity of the air path, particle deposition can add to the existing condensation. As a result, some of the liquid can work its way from the tank or cartridge holding the liquid to other areas of the vaporizer, including the mouthpiece and/or the electronics, causing user dissatisfaction and/or problems with the electronic circuitry.

Conventional vaporizers for aqueous (e.g., water, glycerol, etc.) based vaporizable materials do not manage condensation and leakage of the liquid vaporizable material particularly well, and this problem is particularly acute for oils such as *cannabis* extract oils, in which the liquid material may be particularly oily and/or viscous, and for which evaporation of the liquid material may result in a sticky residue that may impair the operation of the vaporizer. Further, vaporization of *cannabis* extract liquids may be more technically difficult than vaporization of other liquids (such as nicotine solutions).

For example, conventional e-cigarettes may address moisture build-up by integrating a filter pad in line with air flow. However, having a filter pad in line with the air flow can impede or restrict the air flow as the user draws on the mouthpiece. Moreover, this restriction to draw incrementally climbs as the filter becomes more saturated throughout, often requiring the user to change his or her draw accordingly and increasing the possibility of drawing liquid of the product and into the user's mouth.

In addition, the control of the temperature when vaporizing *cannabis* extracts may require a high degree of precision. Virtually all vaporizers currently available today would benefit from a higher degree of precision in power management and control of the heater (atomizer). In particular, vaporizers well suited for vaporizing *cannabis* (e.g., liquid *cannabis* extract solutions) may benefit from precise and accurate control of the heater forming the vapor.

It would also be beneficial to provide cartridges that do not roll and may rest in a small number of secure positions (e.g., cartridges having non-circular cross-sections) and to provide an immediate approximate (visual) estimate of the amount of material consumed.

Finally, it would be particularly beneficial to provide pre-loaded and tightly controllable cartridges for use in consuming *cannabis* extract liquids that prevent or reduce leakage of particularly viscous vaporizable materials such as *cannabis* oils/extracts.

Accordingly, described herein are vaporizers (including vaporizer cartridges) and methods of operating and using them addresses the issues raised above.

SUMMARY OF THE DISCLOSURE

In general, described herein are apparatuses such as devices and systems for vaporizing a material (including, in particular, but not limited to, *cannabis* extract liquids) and method of using them. For example, described herein are vaporizers, cartridges for use with such vaporizers, and vaporizer control systems.

Described herein are vaporizer cartridges that are pre-loaded (filled) with a *cannabis* vaporizer material. The vaporizable *cannabis* material is typically a liquid material, and may be a *cannabis* extract liquid (*cannabis* "oil"). Also described herein are vaporizers with or without cartridges that are adapted for use with *cannabis* liquid extracts. Either or both the vaporizer base (which mates with the vaporizer cartridge to form the vaporizer device) and vaporizer cartridge may be adapted specifically for use with *cannabis* liquid extracts, although any of the apparatuses and methods described herein may be operated with other vaporizable materials, including nicotine solutions and/or solutions having no active ingredient at all (e.g., just including a carrier such as polyether compounds like polyethylene glycol and/or glycerol, or the like, and flavorants).

For example, a cartridge as described herein may include a vaporizable material such as *cannabis* oil. *Cannabis* oils present particular challenges when vaporized using a cartridge and/or a handheld vaporizer device. For example, *cannabis* oil is relatively "sticky" and may be viscous, particularly once it dries out. Thus, leakage may be a more serious consideration and challenge compared to other aqueous vaporizable materials. In particular, leakage of *cannabis* oil may result in clogging of the device and disturbing the electrical components, particularly the electrical contacts, which may be otherwise "gummed up" by leaked oil. The dried oil is not only sticky, but may also be electrically insulative, and may disrupt the electrical control of the vaporizer. Described herein are apparatuses and methods to prevent or control leakage and to avoid disruption of electrical contacts between cartridges containing the *cannabis* extract and the rest of the vaporizer.

For example, the apparatuses described herein may include one or more electrical contacts (e.g., between the cartridge and the vaporizer base) referred to herein as wiping or scraping contacts. These electrical connections may be configured so that as a connection/contact is made between two electrically conductive surfaces, the contact (e.g., on the cartridge and/or the vaporizer base) scrapes the mating surface of the other contact to remove any vaporizable material, including vaporizable material that has dried on the contact. For example, a contact may include a canister with one or more extensions (e.g., wipers, knives, fingers, or scrapers) that are driven against and across the mating surface of the opposite electrical contact to scrape away any leaked vaporizable material (including dried-on material). The complimentary electrical contact may be a pin (including a pogo-pin) electrically conductive connector that is scraped as it enters into the canister by the wiper/scraper(s) therein. Thus, in general, the electrical contact in the vaporizer base may be configured to scrape across and against the corresponding electrical contact surface in the vaporizer cartridge and/or the electrical contact in the vaporizer cartridge may be configured to scrape across and against the corresponding electrical contact surface in the vaporizer base to remove contaminating material. Thus either contact may include a scraping projection (e.g., edge, blade, wire, etc.) that is driven across the opposite surface. Typically two or more contacts are included in the vaporizer cartridge, and each of them may be configured as a scraping or wiping contact. In some variations, it may be desirable to have the scrapers on the connectors of the cartridge, although the scrapers may be present on the vaporizer base instead or in addition.

Any of the cartridges described herein may include a tank or storage region within the cartridge and/or forming a portion of the body of the cartridge. In particular, all or a portion of the cartridge (including the tank) may be clear, transparent and/or translucent so that the level of vaporizable material within the tank can be seen by a user. The tank may be prefilled or fillable. The tank may be sealed closed at the top (near the mouthpiece, which may cover the top of the cartridge). The mouthpiece may be plastic and may be secured over the tank by a snap fit, a friction fit, and adhesive, or the like. For example, the distal end of the elongate and flattened tubular body is configured to be secured by a friction fit within a vaporizer body. As described in greater detail herein, one or more absorbent members, (e.g., sponges, pads, felts, etc.) may be included in the mouthpiece between the tank and the mouthpiece, to prevent leakage of vaporizable material from contacting the portion of the mouthpiece where the user applies her or his lips. The tank may be sealed, e.g., by a tank seal that covers the one or more openings for filling the tank. In some variations, rather than one or more small plugs (which may be difficult to install) the tank may be sealed by a multi-seal component (e.g., a single piece) that seals between the mouthpiece and the top of the tank as and closes off two or more openings into the tank.

During inhalation through the apparatus, the user may draw on the mouthpiece (by inhaling/sucking on the mouthpiece) to draw air through the mouthpiece. The device may be turned on by one or more of: a control on the device (e.g., on an outer surface of the device), but installing the cartridge into the vaporizer base, detecting inhalation, detecting lip contact with the mouthpiece. In some variations, the device is turned on, and the heater rises to an initial set temperature, when the device is in a ready to turn on state and when the user draws on the mouthpiece. The vaporizer may be placed in a ready to turn on state by connecting (or detecting connection of) a cartridge and/or by a switch or control on the outside of the apparatus and/or by the battery level being sufficient to operate the device.

Once the device is turned on, it may be operated by drawing on the mouthpiece to cause the temperature to cause the vaporizer heater (the atomizer) to heat to the desired temperature setting (which may be preset, selected from a plurality of pre-set temperatures or may be user selectable, including using a computer or other device having a processor and user interface that communicates with the device, either wirelessly or via a wired connection, such as a smartphone wirelessly communicating with the device).

Drawing on the mouthpiece typically causes airflow to enter the cartridge receiver region of the vaporizer base through one or more (e.g., two) air openings that are positioned through the wall of the cartridge receiver near a base of the cartridge receiver. Air may pass into the cartridge receiver and up through the cartridge via one or more openings in the base (bottom) of the cartridge. The air may then pass into a heater connector region that also includes one or more (e.g., two, parallel) absorbent pads or sponges for absorbing any leakage of vaporizable material that may enter into this air-filled heater connector region, which is also open to the vaporizing chamber across which a wick and heating coil is extended to form vapor. The two absorbent pads positioned in this air region positioned on the long axis of the cartridge, against the major faces of the cartridge body so that they don't block the air path into the vaporization chamber from the opening(s) at the base. These absorbent pads (e.g., sponges) may prevent dripping or leakage of the fluid from the vaporization chamber (e.g., off of the wick) even when the heater is not being heated. In order to prevent leakage should the absorbent pads not be sufficient, the opening into the base of the air chamber may include a rim or boss on the inner surface (within the heater connector region at the base of the cartridge) that prevents small amounts of fluid (e.g., vaporization fluid such as *cannabis* oil) to drip out of the opening(s) into the cartridge (e.g., the air chamber of the cartridge).

The air path from the vaporization chamber to the mouthpiece may have a minimum diameter that is slightly larger than previously described. For example, the minimum diameter of the air path between the vaporization chamber and the mouthpiece may be about 1.5 mm or greater, about 1.6 mm or greater, than about 1.7 mm or greater, than about 1.8 mm or greater, than about 1.9 mm or greater, than about 2 mm or greater, than about 2.1 mm or greater, than about 2.2 mm or greater, than about 2.3 mm or greater, than about 2.4 mm or greater, than about 2.5 mm or greater, etc. For example the minimum diameter may be 2.0 mm or greater.

In any of the variations described herein, the apparatus may include a wick as part of the atomizer (heater). In variations for use with *cannabis* oil the wick may be larger than typical cartridge wicks and may have a slightly larger pore size, because of the higher viscosity of the *cannabis* oil as compared to other (including nicotine) aqueous vaporization solutions. For example, the wick may be larger than 1.5 mm in diameter (e.g., about 1.9 mm or larger, about 2.0 mm or larger, about 2.1 mm or larger, about 2.2 mm or larger, about 2.3 mm or larger, about 2.4 mm or larger, about 2.5 mm or larger, etc., including between about 1.8 mm and about 5 mm, between about 1.9 mm and about 4 mm, between about 2 mm and about 4 mm, etc.). The wick may generally extend across the vaporization chamber, e.g., along or perpendicular to the long axis of the cartridge, and between either the major or minor sides (in oval or flattened cartridges). The wick material may be any appropriate material, particularly those that are biocompatible, have a sufficient pore size, compatible with *cannabis* oils and may be resistant to heat up to the maximum heating temperature of the apparatus (e.g., will not degrade or combust significantly at temperatures up to about 450° C., 500° C., 550° C., 600° C., 650° C., etc.). For example, the wick may be made of a silica material (e.g., fiberglass).

In any of the heaters described herein, the heater (atomizer) may include a heating coil that may be wrapped around the wick for conductive heating. In any of the variations described herein convective heating of the liquid material (e.g., *cannabis* oil) wicked by the wick. The heating coil may be any appropriate material, but in particular, electrically resistive materials such as nichrome or other resistive materials, particularly those which change their resistance with heat (e.g., having a resistance that increases linearly and predictably with temperature over the desired range of temperatures, e.g., between 30° C. and 600° C., etc., including stainless steel, titanium, nickel, alloys of nickel, etc.).

The cartridge may have any desired shape or configuration. In some variations it may be beneficial in particular to have a shape that is cylindrical, and particularly a flattened cylinder, such as an approximately oval shape, with curved sides. Two of the sides (though curved) may be major sides, having a larger diameter, and two may be minor sides (though curved), having a smaller diameter. The flattened shape may prevent rolling when the device is placed on its side. In some variations the mouthpiece may extend in a slightly tapered shape. The tank may form a central region of the cartridge, bounded by the mouthpiece at one end (at the top) and the air chamber (at the bottom). A central cannula may form the air path between the vaporization chamber and the mouthpiece. The vaporization chamber and cannula may be surrounded by the tank, and may be visible through the walls of the tank (e.g., the vaporization chamber and cannula may be opaque, transparent or translucent). One or more seals, including o-rings, may be used to seal and secure the mouthpiece from the tank and the air chamber (base of the cartridge) from the tank. For example an inner seal may be between the mouthpiece and the outer wall of the tank (which may include a channel or track for the seal/o-ring) and a second seal (o-ring) may be positioned in an inner wall of the tank between the tank and the walls forming the air chamber and/or vaporization chamber at the base of the cartridge.

In any of the variations described herein it may be useful to provide an indication of the amount of the cartridge vaporized, which may be approximately correlated to the dose of the vaporizable material delivered. In any of the apparatuses described herein, the apparatus may include an output (e.g., LED, LCD or other display, etc.) on the apparatus or on a device in communication (e.g., wireless communication) with the apparatus such as a smartphone, laptop, desktop, pad, or the like. The output may indicate a qualitative and/or quantitative amount of the dose of vapor delivered from a particular cartridge. Dose may be determined using the processor of the apparatus to indicate approximately how much of the material, e.g., *cannabis* oil, has been consumed based on the power applied to the heater and the duration of heating. A qualitative output may be provided by sequentially illuminating (and/or changing the intensity and/or color of illumination) of a plurality of LEDs. In another example a 'status bar' showing consumption or dose delivered from a cartridge may be displayed on the apparatus body (e.g., the vaporizer body) or another device (e.g., smartphone) in communication therewith. For example, a plurality of LEDs (RGB) may be illuminated to provide qualitative feedback to a user on the operation of the vaporizer. Upon inserting a cartridge, the vaporizer apparatus may display using the LEDs an illumination corresponding to the intensity of the inhalation and/or the progression of consumption of vaporizable material from the cartridge. The processor in the vaporizer apparatus may estimate a dose based on the power applied to the vaporizer and the duration of heating and/or the duration of draw (inhalation). For example, the power applied*duration of draw may be accumulated by the processor, and the value output. In some variations the output may be provided for display on the body of the apparatus (e.g., by illuminating a sequence of LEDs. This may provide immediate visual feedback to the user.

The apparatuses, and particularly the cartridges, described herein may be adapted specifically for use with oils such as *cannabis* oils. As discussed above, existing cartridges are poorly suited for use with *cannabis* oils, as they may leak. Leaking of *cannabis* oils is both messy and detrimental to the operation of the vaporizer, as the leaked *cannabis* oils may disrupt the electrical connections driving vaporization and may clog or jam the operation of the apparatus. The cartridges described herein may include a number of specific modifications that address these issues; individually, these modifications may be helpful, but as will be described below, in combination these features have proven surprisingly effective at providing a robustly leak-resistant and reliable cartridge when using an oil such as a *cannabis* oil.

For example a cartridge device for holding a vaporizable cannabinoid material without leaking (e.g., that is substantially leak-resistant) may include: an elongate and flattened tubular body extending in a distal to a proximal axis and having a width and a diameter that are transverse to the distal to proximal axis, wherein the diameter is 1.2 times or greater than the width; a tank within a proximal end of the elongate and flattened tubular body, the tank configured to hold the vaporizable cannabinoid material; a mouthpiece at the proximal end of the elongate and flattened tubular body; an overflow leak chamber at a distal end of the elongate and flattened tubular body; an air path extending from the overflow leak chamber through the tank to the mouthpiece; a heater comprising a wick and a heating coil extending within the air path; an opening into the overflow leak chamber from an external surface of the device, wherein the opening is fluidly connected with the air path; and one or more absorbent pads within the overflow leak chamber.

In particular the combination of the flattened elongate body shape (which may be oval or rectangular) along with the enlarged and enclosed overflow leak chamber (typically having an open volume of greater 0.5× or greater the tank volume) at the distal end, and one or more (e.g., two, three, four, etc.) openings into the overflow leak chamber, which may preferably include a lip region around the openings inside the overflow leak chamber. The use of absorbents pads positioned within the overflow leak chamber (e.g., positioned off-axis, along a major wall of the overflow leak chamber, such as the wall extending in the diameter) provides an effective leakage barrier even when changing altitudes or when the user misuses the cartridge, e.g., user-induced failure modes such as biting or squeezing the mouthpiece, and/or blowing into the mouthpiece. Surprisingly, other combinations of such features are less effective, particularly in user-induced failure modes. For example, otherwise similar cylindrical devices, e.g., having a width and diameter that are equivalent or nearly equivalent (e.g., a diameter less than 1.2×, or greater than 0.8×, the width) may show greater leakage compared to more flattened devices; the addition of one or more absorbent pads, particularly along the long wall of an overflow leak chamber) show an even greater reduction in leakage.

The one or more openings into the overflow leak chamber may be present on any surface of the cartridge, including through the distal end of the overflow leak chamber. Although placement of the opening at the distal end may otherwise result in an increase in leakage of the highly viscous oil from the cartridge, including the leak chamber and the absorbent pad(s) prevents or reduces leakage. In addition, the one or more openings may be surrounded by a lip within the leak chamber. The lip may have a height above the inner wall of the chamber that is 0.3 mm or greater (e.g., 0.5 mm or greater, 0.7 mm or greater, 0.8 mm or greater, 0.9 mm or greater, 1 mm or greater, 1.2 mm or greater, 1.3 mm or greater, 1.4 mm or greater, 1.5 mm or greater, 2 mm or greater, etc.).

The one or more absorbent pads may be positioned within the overflow leak chamber along the diameter, off-axis relative to an air flow path through overflow leak chamber from the opening to the air path.

In general, the overflow leak chamber may be relatively large, e.g., the volume of the overflow leak chamber (including the absorbent pad(s)) may be between 0.4 and 1.5× the volume of the tank (reservoir). In particular, the volume of the overflow leak chamber may be between 0.4 and 1× the volume of the tank (e.g., 0.4× or greater, 0.5× or greater, 0.6× or greater, 0.7× or greater, etc. than the volume of the tank). Alternatively, this may be described as the length of the overflow leak chamber along the distal to proximal axis relative to the length of the tank, and may be between 0.4× and 2× the length of the tank along the distal to proximal axis (e.g., between 0.4× and 1×, between 0.5× and 2×, between 0.5× and 1.5×, etc.), typically 0.4× or greater. In general, the overflow leak chamber may be enclosed within the distal end of the elongate and flattened tubular body.

In general, the cartridges described herein may be configured for insertion (e.g., by friction fitting) into a vaporizer body. Thus, the cartridge, and particularly the distal end of the cartridge, may be adapted to be inserted securely into the re-usable vaporizer device. The cartridge may therefore have straight (e.g., flat) or inwardly tapered sides and may include one or more friction-engagement regions that couple within the vaporizer. In some variations the distal end region of the cartridge may include a channel, rim, lip, ridge, protrusion, etc. that may engage with a complimentary region in the vaporizer (e.g., in a cartridge receiver in the vaporizer body). Thus, the cartridge may be configured to 'snap' fit into the vaporizer body. For example, the distal end of the elongate and flattened tubular body may include a lip or rim configured to snap into a vaporizer body.

The cartridge may also include one or more (e.g., a pair) of electrical contacts on the distal end of the cartridge (e.g., on the distal end of the overflow leak chamber) in electrical communication with the heater. These electrical contacts may also be configured and adapted to prevent or ameliorate the effects of leakage of oil from the cartridge. For example, the electrical contacts may comprise scraping contacts (also referred to as wiping or wiper contacts), which may include an edge or edge to scrape against the contact (e.g., pogo pin) from the vaporizer before (and/or separately from) making electrical contact. For example, the pair of electrical contacts may comprise pin receptacles. These pin receptacles may include an outer scraping edge with an inner conductive surface.

In any of the variations described herein, the tank may include a cannabinoid solution (e.g., a *cannabis* oil solution). Thus, the cartridge may be pre-filled with a *cannabis* oil. The tank volume may be configured to hold between about 0.2 mL and about 2 mL or more of oil. For example, the tank may be configured to hold between about 0.4 mL and about 1.2 mL (e.g., between about 0.4 mL and 0.8 mL, etc.)

The mouthpiece may be configured to fit over the proximal end of the elongate and flattened tubular body, and may be in fluid communication with the air path through the tank. The mouthpiece may include an internal volume; one or more absorbent pads may be positioned within this internal volume. The one or more mouthpiece absorbent pads within the mouthpiece may generally be off-axis relative to the air path (leaving a central air path that is not occluded by the absorbent pads). For example, the mouthpiece absorbent pads may be off-axis relative to an air flow path from the air path and out of the mouthpiece. The mouthpiece absorbent pads may be positioned on the sides of the mouthpiece (e.g., the major sides, corresponding to the diameter of the mouthpiece). The absorbent pad(s) may be between a proximal end of the mouthpiece and the elongate and flattened tubular body.

In any of the devices described herein the air path may extend through the cartridge, from the distal end (e.g., the opening(s) into the overflow leak chamber), past the heater, through and/or around the tank, and out of the mouthpiece. In some variations, the air path comprises a cannula extending through the tank. In general, the elongate body may be transparent or translucent, and any material in the tank may be visible; when the device includes a cannula running through the tank this may also be visible.

The absorbent pads in the overflow leak chamber may be the same material and/or dimensions as those (if present) in the mouthpiece, or they may be different materials and/or dimensions. The one or more absorbent pads may be made of a sponge or felt material. The one or more absorbent pads may comprise a pair of flat absorbent pads arranged in parallel. For example, the one or more absorbent pads may comprise a cotton material. The one or more absorbent pads may be rectangular.

As mentioned, the one or more absorbent pads in the overflow leak chamber may be a pair of absorbent pads positioned within the overflow leak chamber off-axis relative to an air flow path through the overflow leak chamber from the opening to the air path.

The heater (e.g., wick and coil) may be positioned within the air path so that it is parallel, transverse or oblique to the air path. For example, the heater may extend across the air path in a transverse direction.

The elongate and flattened tubular body may have an oval cross-section or a rectangular cross-section transverse to the distal to proximal axis, and may be any appropriate size. For example, the elongate tubular housing may be between about 1 cm and 10 cm long (e.g., between about 2 cm and 7 cm long, etc.). It may be particularly beneficial to have the elongate tubular housing be somewhat short and compact (e.g., less than 8 cm, less than 7 cm, less than 6 cm, less than 5.5 cm, less than 5 cm, etc.)

The sizes of the openings into the air path (through the overflow leak chamber, e.g., at the distal end of the cartridge) may be configured to allow relatively easy draw through the cartridge, while preventing leakage out of the overflow leak path. Leaking may occur from the heater (e.g., the exposed wick) which is inserted through the wall of the tank; the air path within the cartridge is open and continuous, which would otherwise allow the material to leak. Thus, for example, the size of the one or more openings may be specified within a range identified as allowing sufficient air flow without permitting excessive leaking. For example, in some variations, the diameter of the opening(s) into the overflow leak chamber is/are between 0.1 mm and 5 mm (e.g., between 0.1 mm and 3 mm, between about 0.1 mm and 2 mm, etc.).

The tank portion of the device may be filled by an opening beneath the mouthpiece, which may be sealed or plugged. For example, the cartridge may include a plug between the mouthpiece and the elongate and flattened tubular body, wherein the plug closes off the tank of the elongate and flattened tubular body.

Any of the cartridge devices for holding a vaporizable cannabinoid material without leaking may include: an elongate and flattened tubular body extending in a distal to a proximal axis and having width and diameter that are transverse to the distal to proximal axis, wherein the diameter is 1.2 times or greater than the width; a tank within a proximal end of the elongate and flattened tubular body, the tank configured to hold the vaporizable cannabinoid material; a mouthpiece on the proximal end of the elongate and flattened tubular body; an enclosed overflow leak chamber at a distal end of the elongate and flattened tubular body, The device of claim 1, wherein a length of the overflow leak chamber along the distal to proximal axis is 0.5 times or greater than a length of the tank along the distal to proximal axis; an air path extending from the overflow leak chamber through the tank to the mouthpiece; a heater comprising a wick and a heating coil extending within the air path proximal to the overflow leak chamber; an opening through the distal end of the overflow leak chamber, wherein the opening is surrounded by a lip within the leak chamber and further wherein the opening is fluidly connected with the air path; and one or more absorbent pads within the overflow leak chamber.

For example, a cartridge device for holding a vaporizable cannabinoid material without leaking may include: an elongate and flattened tubular body extending in a distal to a proximal axis and having width and diameter that are transverse to the distal to proximal axis, wherein the diameter is 1.2 times or greater than the width; a tank within a proximal end of the elongate and flattened tubular body, the tank configured to hold the vaporizable cannabinoid material; a mouthpiece at the proximal end of the elongate and flattened tubular body; an overflow leak chamber at a distal end of the elongate and flattened tubular body, wherein a length of the overflow leak chamber along the distal to proximal axis is between 0.5 and 2 times a length of the tank along the distal to proximal axis; an air path extending proximally from the overflow leak chamber through the tank to the mouthpiece, wherein the air path comprises a cannula extending through the middle of the tank; a heater comprising a wick and a heating coil extending within the air path; an opening into the overflow leak chamber from an external surface of the device, wherein the opening is surrounded by a lip within the leak chamber and further wherein the opening is fluidly connected with the air path; and one or more absorbent pads within the overflow leak chamber.

BRIEF DESCRIPTION OF THE DRAWINGS

FIGS. 4A and 4B show an exemplary vaporization device. This exemplary device includes two pairs of absorbent filter pads, as described herein. FIGS. 4A and 4B show a cartridge placed within the reusable component of the device.

FIGS. 5A-5F illustrate the vaporizer body (e.g., a reusable component of the vaporizer device of FIGS. 4A and 4B). FIG. 5A is a bottom perspective view; FIG. 5B is a front view, FIG. 5C is a top perspective view (looking into the cartridge receiver region including electrical contacts), FIG. 5D is a side view, FIG. 5E is a top view, and FIG. 5F is a bottom view, showing the electrical connection to a charger or other wired electrical connection.

FIGS. 6A-6D illustrate the cartridge of the device of FIGS. 4A and 4B. FIG. 6A is a bottom perspective view, FIG. 6B is a bottom view, FIG. 6C is a top perspective view (showing the opening into the mouthpiece) and FIG. 6D is an exploded view of the cartridge of FIG. 6A.

FIG. 7A shows a bottom perspective view; FIG. 7B is a top perspective view; FIG. 7C is a front view; FIG. 7D is a side view; FIG. 7E is a bottom view; and FIG. 7F is a top view.

FIG. 8A is a bottom perspective view; FIG. 8B is a top perspective view showing the cartridge receiver portion of the vaporizer base; FIGS. 8C, 8D and 8E show front, side and back views, respectively of the vaporizer base; and FIGS. 8F and 8G show bottom and top views, respectively of the vaporizer base.

FIGS. 9A and 9B show bottom perspective and top perspective views, respectively, of the assembled vaporizer apparatus; FIGS. 9C, 9D and 9E show front, side and back views, respectively of the assembled vaporizer apparatus; FIGS. 9F and 9G show bottom and top views, respectively, of the vaporizer apparatus.

FIG. 15D is a section through a cartridge (through line 15D-15D' of a cartridge such as the one shown in FIG. 7A) showing a pair of overflow filter pads that are off-axis relative to the airflow path of the device.

FIG. 16 is a section through another of another exemplary vaporization device (at line 16-16' in FIG. 9B), near the base of the cartridge and inserted into the cartridge receiver of the vaporizer base.

DETAILED DESCRIPTION

Figure 1:
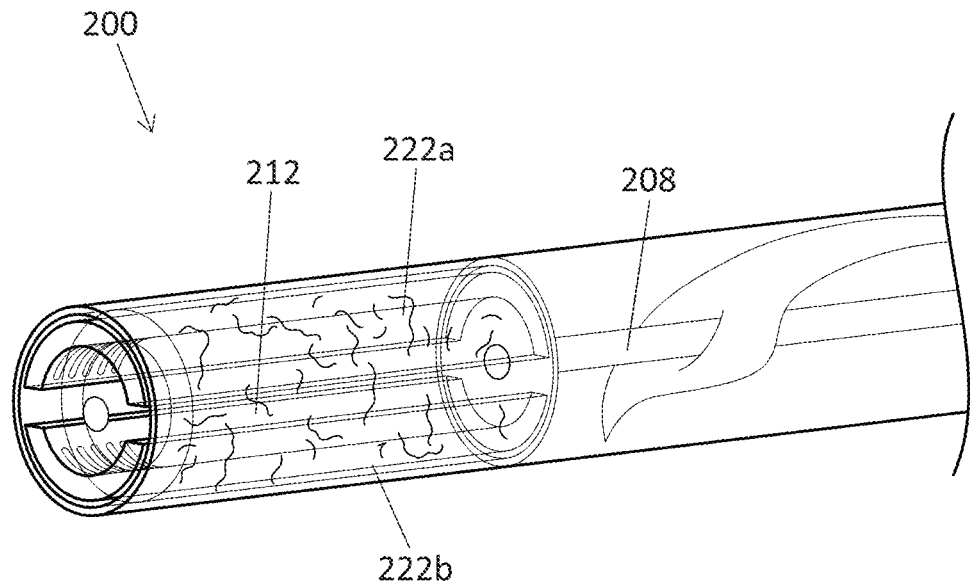
FIGS. 1 and 2 show moisture and vapor deposition on a pair of filter pads that are off-axis relative to the airflow path of the device.

The apparatuses and methods described herein generally include forming a vapor from a material (including in particular, liquid and oil-type plant materials) using a vaporization device. The vapor may be delivered for inhalation by a user. These apparatuses may be particularly adapted for use with an oil-based vaporizable material, including *cannabis* oils.

The vaporizer apparatuses, including cartridges (vaporizer cartridges) and reusable vaporizers bases described herein may be used with any appropriate vaporizable material, including aqueous vaporizable materials. These apparatuses may be particularly well adapted for use with viscous, oil-based vaporizable materials, including *cannabis* oils. For example, any of the cartridges described herein may be used (e.g., filled) with a vaporizable material comprising viscous liquid such as a *cannabis* oil. In some variations the *cannabis* oil comprises between 40-100% *cannabis* oil extract. The viscous oil may include a carrier for improving vapor formation, such as propylene glycol, glycerol, etc., at between 0.01% and 25% (e.g., between 0.1% and 22%, between 1% and 20%, between 1% and 15%, etc.). In some variations the vapor-forming carrier is 1,3-Propanediol. A *cannabis* oil may include a cannabinoid or cannabinoids (natural and/or synthetic), and/or a terpene or terpenes. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g., ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 20-80% cannabinoids (e.g., 30-90%, 40-80%, 50-75%, 60-80%, etc.), 0-40% terpenes (e.g., 1-30%, 10-30%, 10-20%, etc.), and 0-25% carrier (e.g., polyethylene glycol).

In any of the oil vaporization materials described herein (including in particular, the cannabinoid-based vaporization materials, the viscosity may be within a predetermined range. The range may be between about 30 cP (centipoise) and 115 KcP (kilocentipoise). For example, the viscosity may be between 40 cP and 113 KcP. Outside of this range, the vaporizable material may fail to wick appropriately to form a vapor as described herein. In particular, the oil may be made sufficiently thin to both permits wicking at a rate that is useful with the apparatuses described herein, while also limiting leaking (e.g., viscosities below that of −40 cP might result in problems with leaking).

Figure 7C:
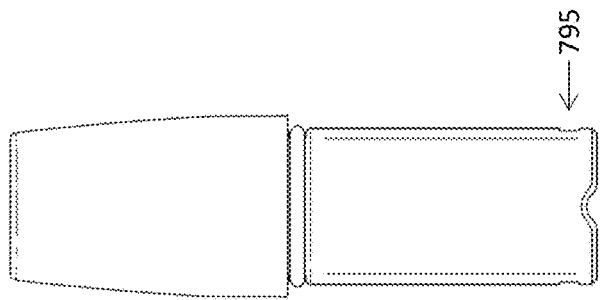
FIGS. 7A-7F illustrate an alternative view of a cartridge as described herein.
Figure 7D:
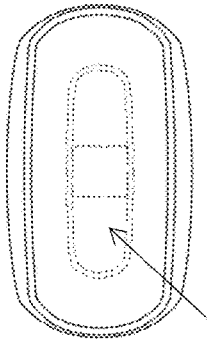
Figure 7E:
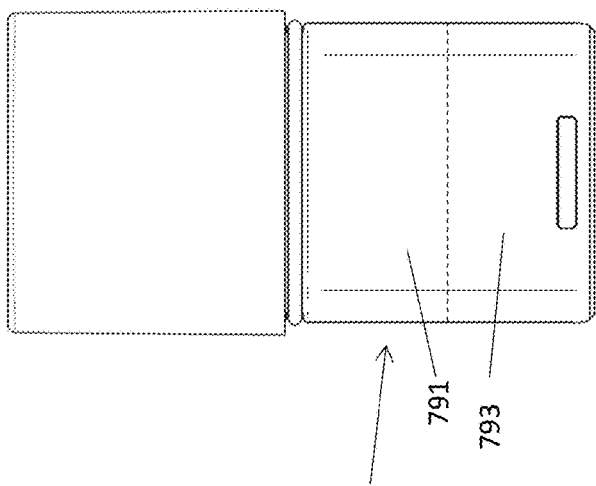
Figure 7F:
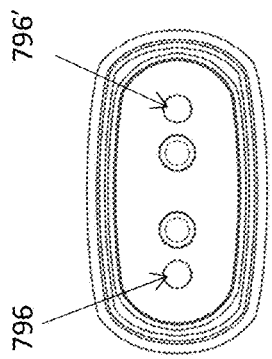
Figure 7A:
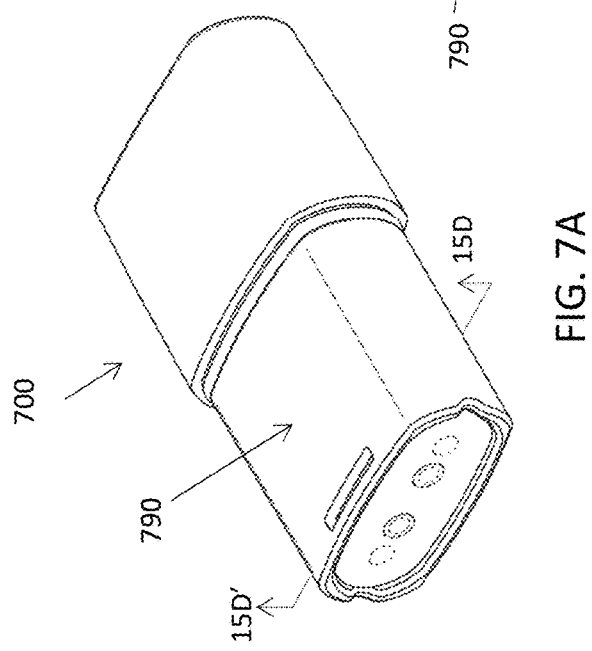
Figure 7B:
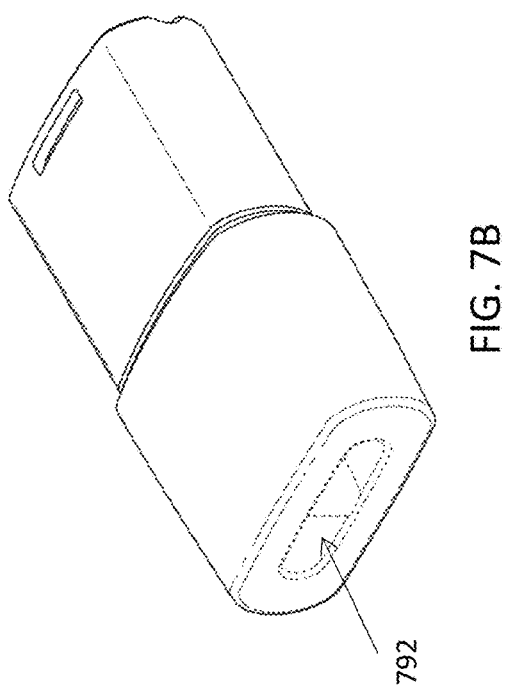
Figure 8E:
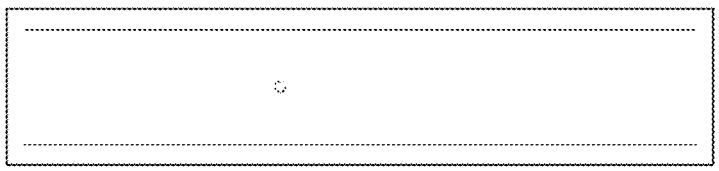
FIGS. 8A-8G show a variation of a vaporizer base of a vaporizer apparatus into which a cartridge such as the one shown in FIGS. 7A-7F may be inserted.
Figure 8D:
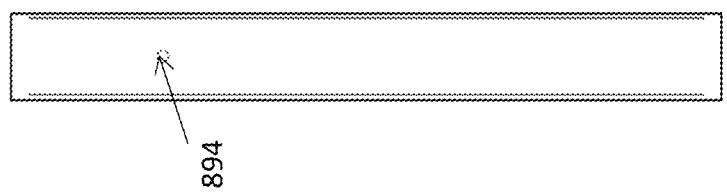
Figure 8C:
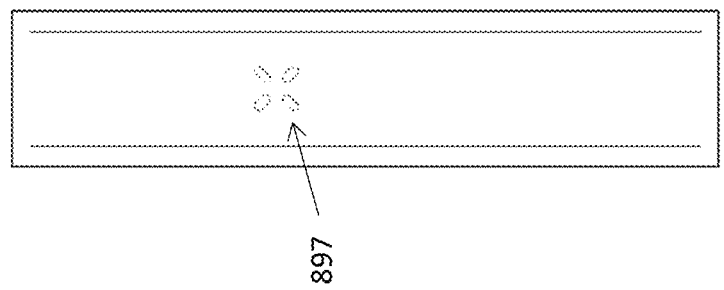
Figure 8G:
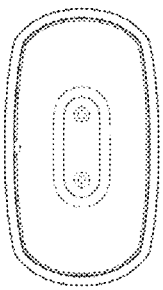
Figure 8F:
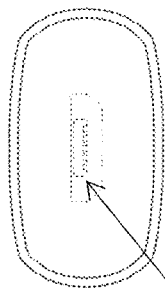
Figure 8A:
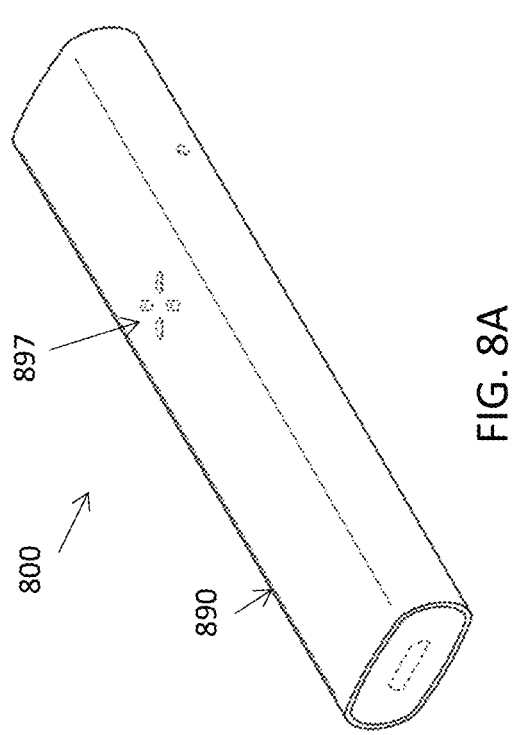
Figure 8B:
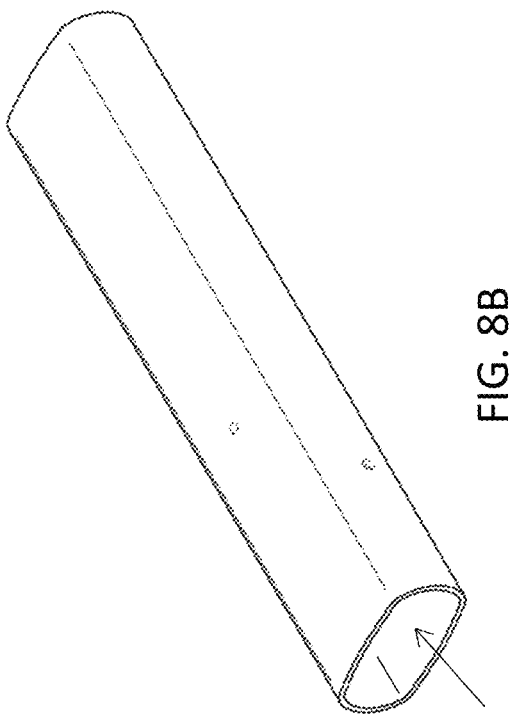

For example, FIGS. 7A-7F illustrate one example of a cartridge that is adapted for use with a viscous oil-based vaporizable material (having a viscosity at room temperature of between 40 cP and 113 KcP), such as a *cannabis* oil. In this example, the cartridge 700 includes a flattened body that is approximately oval in cross-sectional area (see, e.g., FIGS. 7E and 7F showing top and bottom views) and includes a mouthpiece that is attached over a clear body forming a reservoir region holding the vaporizable material. The body 790 may be transparent, translucent or opaque. The mouthpiece may include one or more openings 792 at the proximal end (top) out of which vapor may be inhaled, by drawing breath through the device. The bottom may also include a locking feature (e.g., tab, indent, magnetic lock, etc.) for coupling and securing the cartridge within a cartridge receiver of a vaporizer base, such as the reusable vaporizer base 800 shown in FIGS. 8A-8G. In this example, the body may be elongate and may include an outer shell or cover 890; the proximal end of the vaporizer base may include an opening forming a cartridge receiver 892. The cartridge receiver may include one or more opening therethrough (e.g., lateral openings) to allow airflow therein, as described in more detail below. Any of these cartridges may also or alternatively include a rim, ridge, channel, protrusion, lip, etc. along the distal end region for engaging a complimentary portion of the vaporizer device. For example, in FIG. 7D, the cartridge include a channel or lip 795 at the distal end which may engage with a deflectable or deformable tab or protrusion in the cartridge receiving portion of the vaporizer; this may provide a snap fit. In general, the cartridge may fit within the cartridge receiver of the vaporizer by a friction fit. The snap-fit may provide audible and/or tactile confirmation that the cartridge is held in position. This fit may also lock or hold the cartridge within the receiver, but still allow it to be easily withdrawn to remove the cartridge.

As shown in FIG. 7C, the elongate and flattened body 790 may contain within it the tank region 791 (e.g., holding the vaporizable oil material) and a distal overflow leak chamber 793. These structures may be formed by the internal components within the elongate and tubular body, as shown below.

Figure 10A:
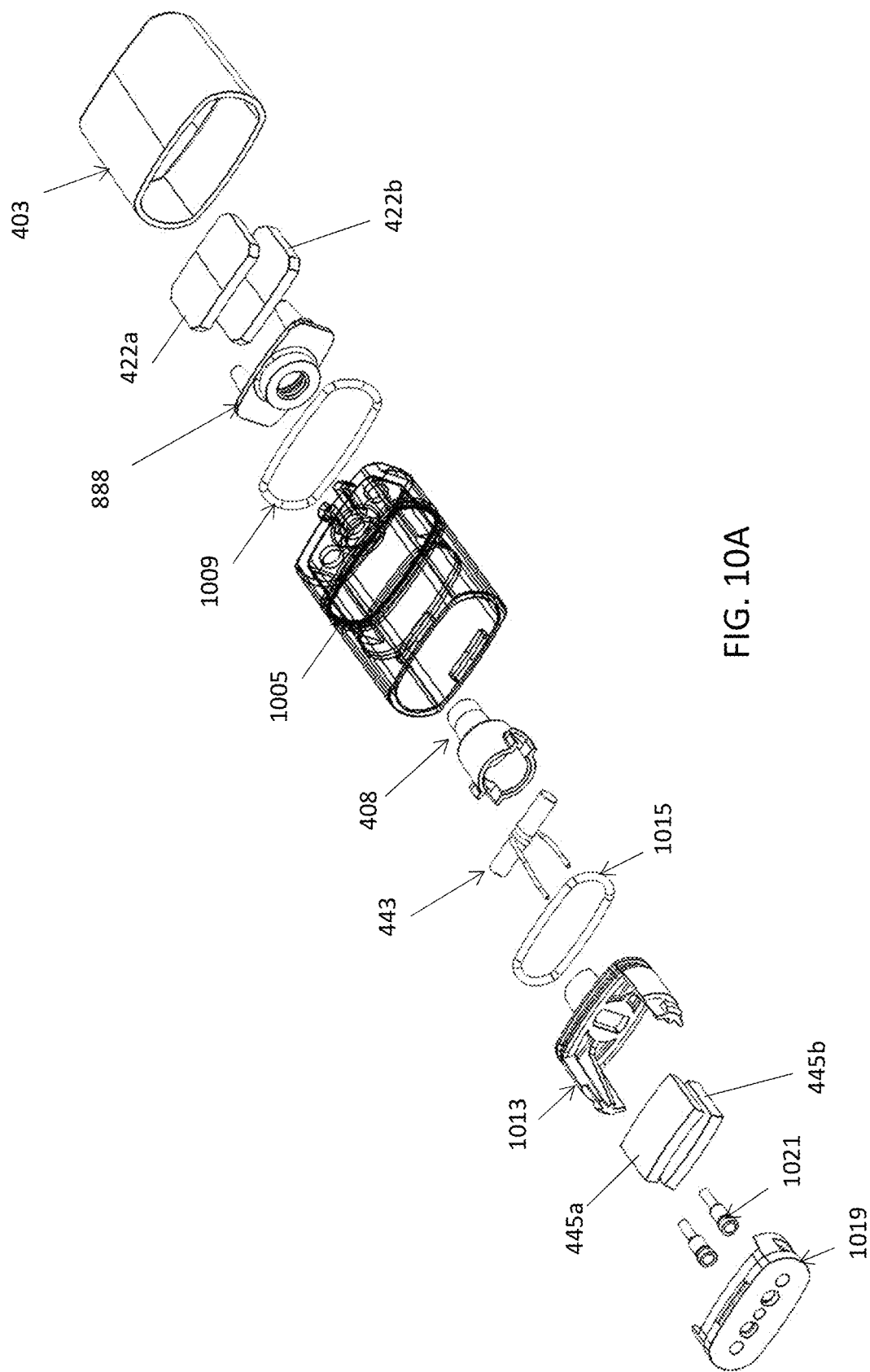
FIG. 10A is an exploded view of the cartridge of FIGS. 7A-7F with the components arranged in line.
Figure 10B:
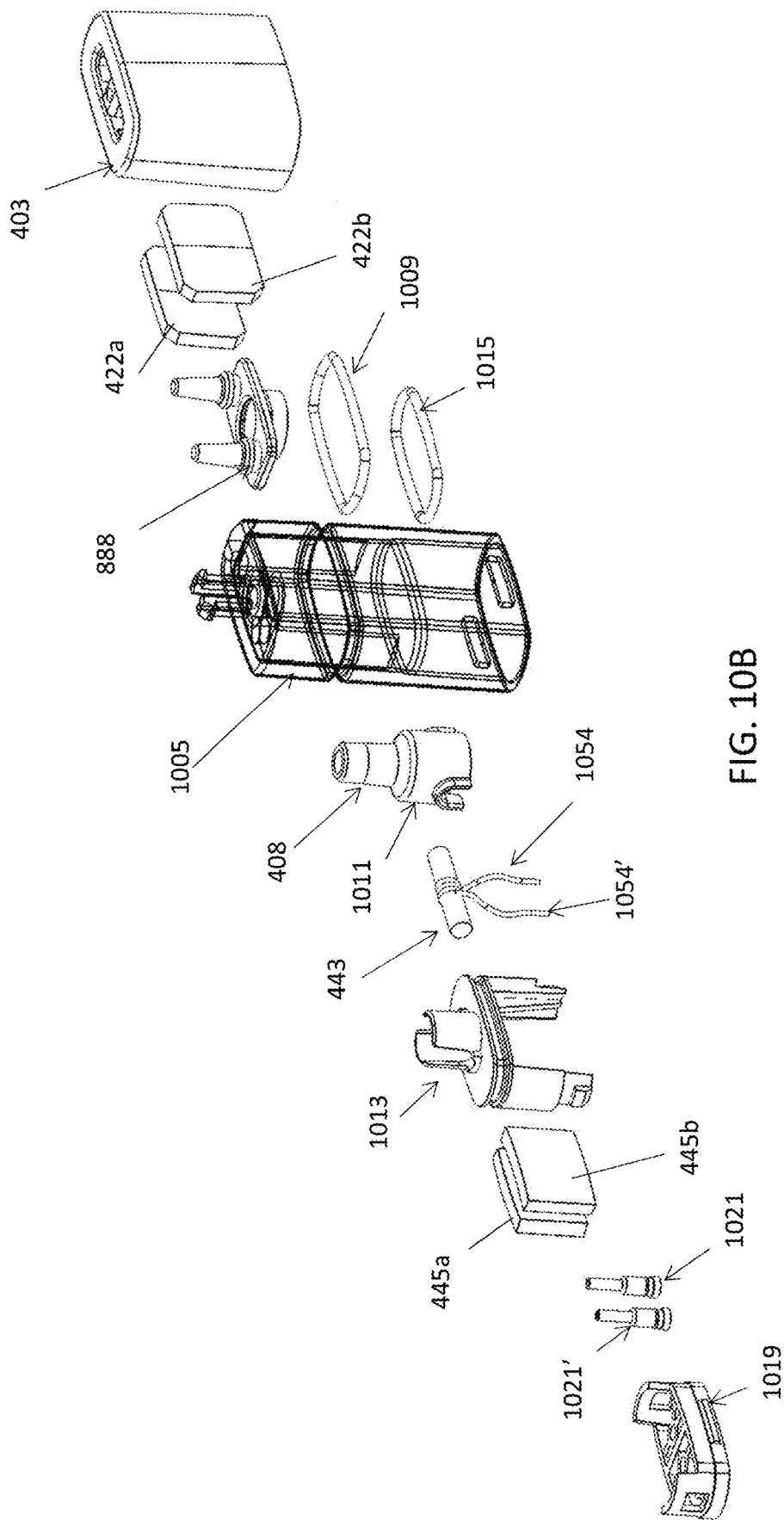
FIG. 10B is an alternative exploded view of the cartridge of FIGS. 7A-7F, showing the component parts positioned adjacent to each other at the approximate vertical position for assembly.

FIGS. 10A and 10B show exploded view of a cartridge as described herein. In this example, the apparatus includes a cartridge body 1005 that may be clear (transparent), opaque and/or translucent. The cartridge body may form a reservoir for the liquid vaporizable material, and particularly for a viscous liquid vaporizable material such as the cannabinoid oils described herein. The cartridge may include an outer seal (e.g., o-ring 1009) that seals the mouthpiece 403 over the body 1005. The reservoir (tank) may be sealed on the top (at the proximal end) under the mouthpiece by a single-piece plug 888 that covers multiple openings which may be used for filling the tank. The vaporization chamber may be formed at the bottom (distal end) of the cartridge; in exemplary cartridges described herein the vaporization chamber is formed from a cannula and housing piece 1011 that includes opening into which the wick (wick portion of wick and coil 443) passes into the chamber; the walls forming the vaporization chamber separate it from the tank and mate with a back piece 1013 that forms the bottom (distal end) of the tank within the cartridge body. This piece is also sealed (e.g., by an o-ring 1015) to the cartridge body from within the cartridge body, as shown. An air chamber is then formed between the bottom of the cartridge 1019 and the back piece 1013 of the tank. One or more (e.g., two) air openings 796, 796' through this bottom 1019 allow air to pass (after entering the cartridge receiver through one or more openings 894 in the side) into the distal end of the cartridge, into the air chamber region and then up through an opening into the vaporization chamber. The piece forming the bottom of the cartridge 1019 may also accommodate or include one or more (e.g., two) electrical connectors that are configured to mate with the connectors on the vaporizer base. As mentioned, these contacts may be wiper or scraping contacts. In FIGS. 10A and 10B, they are shown as cans 1021, 1021' having openings into which the pins project to form an electrical contact.

The vaporizer body typically includes a battery and one or more control circuits housed within the cover 890. The control circuitry may control the heater, which in this example, is present in the cartridge. The heater may generally include a heating coil (resistive heater) in thermal contact with the wick; additional connectors formed of a different material (e.g., conductive material) may connect the heater coil to the electrical contacts on the base of the cartridge; although this may lead to inaccuracies in detecting and controlling temperature electrically, as described below, the control circuitry may include one or more additional circuits, such as Seebeck measurement circuits, that correct for offsets and other inaccuracies in the determination of temperature and therefore the power applied to the apparatus. The control circuitry may also include and may control and/or communicate with a batter regulator (which may regulate the battery output, regulate charging/discharging of the battery, and may provide alerts to indicate when the battery charge is low, etc.). The co control circuitry may also include and may control and/or communicate with an output, such as a display, one or more LEDs, one or more LCDS, a haptic output, or any combination of these. In the example shown in FIGS. 7A-9G, the apparatus includes only four (RGB) LEDs 897, arranged in a pattern (e.g., a circular, spiral or floral pattern; other patterns may include linear patterns). Any of the apparatuses described herein may also include a wireless communication circuitry that is part of, connected and/or controlled by the control circuitry. The apparatus may be configured to wireless communicate with a remote processor (e.g., smartphone, pad, wearable electronics, etc.); thus the apparatus may receive control information (e.g., for setting temperature, resetting a dose counter, etc.) and/or output information (dose information, operational information, error information, temperature setting information, charge/battery information, etc.).

Figure 11A:
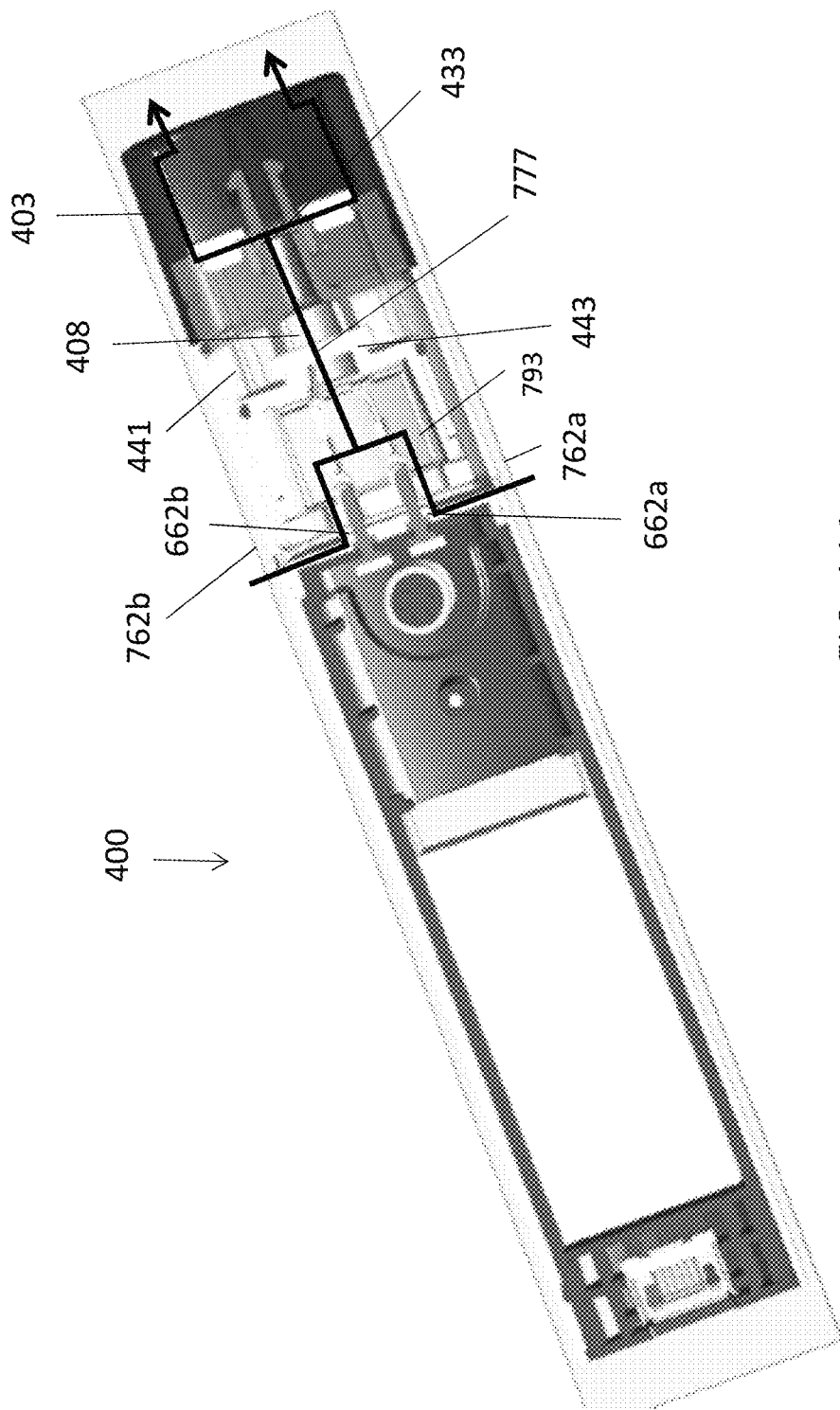
FIG. 11A is a semi-transparent view (in which the outer casing of the vaporizer base, mouthpiece, and cartridge housing have been a made transparent) showing the air path through the assembled vaporizer apparatus such as the one shown in FIGS. 7A-9G.
Figure 11B:
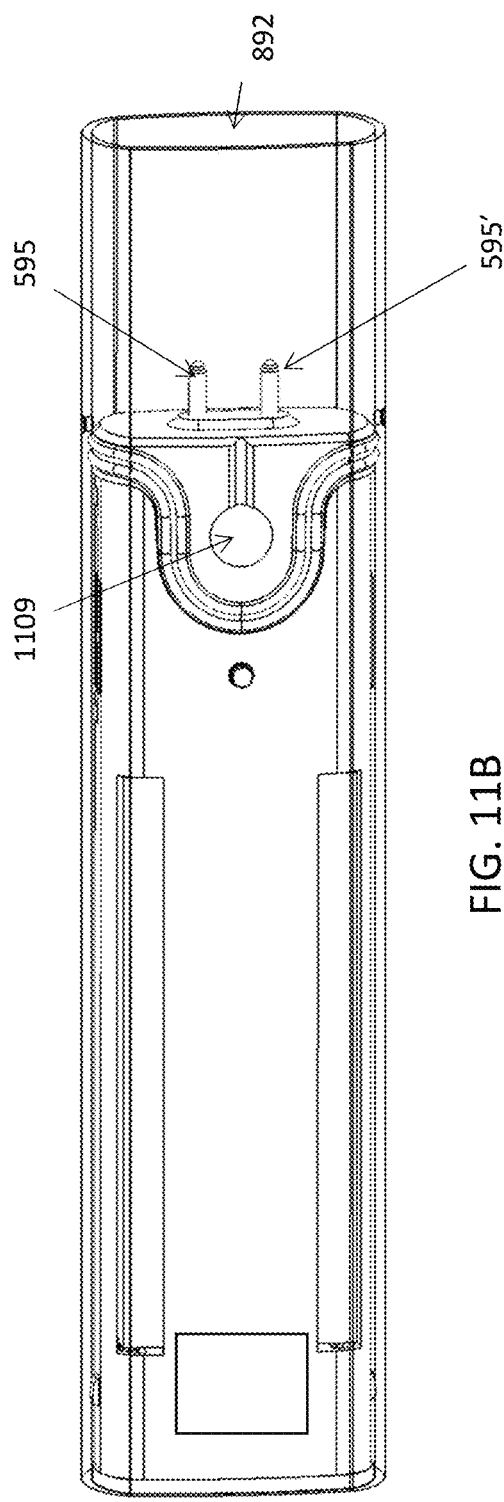
FIGS. 11B and 11C show front and back views, respectively, of an example of a vaporizer base with the outer housing (case or shell) made transparent, showing the cartridge receiving end including connectors and air entry port therein.
Figure 11C:
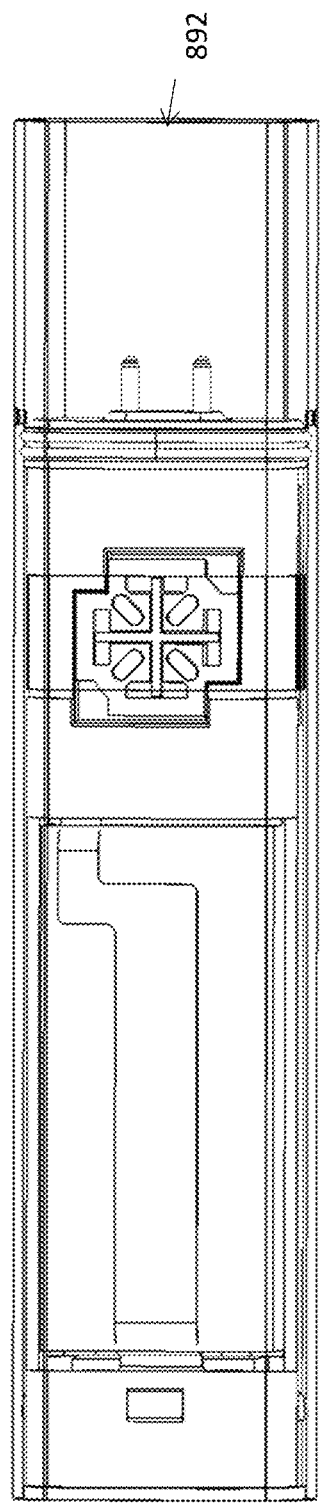

The apparatus may also include one or more inputs, such as an accelerometer, a lip sensing input, a contact input, or the like. In particular, described herein are vaporizer apparatuses in which the device does not include any visible buttons, switches or external user input on an outer surface of the cartridge or vaporizer base. Instead, the input may be an accelerometer (coupled to, part of, and/or controlled by the control circuitry). The accelerometer and any accelerometer control circuitry may be configured to detect tapping on the apparatus (e.g., the case) and/or rolling of the apparatus (e.g., around the long axis or the short axis of the device). In some variations the apparatus may also include circuitry for sensing/detecting when a cartridge is connected and/or removed from the vaporizer base. For example, cartridge-detection circuitry may determine when a cartridge is connected to the device based on an electrical state of the electrical contacts within the cartridge reliever in the vaporizer base. For example, FIG. 5C illustrates the two electrical contacts 595, 595'. Without a cartridge inserted into the apparatus the circuit is open (e.g., between 595 and 595') with the cartridge inserted, the electrical contacts (shown as pins 595, 595' in FIGS. 5D and 11B) engage with the contacts (such as wiping contracts, described above, which scrape to remove leaked and/or dried vaporizable material on the electrode contact surfaces). The controller (via a separate or integrated cartridge-detection circuit) may determine that a cartridge has been inserted when the resistance between these contacts changes to within a recognizable range (from the open circuit). Other cartridge detectors may be used alternatively or additionally, including a trip switch (which is activated when the cartridge is present), or the like. Any of the apparatuses described herein may also include one or more breath detectors, including a pressure sensor 1109 (e.g., microphone coil) having a connection to the inside of the cartridge receiver, as shown in FIG. 11B.

The vaporizer body may also include a connector 899 at the distal end for coupling the device to a charger and/or data connection. The internal battery may be charged when coupling the device to a connector; alternatively other electrical connectors and/or inductive charging may be used.

FIGS. 9A-9G illustrate an example of an apparatus (vaporizer apparatus) in which the cartridge 700 has been inserted completely into the vaporizer body 800. The resulting device is small, lightweight, hand-held and may be safely stored in a pocket, purse, or the like.

In operation, the user may (once charged sufficiently), may activate the vaporizer by being drawing (inhaling) through the mouthpiece. The device may detect a draw (e.g., using a pressure sensor, flow sensors, or the like, including a sensor configured to detect a change in temperature or power applied to a heater element, e.g., anemometer detection) and may increase the power to a predetermined temperature preset. The power may be regulated by the controller by detecting the change in resistance of the heating coil and using the temperature coefficient of resistivity to determine the temperature. As described in greater detail below, the temperature determination and/or power applied may be optionally corrected in cases where there are different electrically conductive materials connecting the resistive heater to the power supply/power, in which the Seebeck effect may be an issue, using a sensing circuit to estimate and compensate for this potential source of inaccuracy.

In any of the apparatuses described herein, the temperature may be adjusted or selected by the user. As mentioned, in some variations the apparatus does not include an exterior control or user input, but still allows the user to select the temperature from among a plurality (e.g., two or more, three or more, etc.) of pre-set heating/vaporizing temperatures above 100° C. This may be achieved by allowing the user to coordinate (in time, e.g., within 60 seconds, within 50 seconds, within 40 seconds, within 45 seconds, within 40 seconds, within 30 seconds, within 20 seconds, within 10 seconds, between 1 second and 60 seconds, between 2 seconds and 60 seconds, between 3 seconds and 60 seconds, etc.) a pair of distinct inputs that are based detection of inputs that are internal to the apparatus (e.g., not from controls on the surface of the apparatus), such detection an accelerometer input (e.g., tapping, such as one or more, e.g. 3 or more, taps, rotations of the device in the long axis, etc.) within a predefined time after removing the cartridge and/or inserting the cartridge. For example, the apparatus may enter into a temperature selection mode to allow a user to select the temperature by removing the cartridge after shaking the apparatus (e.g., for 1 or more seconds, e.g., 2 or more seconds, etc.). Once in a temperature selection mode, the user may select from among a number (e.g., 4) or pre-set temperatures by tapping the housing of the device to cycle through the pre-set temperatures, which may be displayed on an output (e.g., LED, monitor, LCD, etc.) on the apparatus.

Any other input on the device that is not (or not connected to) a button, and particularly an external button, may be used in a predetermined activation sequence (e.g., pattern of taps detected by the accelerometer, insertion/removal of cartridge, etc.) or in a set of sequential independent actuations. For example, the apparatus may enter into a temperature selection mode after removing and inserting a cartridge three times in quick successions (e.g., within 5 seconds of each step). In any of the variations described herein, merely shaking the apparatus may display information about the status of the device (e.g., the charge) using the output; the additional non-button input (e.g., removing the cartridge and/or inserting the cartridge) within the predetermined time may then allow the operating temperature to be selected.

In some variations, the apparatus includes multiple (e.g., 4) presets, and an optional additional preset (e.g., 5th preset or more) that may be user-settable. Alternatively or additionally, an external controller (smartphone, pad, computer, etc.) in may communicate with the apparatus to allow setting and/or selecting the operating temperature.

In on example, the apparatus may be operated to allow the user to select the operating temp (set mode) by shaking the device with a cartridge inserted. In some variations this may then change the display (e.g., multi-colored LEDs on the surface of the device), for example, displaying battery life using the multiple LEDs arranged (e.g., in an X pattern 897, see, e.g., FIG. 8C). While in this state, removing cartridge enters temp set mode. The device automatically cycles through the 4 (+1 or more, when user defined) presets. The user may then choose one by reinserting the pod at appropriate time. In some variations, the preset temperatures are: 270° C., 320° C., 370° C., 420° C. In some variations the user may modify or include an additional preset within a temp range around each preset, e.g.: within an operational range of between 270-420° C.

As mentioned above, any of the apparatuses described herein may be operated with an external processor to receive input and/or output to control operation of the device. For example, the vaporizer apparatus may be operated with an application software ("app") that allows control of the temperature or other functional setting and/or allows storage, display and/or transmission of operational and/or use information, including dose information. As described herein, an approximate estimate for dose may be determined based on the power applied to the heater (resistive coil) during inhalation (over time), e.g., power applied to coil multiplied by time of draw. This approximate 'dose' estimate may be accumulated over the use of a particular cartridge (e.g., once a cartridge is inserted, it may be accumulated and/or displayed until the cartridge is removed, roughly amounting to a "session" with that cartridge).

Figure 22:
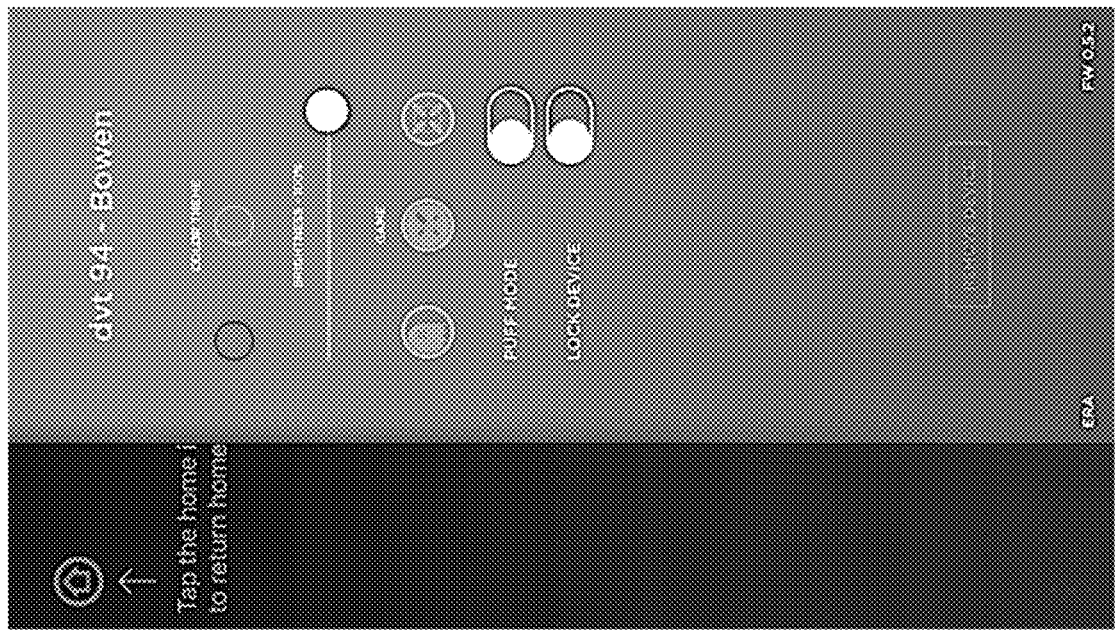
FIG. 22 is another example of a US for interacting with an apparatus as described herein.
Figure 21:
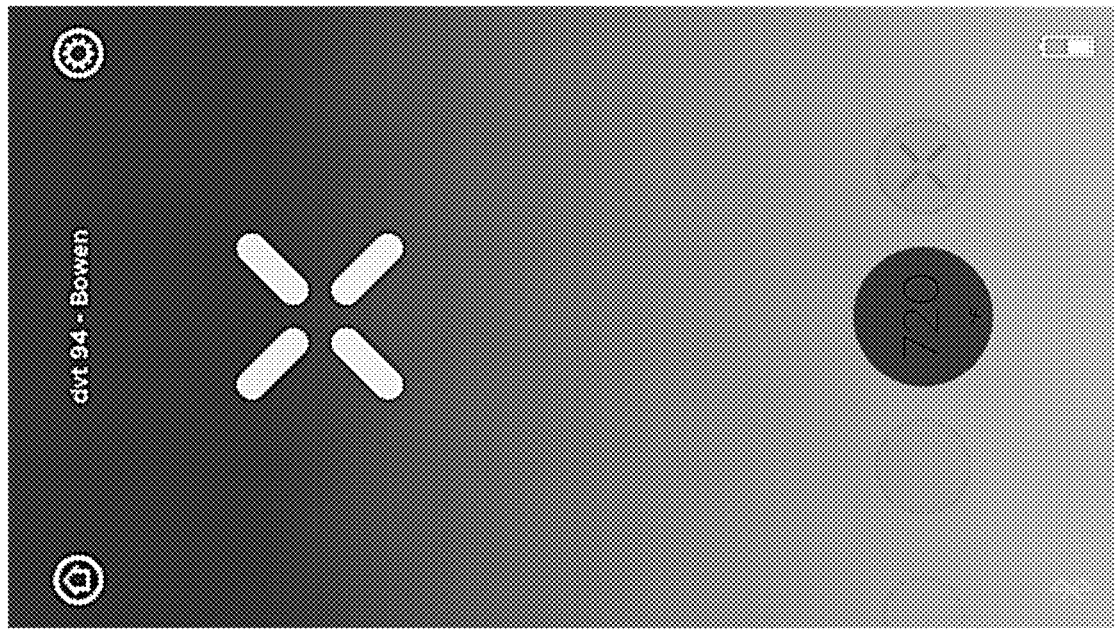
FIG. 21 is one example of a user interface (UI) for interacting with the apparatuses described herein using an external controller (e.g., smartphone, pad, etc.)

For example, FIGS. 21 and 22 illustrate exemplary user interfaces for an application software that allows the user to set and or adjust the pre-set temperatures of the apparatus. In FIG. 21, the user may select the per-set temperature. FIG. 22 illustrates the use of the app to control the appearance and activity of the apparatus. For example, the user may lock/unlock the apparatus, and track usage (e.g., by does estimation).

In any of the apparatuses described herein the apparatus may allow the user to play one or more interactive "games" with the device. For example, any of these apparatuses may include an entertainment mode that may be entered by manipulating the device (e.g., by tapping, shaking, rotating, puffing in a predetermined pattern, etc.). In general, the entertainment mode may include one or more presentations (e.g., LED light displays, tones/music, patterns of vibrations, or combinations of these) and/or games. The device may be configured to allow selection of the presentation states or game states (games) to be played, or it may randomly select one. In general the games may be interactive, allowing the user to provide input, e.g., via the one or more inputs, such as movement of the device, via motions sensing, touching the device, via a button and/or capacitive sensor (e.g., lip sensing, etc.), puff/airflow sensing, inserting and/or removing the cartridge, etc.

For example, the entertainment mode may include a game such as a pattern-following game, wherein the device presents an output (e.g., one or more LEDS illuminated in a pattern and/or color), and the device (e.g. controller) may determine if a response entered by the user on the input correlates with a predetermined response. In general, the same controller used to control the heater may be used to control the entertainment mode including the games. Alternatively a separate controller may be used, and may communicate with the controller controlling the heater.

The one or more games may include a memory game. For example, in a memory game the device may presents an output sequence and determines if a sequence of responses entered by the user on the input correlates with a predetermined sequence of responses. The one or more games may include a triggered output game wherein the device presents an output in response to a predetermined user input. For example, the device may illuminate a series differently positioned and/or colored LEDs based on the angle or movement that the user holds the device.

The one or more games may include a chance type game, wherein the device is configured to display a random pattern of one or more of colors, tones or vibrations, in response to a predetermined user input. The entertainment mode may include a display game wherein the output comprises a plurality of LEDs and wherein the device is configured to cycle the LEDs through a predetermined sequence of colors in response to a predetermined user input. The entertainment mode may include a tone game wherein the output comprises a plurality of tones and wherein the device is configured to play a predetermined sequence of tones in response to a predetermined user input.

As mentioned, the device may be configured to be toggled between the normal mode and the entertainment mode by applying one or more predetermined user manipulations to the input. For example, the device may be rotated. In some variations, the device input comprises an accelerometer, and the device may be configured to be toggled between the normal mode and the entertainment mode by rolling or rotating the device (e.g., three or more times) in one or more directions.

In addition to or alternative to the games, the entertainment mode may include an entertainment output (display) that is triggered upon entering into the entertainment mode. For example, as mentioned, the entertainment output may include one or more of: a display of a plurality of colors and/or patterns on the output, a tone or series of tones, a vibration or series of vibrations.

Leak Prevention

Any of the apparatuses described herein may be configured to prevent or reduce leakage of the vaporizable material. As mentioned, leaking an oil-based (and particularly cannabinoid oils) is particularly troublesome in a vaporizer because the vaporizable material may dry as a sticky, tarry substance that is both messy and may disrupt operation of the apparatus, particular the reusable (e.g., vaporizer base) portion.

For example, any of the apparatuses described herein may include one or more absorbent pads or members that are oriented to prevent leakage without disrupting the airflow or formation of vapor. In general, moisture and particles from the vapor can be deposited on a filter pad that is off-axis relative to the vapor path. The vaporization device may be a handheld vaporization device.

As described above, any of the vaporization apparatuses (device and systems) may comprise a heating element, including a resistive heating element. The heating element may heat the material such that the temperature of the material increases. Vapor may be generated as a result of heating the material.

In some cases, a vaporization device may have an "atomizer" or "cartomizer" configured to heat an aerosol forming solution (e.g., vaporizable material). The vaporizable material may be heated to a sufficient temperature such that it may vaporize (e.g., between 200° C. and 500° C., e.g., between 250-450° C., between 270-420° C., etc.). The apparatus or method may include one or more pre-set vaporization temperatures and the apparatus or method may control (via controller including feedback logic) the temperature to a predetermined and/or selected temperature.

An atomizer may comprise a small heating element configured to heat and/or vaporize at least a portion of the vaporizable material and a wicking material that may draw a liquid vaporizable material into the atomizer (e.g., heater). When the apparatus includes a wicking material, the wicking material may comprise silica fibers, cotton, ceramic, hemp, stainless steel mesh, and/or rope cables. The wicking material may be configured to draw the liquid vaporizable material in to the atomizer without a pump or other mechanical moving part. A resistance wire may be wrapped around the wicking material and then connected to a positive and negative pole of a current source (e.g., energy source). The resistance wire may be a coil. When the resistance wire is activated, the resistance wire (or coil) may have a temperature increase as a result of the current flowing through the resistive wire to generate heat. The heat may be transferred to at least a portion of the vaporizable material through conductive, convective, and/or radiative heat transfer such that at least a portion of the vaporizable material vaporizes.

Alternatively or in addition to the atomizer, the vaporization device may be configured as a "cartomizer" to generate an aerosol from the vaporizable material for inhalation by the user. The cartomizer may comprise a cartridge and an atomizer. The cartomizer may comprise a heating element surrounded by a liquid-soaked poly-foam that acts as holder for the vaporizable material (e.g., the liquid). The cartomizer may be reusable, rebuildable, refillable, and/or disposable. The cartomizer may be used with a tank for extra storage of a vaporizable material.

Air may be drawn into the vaporization device to carry the vaporized aerosol away from the heating element, where it then cools and condenses to form liquid particles suspended in air, which may then be drawn out of the mouthpiece by the user. For example, any of the apparatuses described herein may include a draw channel or passage. The draw channel may be in fluid communication with the heater so that vapor formed by the heater passes into the draw channel, which is also in fluid communication with the mouthpiece, which may be integrated with the device (including a cartridge).

One or more aspects of the vaporization device may be designed and/or controlled in order to deliver a vapor with one or more specified properties to the user. For example, aspects of the vaporization device that may be designed and/or controlled to deliver the vapor with specified properties may comprise the heating temperature, heating mechanism, device air inlets, internal volume of the device, and/or composition of the material.

Energy may be required to operate the heating element. The energy may be derived from a battery in electrical communication with the heating element. Alternatively, a chemical reaction (e.g., combustion or other exothermic reaction) may provide energy to the heating element.

The term "aerosol" may generally refer to a colloid of fine solid particles or liquid droplets in air or another gas. In general, the aerosols described herein are liquid aerosols of primarily (e.g., >80%, >85%, >90%, >95%) liquid particles in air. The liquid or solid particles in an aerosol may have varying diameters of average mass that may range from monodisperse aerosols, producible in the laboratory, and containing particles of uniform size, to polydisperse colloidal systems, exhibiting a range of particle sizes. As the sizes of these particles become larger, they have a greater settling speed which causes them to settle out of the aerosol faster, making the appearance of the aerosol less dense and to shorten the time in which the aerosol will linger in air. Interestingly, an aerosol with smaller particles will appear thicker or denser because it has more particles. Particle number has a much bigger impact on light scattering than particle size (at least for the considered ranges of particle size), thus allowing for a vapor cloud with many more smaller particles to appear denser than a cloud having fewer, but larger particle sizes.

A vapor may generally refer to a substance in the gas phase at a temperature lower than its critical point. As used herein, a vapor may include a liquid aerosol. For convenience the term vapor and aerosol, which may generally refer to liquid aerosols, may be used interchangeably herein, as is common in the art of electronic vaporization devices.

The methods and apparatuses described herein have a wide range of applications for inhalation of an active substance, such as botanicals, pharmaceuticals, nutraceuticals, or any other substance for inhalation to provide a benefit or sensation to an end user. In some embodiments, the devices described herein include a tank having a liquid containing an active ingredient, such as nicotine, *cannabis*, or a cannabinoid.

The term "*cannabis*" refers to plants of the genus *Cannabis* and loose-leaf products or extracts thereof. As mentioned above, the term "cannabinoid" refers to plant based or synthetic chemical compounds capable of acting on cannabinoid receptors and inducing a biological effect. Cannabinoids include acids, salts, and bioactive stereo isomers. Exemplary cannabinoids include tetrahydrocannabinol (THC), cannabigerolic acid (CBGA), cannabigerol (CBG), tetrahydrocannabinolic acid (THCA), cannabichromene (CBC), cannabicyclol (CBL), cannabivarin (CBV), cannabichromevarin (CBCV), cannabigerovarin (CBGV), cannabigerol Monomethyl Ether (CBGM), delta-8-tetrahydrocannabinol (D8THC), delta-9-tetrahydrocannabinol (D9THC), tetrahydrocannabivarin (THCV), cannabinolic acid (CBNA), Cannabinol (CBN), cannabidiolic acid (CBDA), Cannabidivaric acid (CBDVA), cannabidiol (CBD), cannabichromenic acid (CBCA), Cannabichromene (CBC), or cannabicyclolic acid (CBLA) and/or any salt or stereo isomer of the above.

The devices described herein for generating an inhalable aerosol may include a body having a battery, a cartridge or tank including or configured to include the vaporizable material, at least input (e.g., in some variations without any input on an outer surface of the apparatus, e.g., "button less"), and circuitry for controlling the device.

Figure 2:
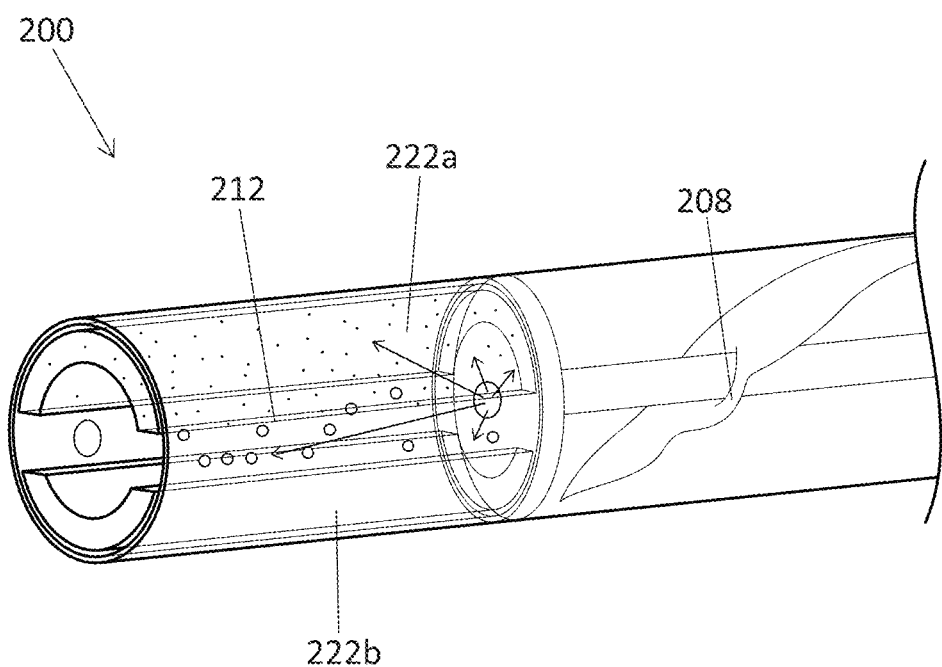

An exemplary vaporization device 200 is shown in FIGS. 1 and 2. The vaporization device 200 includes two filter pads 222a,b. The filter pads 222a,b are positioned off of the central axis of the air path 212. As the vapor travels down the air tube 208 and begins to return to liquid state, both condensation and particle aggregation will occur. As the vapor exits the air tube 208 into the air path 212, the moisture (see FIG. 1) and larger particles (see FIG. 2) can filter onto the pads 222a,b (i.e., via gravity) without interfering with the user's draw on the device.

The one or more pads for use with any of the embodiments described herein (including pads 222a,b) can be made of an absorbent material. The absorbent material can both wick moisture quickly and allow it to disperse quickly therethrough. Thus, the absorbent material can be hydrophilic. Exemplary materials include cotton, e.g., a nonwoven cotton lintner paper, felt, cellulose, or hydrophilic polymers. Further, the one or more pads can be curved, as shown in FIGS. 1 and 2 or can be substantially flat panels. In some embodiments, the one or more pads can each be made of two or more thin sheets of layered material.

The one or more pads can be positioned within or proximate to the mouthpiece so as to capture moisture just prior to inhalation by the user. Further, in some embodiments, as shown in FIGS. 1 and 2, the one or more pads can be pushed up against the interior surface of the vaporizer so as to minimize interference with other components of the vaporizer. In other embodiments, the one or more pads can be pulled away from the interior walls so as to maximize the surface area available for moisture absorption. The pads can be rectangular, circular, ovoid, triangular, square, or other shape. The shape and size of the pads can be chosen so as to minimize interference with the air path while maximizing moisture and particle collection.

Figure 3A:
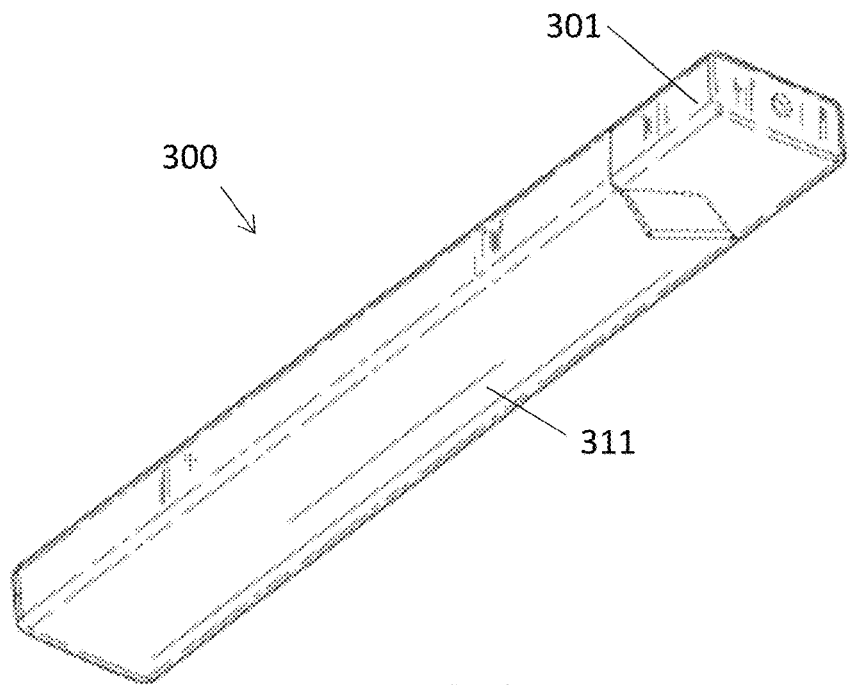
FIGS. 3A and 3B show a vaporization device with a pair of filter pads that are off-axis relative to the airflow path of the device.
Figure 3B:
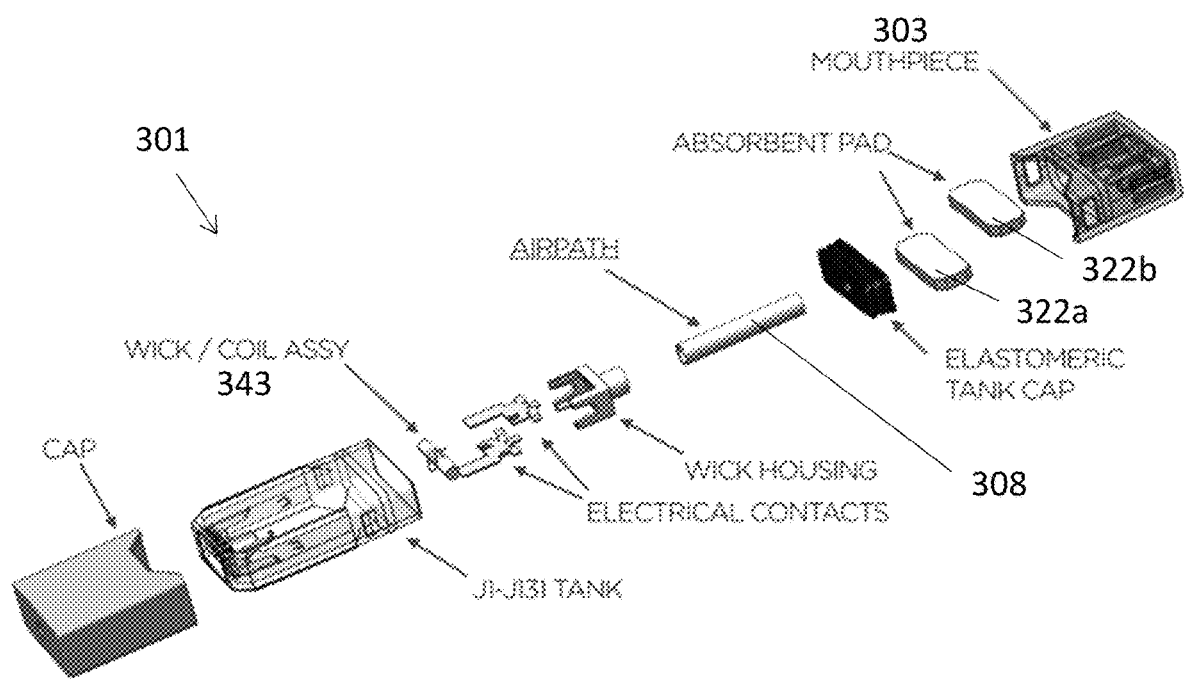

Another exemplary vaporizer 300 utilizing moisture deposition pads 322a,b is shown in FIGS. 3A and 3B. The vaporizer 300 includes a cartridge 301 that is attachable to a reusable component 300 (which can include the electronics to power the device, etc.). As shown in FIGS. 3A and 3B, the cartridge 301 can include a tank 302, a heater assembly 343, an air tube 308, and a mouthpiece 303. The pads 322a,b can be rectangular, flat, and positioned in parallel within the mouthpiece 303 on either side of the air tube 308 (i.e., off-axis with the air tube 308). The vaporizer 300 can further include any of the features described in U.S. application Ser. No. 15/053,927, titled "VAPORIZATION DEVICE SYSTEMS AND METHODS," filed on Feb. 25, 2016, Publication No. US 2016-0174611 A1, the entirety of which is incorporated by reference herein.

Another exemplary vaporizer 400 that can utilize one or more pads is shown in FIGS. 4A-6B. As shown in FIGS. 4A and 4B, the vaporizer 400 includes a reusable component 411 and a cartridge 401. The diameter of device 400 is greater than the width (e.g., greater than 1.2×, 1.3×, 1.4×, 1.5×, 1.6×, 1.7×, 1.8× 1.9×, etc.), making the device have a substantially long and flat appearance and feel.

Referring to FIGS. 5A and 5B, the reusable component 411 includes a shell 431, which can include the electronics for operating the vaporizer. Further, the reusable component 411 can include a visual indicator 421, such as an LED, for signaling the operating status of the vaporizer 400. The distal end of the reusable component 411 (shown in FIG. 5F) includes a charging element 433 configured for charging the device. Further, the proximal end of the device (FIG. 5E) includes contacts 435 for maintaining an electrical connection with the cartridge 401.

The cartridge 401 is shown in FIGS. 6A-6D. As best shown in the exploded view of FIG. 6D the cartridge 401 includes a tank 441 configured to hold a liquid vaporizable material therein, a heater (e.g. a wick and coil assembly) 443 configured to heat the vaporizable material in the tank 441, and an air tube 408 extending from the tank to a mouthpiece 403. Contacts 535 are configured to connect with contacts 435 on the reusable component 411 to provide power to activate the wick and coil assembly 443. At the distal end of the cartridge the walls of the elongate and flattened tubular body 441 and a bottom cover piece 691 form an overflow leak chamber 699, which is shown with a pair of absorbent pads 495a,b are positioned along the long walls (along the diameter) of the overflow leak chamber. An option felt cover 693 may be included (also acting as an absorbent member).

As shown in FIGS. 4A-5D, the device 400 further includes openings, configured as air inlets 762a,b, on the side of the shell 431. The air inlets are proximate to openings (air inlets) 662a,b on the distal end of the cartridge 401 (see FIGS. 6A and 6B) opening into the overflow leak chamber (not visible). Referring to FIG. 11A (which is a cross-section of the device 400 at the center), the air flow path 777 from inlets 762a,b to inlets 662a,b, extends through the tube 408 until it reaches the stop 433 (see FIG. 12) and then divides into two separate paths that extend along the inner surface of the mouthpiece 402 (between the pads 422a,b) and out through the outlets of the mouthpiece 403.

As shown in FIGS. 6D and 12-14, parallel absorbent pads 422a,b can be positioned within the mouthpiece 403. The absorbent pads 422a,b are rectangular and parallel with one another. The absorbent pads 422a,b are positioned substantially parallel to the flat side of the device 400 (parallel with the plane of the length 1 and width w in FIG. 4A) and parallel with one another. In some embodiments, the pads 422a,b can be biased fully against the inside walls of the mouthpiece 403 so as to easily capture liquid that rolls along the walls. A distance between the two pads 422a,b can be, for example, between 3 and 6 mm, such as between 4 and 5 mm, e.g., approximately 4.8 mm. The gap between the absorbent pads 422a,b advantageously prevents the pads from interfering with the air flow path when a user draws on the mouthpiece 403.

Figure 6D:
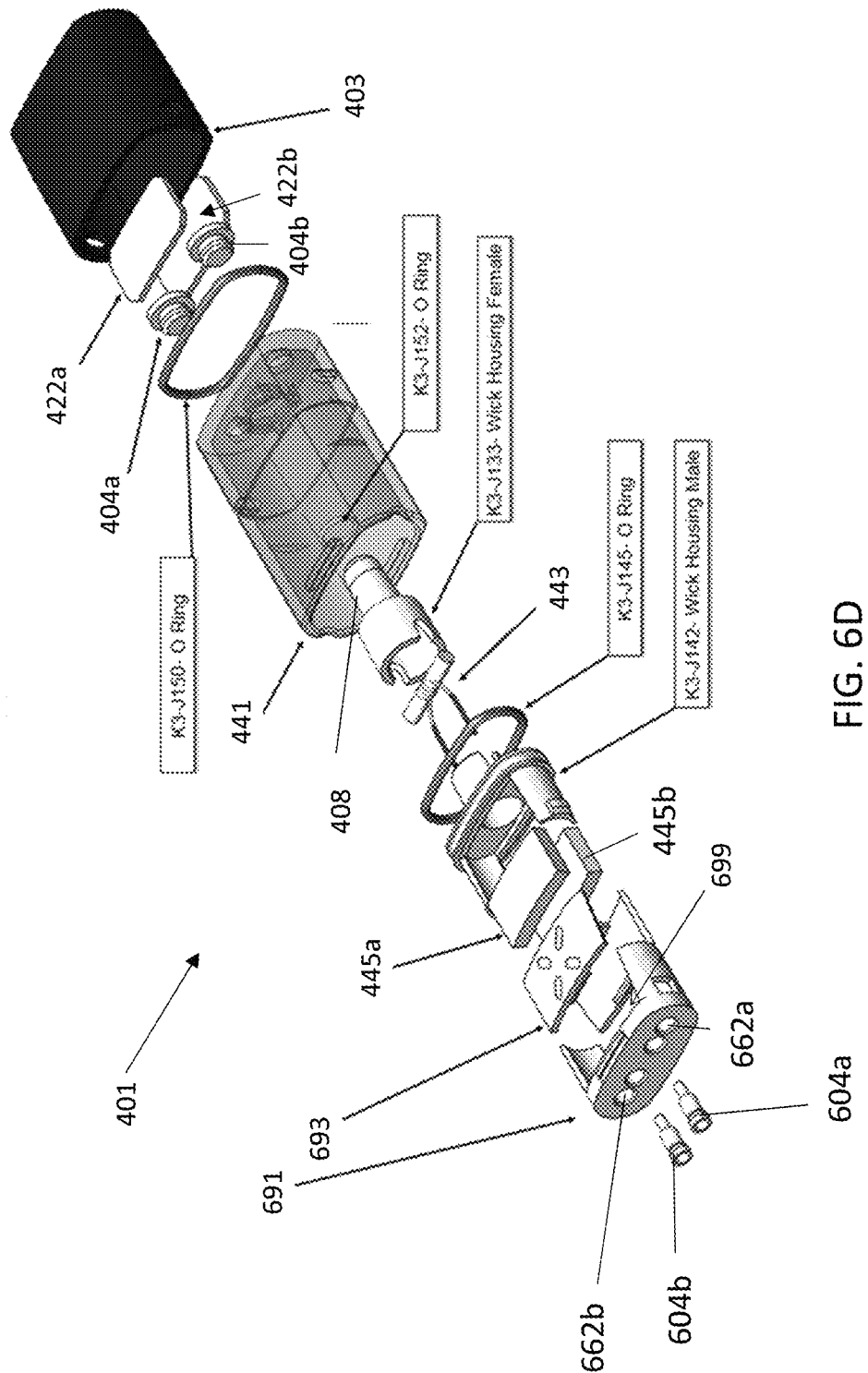
Figure 12:
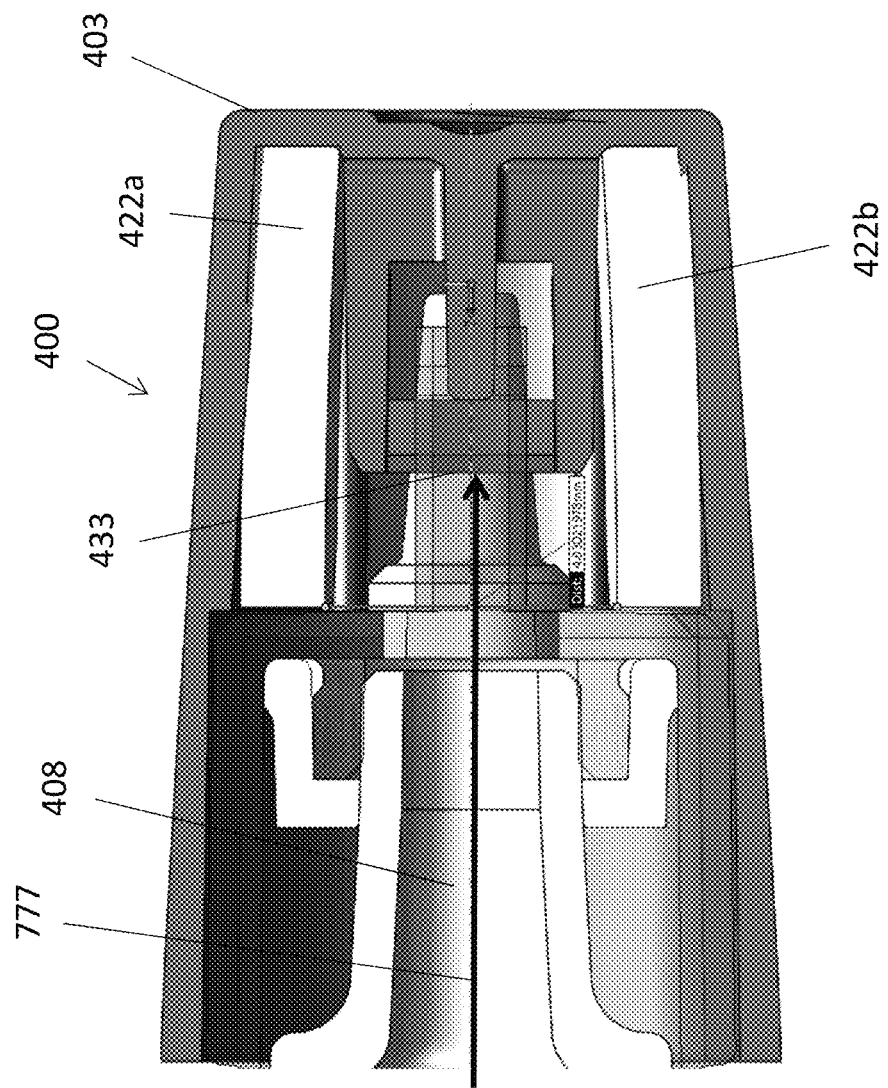
FIG. 12 is an enlarged view of a section through a midline of the proximal (top) region of a cartridge (as shown by dashed line 12-12' in FIG. 9A), showing the air path from the vaporization chamber to the mouthpiece openings.
Figure 13:
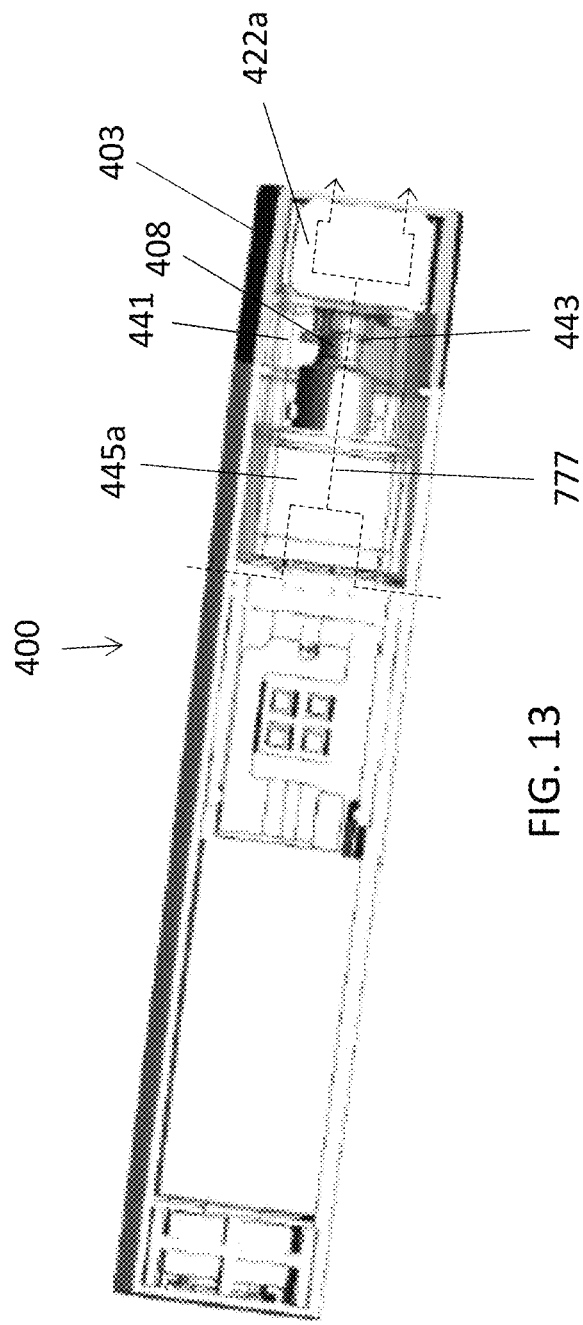
FIG. 13 is a section through the midline of a vaporizer apparatus (including a vaporizer base into which a vaporizer cartridge has been coupled), showing the air path during inhalation (puffing, drawing, etc.).
Figure 14:
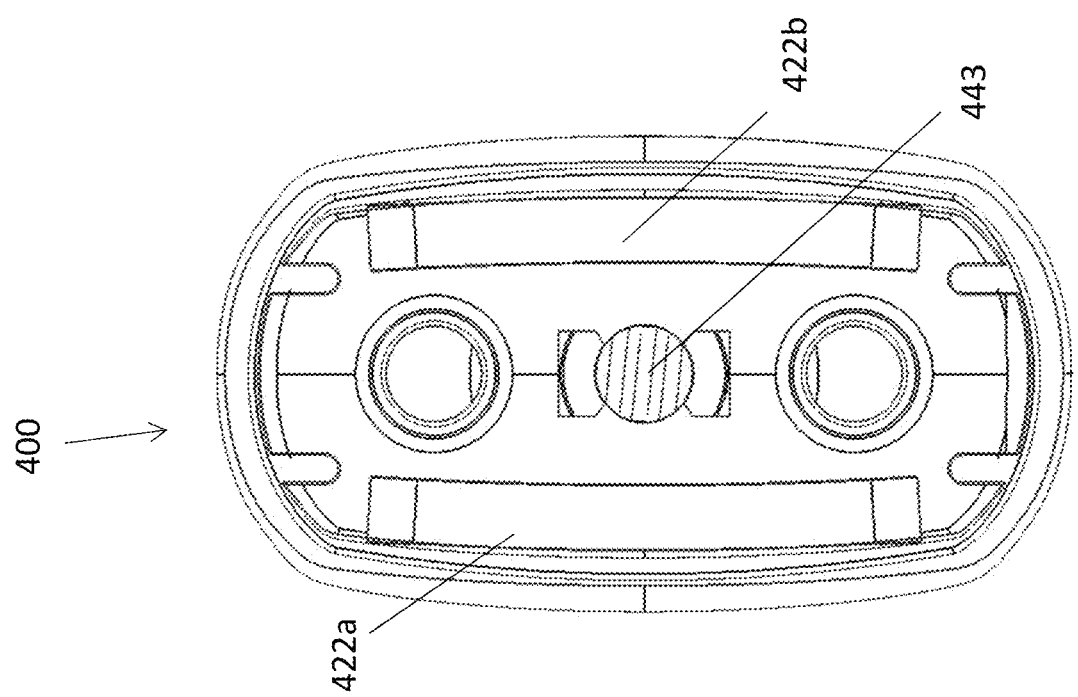
FIG. 14 show a section through a cartridge, just beneath the mouthpiece (as shown by dashed line 14'-14' in FIG. 9B) showing the arrangement of the distal pair of absorbent pads offset from the airflow path.

Further, as shown in FIGS. 6D, 12 and 13 in some embodiments, over-flow pads 445a,b are positioned proximate to the tank 441, i.e., within an overflow leak chamber below the tank, to absorb liquid that may leak out of the tank 441 during use. The over-flow pads 445a,b can be similarly placed parallel to one another and/or against the sides of the shell 431 as described above with respect to pads 422a,b.

FIG. 13 (which is a cross-section of the device 400 through the pads 422a,b and 445a,b) shows the air flow path 777 in dotted lines relative to the placement of the pads 442a,b and 445a,b. The air path 777 extends alongside all of the pads 422a,b without extending therethrough. That is, the pads 422a,b and 445a,b extend off-axis relative to the air path 777 and do not interfere with user draw. However, the pads 422a,b and 445a,b are positioned so that the air path 777 travels along, besides, and/or in contact with the pads 422a,b and 445a,b for an extended period of time so as to allow maximum absorption of liquid.

In use (i.e., when the user draws on the device), the device 400 can be held horizontally with the width, w, in the vertical direction and the diameter, d, in the horizontal direction. As such, at least one of the pads 422a,b and/or 445a,b will be substantially horizontal while the user draws on the device, ensuring that gravity will pull any moisture or particles down onto the lower pad 422a,b and/or 445a,b. Further, having two pads 422a,b and/or 445a,b advantageously ensures that moisture will be caught whether the user holds the device with pad 422a or 445a on top or 422b or 445b on top. This can both prevent interference with the electronics of the device and prevent the user from getting any liquid from the tank in his or her mouth when drawing on the device.

Referring to FIGS. 15A-15D, exemplary device 800 is similar to device 400 (similar reference numbers are therefore used) except that it includes a single plug 888 in the proximal section of the cartridge 801 (i.e., as opposed to the two tank seals 604a,b shown in FIG. 6D). The plug 888 is configured to simultaneously seal both outlets of the mouthpiece 403 while also sealing around the tube 408.

Although sets of absorbent pads are shown and described with respect to the embodiments herein, only a single off-axis (i.e. "off air path") pad can be used in each location. Likewise, more than two (e.g., 3, 4, 5, or more) off-axis pads, such as strips of absorbent material, may be used. Similarly, only a single set of pads can be used.

In some embodiments, the absorbent pads can be located only in the cartridge area (i.e., in the disposable portion). In other embodiments, additional absorbent pads can also be used in the reusable portion of the device.

The wick for use with any of the embodiments herein can be large to handle higher viscosity liquids (e.g., liquids with cannabinoids). For example, the wick can be greater than 1.5 mm in diameter, such as approximately 2 mm in diameter.

Referring to FIG. 16, in some embodiments, the openings (also referred to as air inlets) 962a,b to the cartridge 901 can include a protective annular ring 992a,b or seal therearound that extends away from the inner wall of the cartridge 901. This ring can help prevent any spilled liquid from splashing into the inlets 962a,b. This ring may be lip or ridge projecting into the overflow leak chamber, as shown in FIG. 16.

Referring still to FIG. 16, in some embodiments, the contacts 935 of the reusable portion 911 of the device 900 can be pin contacts while the contacts 1035 of the cartridge 901 can be annular contacts or pin receptacles configured to mate with the pins. Further, in some embodiments, pin receptacles 1035 can include spring-loaded wiping mechanisms on the inner diameter thereof. The spring-loaded wiping mechanisms can be configured to wipe the pins as they pass therethrough. As a result, any vapor residue on the pins can be removed to maintain the proper electrical connection there between.

Power and Temperature Control

In any of the apparatuses described herein, the vaporizer apparatus may be controlled so that the temperature used to vaporize the vaporizable material is maintained within a preset range (e.g., one or more preset temperatures as discussed above, within +/−a few degrees (e.g., +/−3° C., 2° C., 1° C., 0.5° C., etc.). In general, the microcontroller may control the temperature of the resistive heater (e.g., resistive coil, etc.) based on a change in resistance due to temperature (e.g., TCR). For example, a heater may be any appropriate resistive heater, such as a resistive coil. The heater is typically coupled to the heater controller via two or more connectors (electrically conductive wires or lines) so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater.

For example, any of the apparatuses described herein may include logic for determining the temperature of the heater based on the TCR of the heating element (resistive coil), based on sensed resistance of the coil. The resistance of the heater (e.g., a resistive heater) may be measured ($R_{heater}$) and the controller may use the known properties of the heater (e.g., the temperature coefficient of resistance) for the heater to determine the temperature of the heater. For example, the resistance of the heater may be detected by a detection circuit connected at the electrical contacts that connect to the cartridge, and this resistance compared to a target resistance, which is typically the resistance of the resistive heater at the target temperature. In some cases this resistance may be estimated from the resistance of the resistive hearing element at ambient temperature (baseline).

In some variations, a reference resistor ($R_{reference}$) may be used to set the target resistance. The ratio of the heater resistance to the reference resistance ($R_{heater}/R_{reference}$) is linearly related to the temperature (above room temp) of the heater, and may be directly converted to a calibrated temperature. For example, a change in temperature of the heater relative to room temperature may be calculated using an expression such as $(R_{heater}/R_{reference}-1)*(1/TCR)$, where TCR is the temperature coefficient of resistivity for the heater. In one example, TCR for a particular device heater is 0.00014/° C. In determining the partial doses and doses described herein, the temperature value used (e.g., the temperature of the vaporizable material during a dose interval, $T_i$, described in more detail below) may refer to the unit less resistive ratio (e.g., $R_{heater}/R_{reference}$) or it may refer to the normalized/corrected temperature (e.g., in ° C.).

When controlling a vaporization device by comparing a measure resistance of a resistive heater to a target resistance, the target resistance may be initially calculated and may be factory preset and/or calibrated by a user-initiated event. For example, the target resistance of the resistive heater during operation of the apparatus may be set by the percent change in baseline resistance plus the baseline resistance of the resistive heater, as will be described in more detail below. As mentioned, the resistance of the heating element at ambient is the baseline resistance. For example, the target resistance may be based on the resistance of the resistive heater at an ambient temperature and a target change in temperature of the resistive heater.

As mentioned above, the target resistance of the resistive heater may be based on a target heating element temperature. Any of the apparatuses and methods for using them herein may include determining the target resistance of the resistive heater based on a resistance of the resistive heater at ambient temperature and a percent change in a resistance of the resistive heater at an ambient temperature.

In any of the methods and apparatuses described herein, the resistance of the resistive heater may be measured (using a resistive measurement circuit) and compared to a target resistance by using a voltage divider. Alternatively or additionally any of the methods and apparatuses described herein may compare a measured resistance of the resistive heater to a target resistance using a Wheatstone bridge and thereby adjust the power to increase/decrease the applied power based on this comparison.

In any of the variations described herein, adjusting the applied power to the resistive heater may comprise comparing the resistance (actual resistance) of the resistive heater to a target resistance using a voltage divider, Wheatstone bridge, amplified Wheatstone bridge, or RC charge time circuit.

Figure 15A:
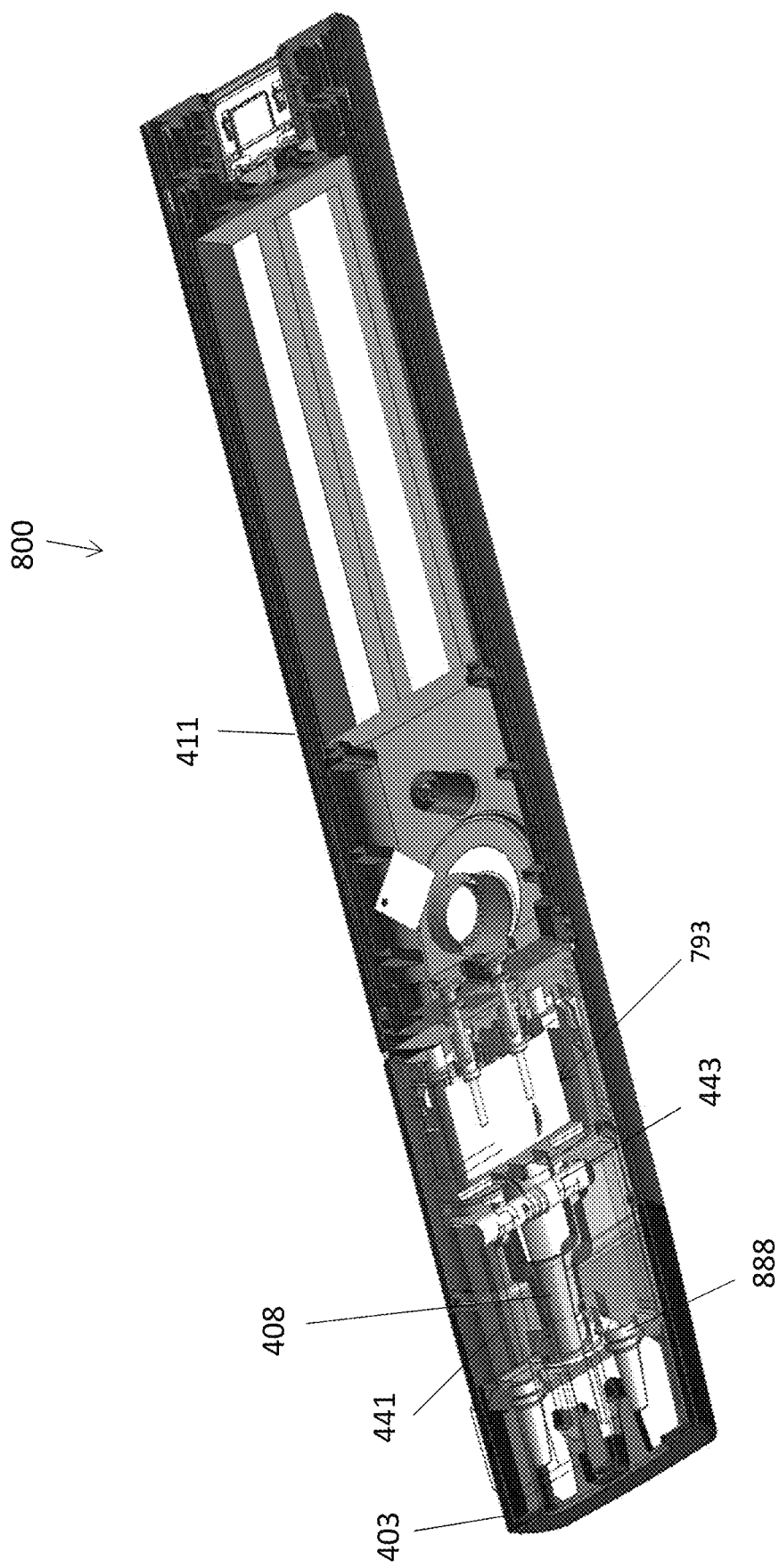
FIG. 15A is a section through the midline of an assembled vaporizer apparatus such as the one shown in FIG. 9A (through line 15A-15A').
Figure 15B:
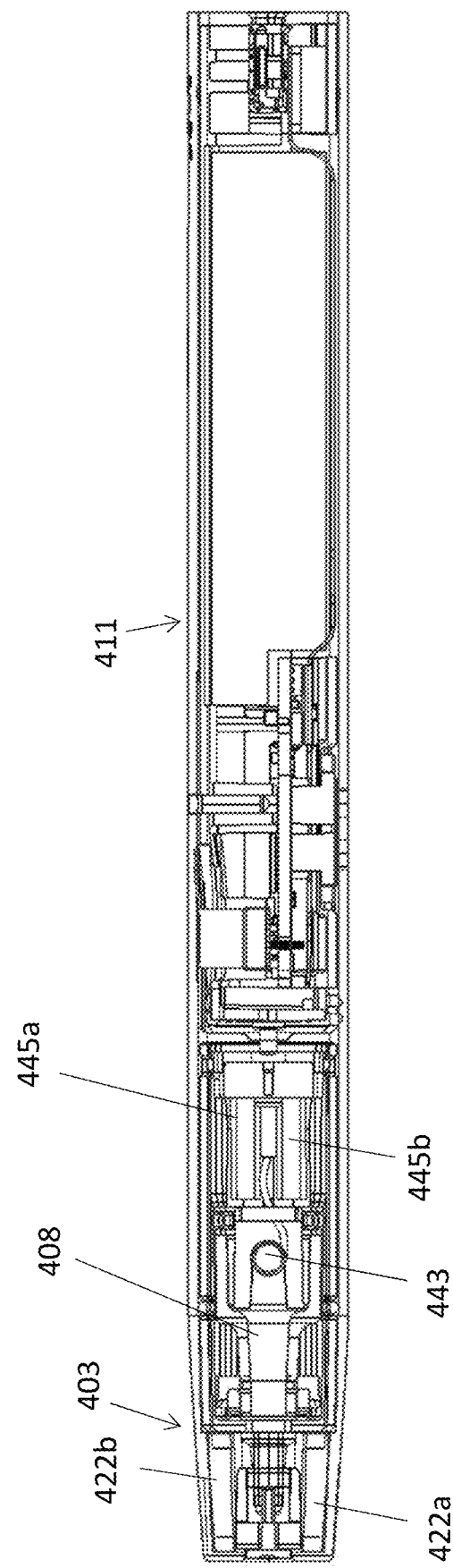
FIG. 15B is another section through an assembled vaporizer apparatus such as the one shown in FIG. 9A (through line 12-12').
Figure 15C:
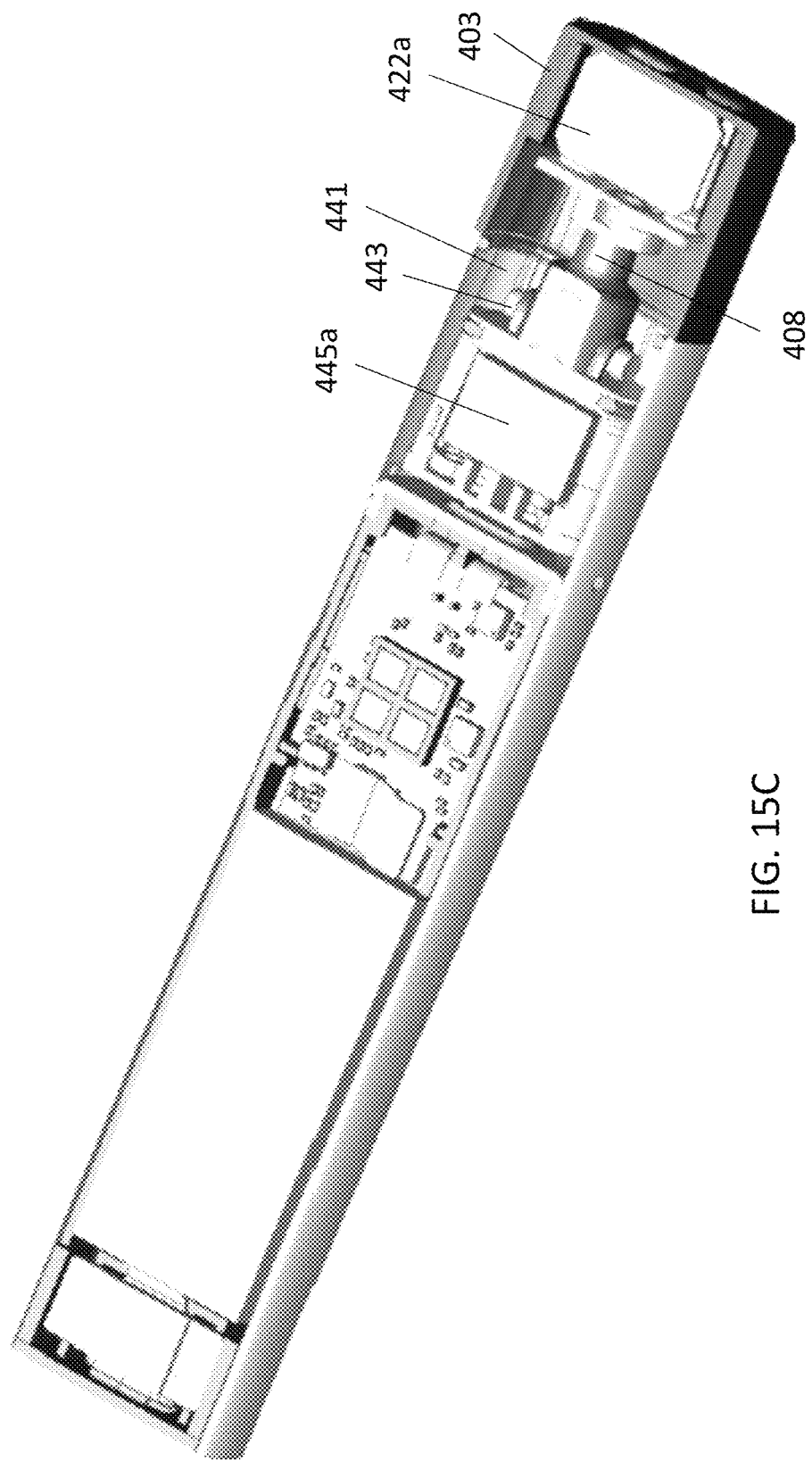
FIG. 15C shows another section through the assembled vaporizer apparatus (through line 15C-15C' in FIG. 9B).

When using resistance and/or power applied to determine the temperature of the apparatus and/or to control temperature for vaporization, the inventors have determined that there may be a surprising disparity between the actual temperature and that predetected or determined using resistance of the heater alone. This problem because particularly acute when the distance between the heating element (e.g. resistive coil) and the electrical input into the cartridge (the power contacts from the vaporizer base) is longer, or there is a change in the conductive material between the heater and the contacts, as shown in FIG. 15A. Where there is a change in the conductive material between the contacts, the electrical wiring and the resistive coil, thermoelectric effects arising due to this change in electrical characteristics (resistance) may give rise to inaccuracies when determining the power applied.

In the exemplary cartridges described above, the heating coil is connected to the electrical contacts by extension wires 1054, 1054' (see, e.g., FIG. 10B). Because the extension wires are different materials, a voltage (EMF) may be generated at the junction between the different electrical conductors when there is a temperature gradient. This thermoelectric effect may be referred to as the Seebeck effect, and may generate a voltage that is based on the material properties of the different conductors. In the variations described above, although the heating coil, extensions and wick are nearly symmetric, during normal usage there may be uneven temperatures across the three, developing a temperature gradient. This may result in an uneven voltage being generated; this disparity may then lead to inaccuracies in controlling the heater (applied power) and/or estimation of the temperature.

Although at any particular time, the effect may be relatively minor (and therefore overlooked), the cumulative effect may lead to dramatic reductions in accuracy and temperature control; other systems may attempt to avoid this problem by modifying the resistance of the material used for the resistive heater, requiring a larger power; although this may reduce the overall contribution of the offset EMF voltage due to the thermoelectric property mismatch, it also requires a larger wattage and therefore battery (and resulting power) be applied.

Instead, any of the apparatuses described herein may include a precision resistance measurement circuit to track resistance of the heating element (e.g., a coil made from resistive heating alloy wire) when not heating and heating to control the temperature of the coil based on changes in coil resistance from room temperature to vaporization temperatures, as discussed above. For example, in some variations, the measurement circuit is an amplified Wheatstone bridge where the heating element (when connected) is one half of one of the two voltage dividers in the Wheatstone bridge and the two divider voltages are inputs to a differential op amp circuit. This control circuit may be modified as described herein to account for the mismatch in thermoelectric properties leading to the offset voltage.

Currently known resistance measurement systems typically use a two-terminal sensing or four-terminal sensing circuit, and are prone to measurement error when the load to be measured is also a voltage source or has an additional unknown voltage applied to it. As just mentioned above, in vaporizers that use resistive heating elements (often coils), extension leads are often used to route power to the heating element with minimal Joule heating and losses in the path between the heating element (where Joule heating is desired) and the voltage source (often a battery or power supply). For manufacturability, these extension leads are often the only connection between the device (or contacts that connect to the device) and the heating element, so measurement of the resistance of the heating element invariably includes the resistance of the extension leads and measurement error arising from the mismatched thermoelectric properties (Seebeck error). The heating element and extension leads (three conductors if considered individually) each have some temperature gradient along their lengths, and this temperature gradient generates an electromotive force (EMF, which is also a measureable voltage when the conductor is open circuit) in each conductor, which is $E_{emf}=-S\nabla T$, where S is the Seebeck coefficient of the conductor which depends heavily on the conductor material (but also on temperature of the conductor) and $\nabla T$ is the temperature gradient across the material. Because ideal materials for the heating element and extension leads often have different Seebeck coefficients, and since the temperatures at the two connection points between each extension lead and the heating element are likely to differ while heating (due to acceptable asymmetries in both heating element assembly and heat transferred from the heating element and extension leads that are expected in a mass-produced product), there will be a net EMF across the extensions and heating element (seen as one load in any vaporization system where one set of extension leads electrically connects the heating element to the device) which will skew the resistance measurement, making temperature control of the heating element using measured resistance impossible without correction for this effect. More generally, measured resistance of the heating element will be skewed by the mismatched thermoelectric properties (e.g., the Seebeck effect) whenever there is a temperature difference between and material transition at the two heating element terminals where contacts or extensions are connected.

Figure 17:
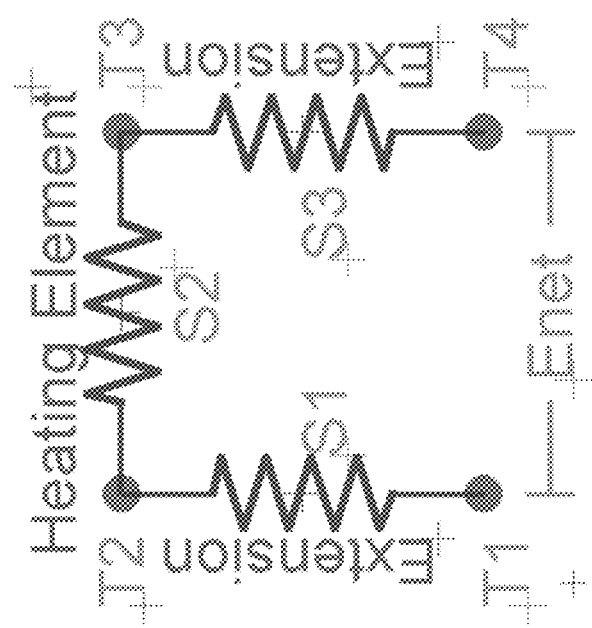
FIG. 17 is an electrical schematic of a heating element and connectors showing the Seebeck coefficients for a simplified model of the components of the heating circuit.

A simplified model of a heating element with two extension leads of the same material is shown in FIG. 17. In this example, the heating element and extension lead combination connects to the device at the open ends of the extension leads shown above, so the resistance measurement of the heating element is taken through the extension leads connecting to it. S1 and S3 are constant coefficients that depend on the material properties (Seebeck coefficients) of each of the two extension lead materials, and S2 is the Seebeck coefficient of the heating element. T1 and T4 are temperatures at the ends of the extensions that electrically connect to the vaporization device. T2 and T3 are temperatures of the connections between the extension leads and heating element (which may be welds, crimps, solder joints, or other electrical connections). The EMF, $E_{net}$ is expected to skew the resistance measurement if $E_{net}$ is non-zero. $E_{net}$ from the Seebeck effect is expected to be:

$$E_{net} = -S1(T2-T1) - S2(T3-T2) - S3(T4-T3).$$

To illustrate how temperature differences between T2 and T3 can create a non-zero $E_{net}$, consider a further simplified model where temperatures at the two open (as shown) ends of the conductive path are assumed to be the same and close to the device temperature (T1=T4), which is an acceptable simplification in systems like ours where extensions connect to electrical contacts with large thermal mass at T1 and T4. Seebeck coefficients for the two extensions are assumed to be the same since the two extension leads are of the same material (S1=S3). This reduces the above expression to:

$$E_{net} = (S2-S1)(T2-T3)$$

From the above expression, if S2 and S1 are not equal (heating element and extension leads have different Seebeck coefficients) and T2 and T3 are not equal (non-zero net temp gradient across the two points where heating element meets extensions), $E_{net}$ will not be zero, and it will skew the resistance measurement taken by the device. For comparison, if there are no extension leads, EMF for the heating element alone can be considered:

$$E_{net} = S2(T2-T3)$$

When the heating element is connected directly to electrical contacts that are large thermal masses, it is expected (and can be measured) that T2 and T3 are very close and Seebeck effect introduces negligible error in resistance measurement. In other systems where extension leads are used, the Seebeck effect will skew measured resistance, making temperature control impossible when Seebeck effect is not corrected for.

Additionally, some systems without extension leads may still see a temperature difference between T2 and T3 depending on the device and heating element assembly. If this temperature difference is significant, this effect will have to be corrected for if accurate resistance measurements is desired.

The simple model above with extension leads and heating element is provided to illustrate the source of heating element EMF. In most systems there will be additional material transitions and temperature gradients in each material in the resistance measurement path. As described below, a complete understanding or modeling of all material transitions and junction temperatures is not needed to correct for this effect. The heating element EMF (caused by the Seebeck effect) can simply be measured and used to correct for the error it introduces in resistance measurements.

In a vaporization devices that uses measured heating element resistance for temperature control of the heating element as described above, heating element EMF may also measure and used to control the power applied and/or estimates of temperature. The Seebeck effect may be observed to be the main contributor to heating element EMF and is the only known contributor to heating element EMF when no current (or constant current) has been flowing through the element for some time. Measured heating element EMF can be used to correct for resistance measurement error caused by heating element EMF. The resistance measurement (skewed by Seebeck EMF) and the Seebeck EMF measurement together can be used to calculate accurate heating element resistances, which can be used to control average temperature of the heating element.

The effect of heating element EMF on the resistance measurement depends on the measurement circuit used. Heating element EMF will produce measurement error in all known resistance measurement circuits, so heating element EMF may be separately measured to correct for the error it causes in the resistance measurement. Sensitivity of the resistance measurement to heating element EMF may be understood so that measured heating element EMF can be used correctly to calculate heating element resistance from the two measurements taken. For example, the same differential op-amp used for the resistance measurement may also be used for the heating element EMF measurement. In the resistance measurement, the heating element may be powered through a voltage divider so that there is a measureable voltage across the heater which is compared against a reference voltage or summed with other reference voltages and amplified by the differential op amp circuit. For heating element EMF measurement, no voltage is applied to the heating element, which allows for direct measurement of the EMF, which is compared against another close reference voltage and amplified by the same differential op amp circuit used for the resistance measurement.

Because the same amplification circuit may be used, the sensitivities of both the resistance measurement and the heating element EMF measurement to heating element EMF will be the same. The two measurements may then be used to calculate accurate heating element resistances, the raw reading difference between measured heating element EMFs when the device is heating and when device has not been heating for some time (note that Seebeck EMF is 0 when heating element reaches thermal equilibrium in device) and may be subtracted from the raw resistance measurement reading before other calculations are performed to yield heating element resistance from corrected resistance measurement reading.

Figure 18:
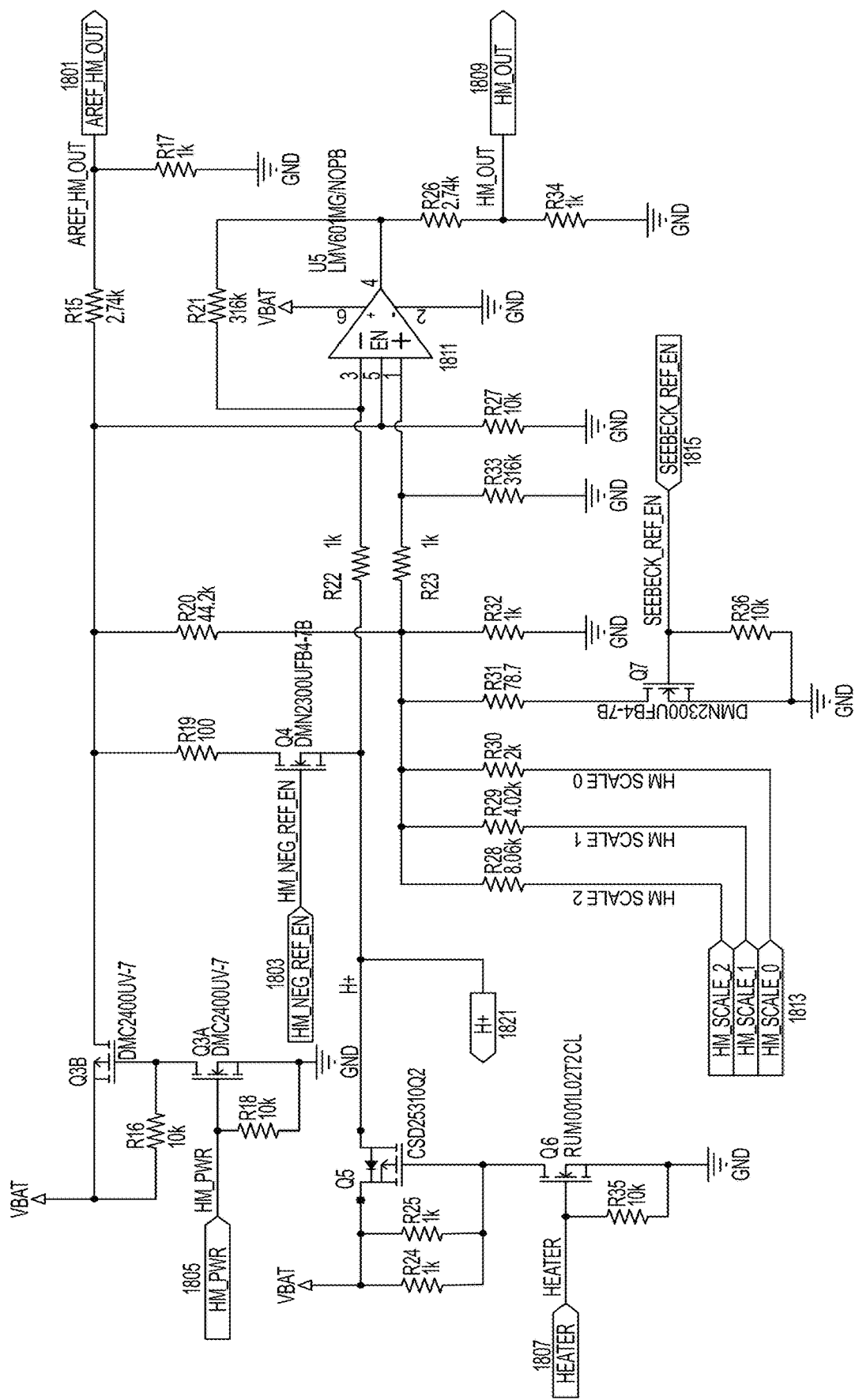
FIG. 18 is a Seebeck measurement circuit for a vaporizer apparatus correcting for the Seebeck effect, configured as a two-terminal sensing circuit.

FIG. 18 illustrates one example of a measurement circuit that may be used as part of a vaporization apparatus. Operation of this circuit to control heating element resistance while heating may be as follows (with signal and component names below referencing signals and components from schematic of FIG. 18); except for H+ 1821, all output boxes (1801, 1803, 1805, 1807, 1809, 1811, 1813) are connected to the microcontroller, which is not shown; timing noted below is for one exemplary software implementation and may be different or modified for different implementations). Heating element is connected between H+ 1821 and GND.

In FIG. 18, when device is heating, HEATER 1807 is driven with PWM to connect VBAT to H+ 1821 through Q5 (powering heating element with battery voltage) at some duty cycle to generate a known power in the heating element. When device is heating or in a wake state but not heating, every 3.9 ms (256 Hz measurement), HEATER 1807 is held off and HM_PWR 1805 is held on (powering differential op-amp circuit and voltage references required for measurements) for 268 μs so that either the heating element resistance or heating element EMF can be measured. Heating element resistance and EMF are each measured every 7.8 ms (each is measured during every other measurement window). The first 200 us of this 268 μs measurement window is settling time for the op-amp output as seen by microcontroller (HM_OUT 1809) to stabilize. ADC is performed by the microcontroller on HM_OUT 1809 between AREF_HM_OUT 1801 and GND during the last 68 μs of the measurement window. For the heating element resistance measurement, HM_NEG_REF_EN 1803 is on to bias the heating element so that the voltage divider formed by R19 and the heating element can compared by the differential op amp circuit (comprised of U5, R21, R22, R23, and R33) against a fixed voltage divider formed by R20 and R32, and some combination of R28, R29, and R30, which are used to keep HM_OUT 1809 in a usable voltage range between AREF_HM_OUT 1801 and GND for the range of heating element resistances that the device might see. HM_SCALE_0-2 1813 are either allowed to float (high impedance) or connected to GND within the microcontroller to use R28-30 to set the resistance measurement range of the circuit.

For the heating element EMF measurement, HM_NEG_REF_EN 1803 is off to allow H+ to float to a voltage that is the heating element EMF (relative GND) and SEEBECK_REF_EN 1815 is on to make the fixed reference used by the differential op amp circuit close enough to heating element EMF that HM_OUT 1809 will be usable (will be between AREF_HM_OUT 1801 and GND) over the range of heating element EMFs expected when heating element is heated. Heating element EMF may be as high as +/−3 mV. The heating element EMF measurement circuit can measure between +/−5 mV. The measurement circuit yields a non-zero ADC value when device has not been heating for some time and EMF is 0; this value is used to "zero" the heating element EMF readings when used in resistance calculations. Resistance calculations are as follows:

> Heating Element Resistance=(resistance measurement ADC raw−(EMF measurement ADC raw−EMF measurement ADC zero))*resistance measurement sensitivity+resistance measurement offset Resistance measurement sensitivities and offsets may depend on the active resistance measurement scale (selected using HM_SCALE_0-2 1813) and may be solved for using circuit component values and then included in the device (e.g., in the firmware, hardware or software of the apparatus).

Baseline resistance (measured resistance when heating element has not been heated for some time) may be used to calculate a target resistance that corresponds to a target average heating element temperature based on the heating element's resistivity vs. temperature curve.

The resistance measurement circuit may be a two-terminal sensing circuit, as just discussed. In other variations, a four-terminal sensing may be used to mitigate effects of variable contact resistance and trace or lead resistance in series with the heating element resistance measurement. Changing contact resistance and trace/lead resistance have a negligible impact on resistance measurement and temperature control, but these effects may be more pronounced in variations which have a lower resistance heating element and different heating element and device assembly. In this case, a four-terminal (also known as four-point) resistance and EMF measurement circuit, such as the one shown in FIG. 19, may be used.

Figure 19:
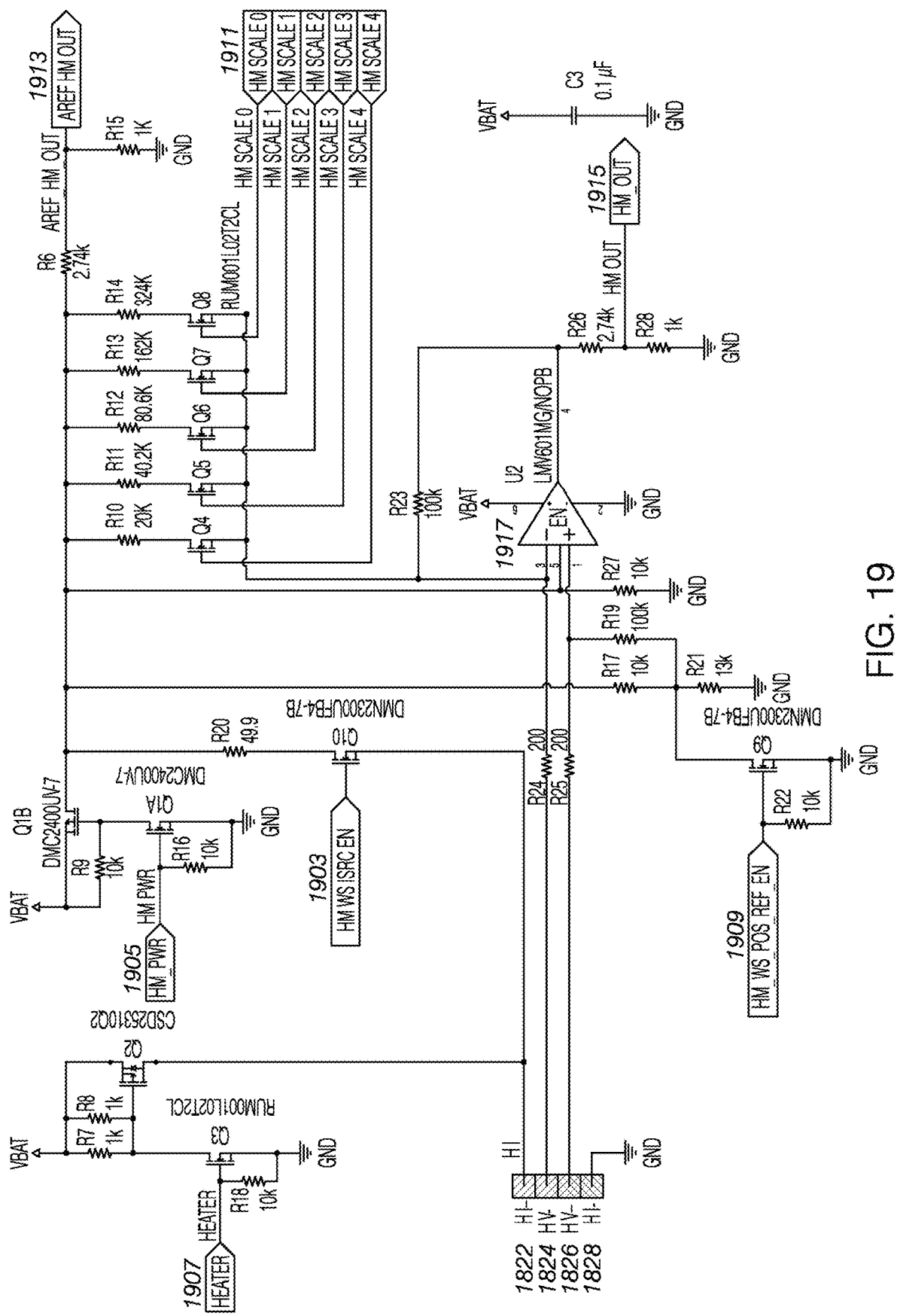
FIG. 19 is another example of a Seebeck measurement circuit for a vaporizer apparatus, configured as a four-terminal (four-point) circuit.

Operation of the circuit shown in FIG. 19 to control heating element resistance while heating may be done as follows (with signal and component names below referencing signals and components from schematic above; signals 1903, 1905, 1907, 1909, 1911, 1913, 1915, 1917) are connected to the microcontroller, which is not shown; timing noted below is exemplary only, and may be different). In FIG. 19, HI+ 1822 and HV+ 1826 connect directly to one terminal of the heating element, while HV− 1828 and HI− 1824 connect directly to the other terminal of the heating element.

When device is heating, HEATER 1907 is driven with PWM to connect VBAT to H+ 1822 through Q2 (powering heating element with battery voltage) at some duty cycle to generate a known power in the heating element.

When device is heating or in a wake state but not heating, every 3.9 ms (256 Hz measurement), HEATER 197 is held off and HM_PWR 1905 is held on (powering the differential summing op-amp circuit and voltage references required for measurements) for 268 μs so that either the heating element resistance or heating element EMF can be measured. Heating element resistance and EMF are each measured every 7.8 ms (each is measured during every other measurement window). The first 200 μs of this 268 μs measurement window is settling time for the op-amp output as seen by microcontroller (HM_OUT 1915) to stabilize. ADC is performed by the microcontroller on HM_OUT 1915 between AREF_HM_OUT 1913 and GND during the last 68 μs of the measurement window.

For the heating element resistance measurement, HM_WS_ISRC_EN 1903 is on to bias the heating element through R20 and HI+/− terminals so that the voltage across HV+/− can measured by the differential summing op amp circuit (comprised of U2, R19, R23-25, and optionally R10-14, R17, and R21). HM_WS_POS_REF_EN 1903 is on to sum GND through R19 with HV+ through R25. Some combination of HM_SCALE_0-5 are on to sum HV− through R24 with VBAT through some respective combination of R10-14 to keep HM_OUT 1915 in a usable voltage range between AREF_HM_OUT 1913 and GND for the range of heating element resistances that the device might see.

For the heating element EMF measurement, HM_WS_ISRC_EN 1903 is off to allow HV+ to float to a voltage that is the heating element EMF (relative HV−), HM_WS_POS_REF_EN 1909 is off to sum the R17, R21, R19 voltage divider through R19 with HV+ through R25, and HM_SCALE0-4 1911 are all off to provide no summing and only negative feedback at the negative input of the op-amp. This differential summing configuration keeps HM_OUT 1915 in a usable range (will be between AREF_HM_OUT 1913 and GND) over the range of heating element EMFs expected when heating element is heated. With the values shown above, the heating element EMF measurement circuit can measure between +/−3.5 mV. The measurement circuit yields a non-zero ADC value when device has not been heating for some time and EMF is 0; this value is used to "zero" the heating element EMF readings when used in resistance calculations.

Resistance calculations are as follows:

> Heating Element Resistance=(resistance measurement ADC raw−(EMF measurement ADC raw−EMF measurement ADC zero))*resistance measurement sensitivity+resistance measurement offset Resistance measurement sensitivities and offsets depend on the active resistance measurement scale (selected using HM_SCALE_0-4 1911) and may be solved for using circuit component values and then included in the device.

Baseline resistance (measured resistance when heating element has not been heated for some time) may be used to calculate a target resistance that corresponds to a target average heating element temperature based on the heating element's resistivity vs. temperature curve.

As described above, the mismatch in thermoelectric properties and the resulting EM (e.g., the Seebeck EMF) has been found by the inventors to be a potential source of resistance measurement error after data taken from controlled tests of vaporizer prototypes (e.g., using heating elements with extension leads). A single heating element run with temp control of the heating element (using measured heating element resistance without correction for this EMF) may consistently run with much higher power when connected in one polarity vs. the other polarity. It was discovered that asymmetries in the heating element (in this case the wick and coil) assembly could consistently produce hotter temperatures at one of the two heating element/extension lead junctions, resulting in consistent offset voltage at operating temperatures that skewed the resistance measurement in one direction with the heating element connected in one polarity and in the other direction with heating element connected in the other polarity. Although measured resistance was controlled during these tests, these devices were not accurately controlling heating element temperatures because measurements were skewed by this offset EMF resulting from the mismatch in thermoelectric properties of the components. With the correction described above, used to correct for the error in resistance measurement, it is observed that heating element polarity does not have an effect on the power required to hold the heating element at operating temperatures during controlled testing, which suggests that this correction yields accurate calculated heating element resistances that remove the effect of the offset EMF, providing much more accurate temperature control of the heating element than when not corrected.

Thus, in any of the variations described herein, the apparatus may include an offset correction circuit (also referred to as a Seebeck correction circuit) to correct for the offset voltage resulting from the mismatch in thermoelectric properties between the resistive heating coil and the conductive connectors linking the resistive heating coil to the power input (e.g., from the vaporizer base, including the vaporizer power controller) in the cartridge. The offset correction circuit may be located in the vaporizer base and connected between the coupling connectors 595, 595' to couple with the cartridge connectors and determine the offset voltage due to the mismatch in thermoelectric properties of the heating (resistive) coil and the wires linking the coil to the connector on the cartridge. Also described herein are methods of correcting for the mismatch (Seebeck effect) in thermoelectric properties between the coil and the wires (electrical extensions) connecting to the electrical connectors.

Dose Monitoring

As mentioned above, any of the apparatuses described herein may also or alternatively detect and display the dose of material applied. U.S. patent application Ser. No. 14/960, 259 (filed on Dec. 4, 2015, and published as US-2016-0157524-A1), herein incorporated by reference in its entirety, describes examples of methods for determining dose (and apparatuses including dose determination). Generally these methods may be used to accurately calculate dose based on the power applied to the heater and the temperature of the heater (or a material in contact with the heater) during an immediately before a small increment of time; total dose may be determined by summing these small increments up over a desired time range. These methods may be incorporated herein, and may be made even more accurate by correcting the power applied as described above (e.g., accounting for the offset EMF due to the Seebeck effect).

Alternatively or additionally, described herein are methods and apparatuses that may provide a rough approximation of dose based on the power applied over time to vaporize the material within the cartridge. This may be referred to herein as the consumption (of the vaporizable material in the cartridge, an indication of consumption) of the cartridge or vaporizable material, or the like. In general, the apparatus may aggregate the power during operation of the apparatus (e.g., the power applied over time during a puff/inhalation and/or the power applied over this time multiplied times the duration of the inhalation).

Figure 9E:
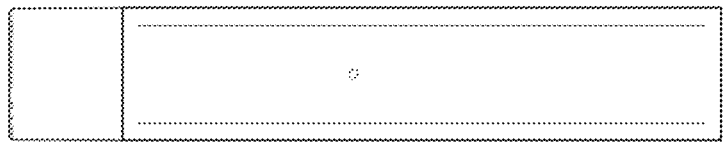
FIGS. 9A-9G show an assembled vaporizer apparatus including a vaporizer cartridge such as the one shown in FIGS. 7A-7F that has been fully seated and retained in a vaporizer base such as the one shown in FIGS. 8A-8G.
Figure 9D:
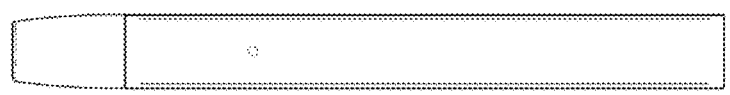
Figure 9C:
Figure 9G:
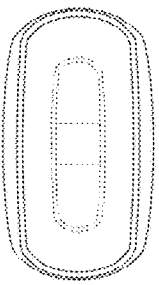
Figure 9F:
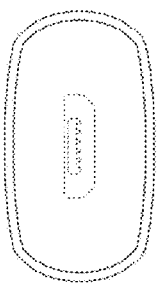
Figure 9A:
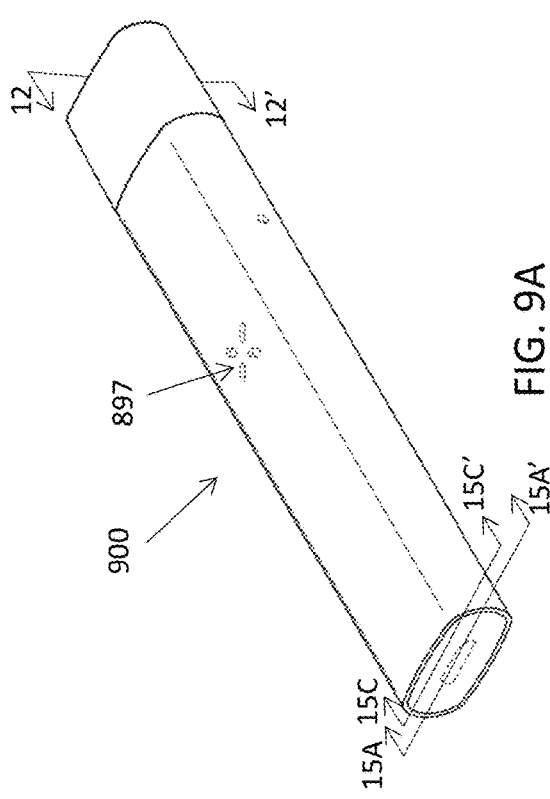
Figure 9B:
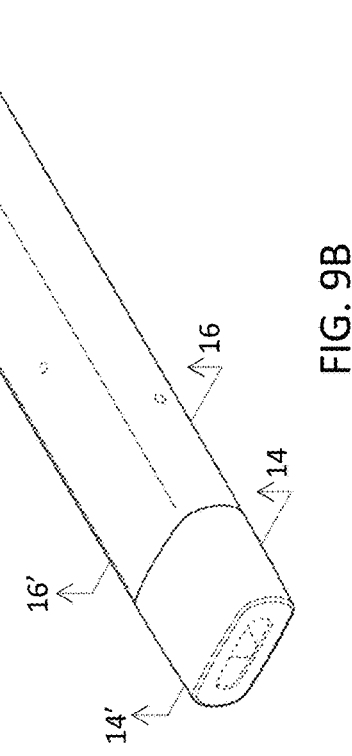

The apparatus may further provide an output of the amount of consumption. This output may be, in particular, a qualitative approximation. For example, the output may be incrementally increasing the number, intensity and/or color of one or more LEDs on the surface of the apparatus. For example, in this case, the consumption amount (dose) is not an absolute amount, but is an indicator or readout of the power applied to vaporize the material (power applied to the coils) over time. In FIG. 9C, for example, when the user first installs a cartridge and the apparatus is set up to display consumption/dose, the four LEDS 897 may initially be unlit or lit to the neutral color (e.g., white). As the user draws on the device and vaporizes the material within the cartridge, the number of LEDS illuminated may be increased and the intensity and/or color of illumination may be increased to indicate increasing dosage or consumption; for example the calculation of power applied over time may determine based on a number or predetermined increments, whether to increase the number of illuminated LEDS of a particular color and/or intensity, to change color and/or intensity, etc.

The accumulated dose may be reset manually (e.g., using an app, shaking the device, etc.) or by removing the cartridge. Alternatively or additionally to the qualitative output described above, a quantitative estimate based on the power may be displayed or output to a remote processor (e.g. smartphone, etc.).

Thermocouple as Heater

Figure 20A:
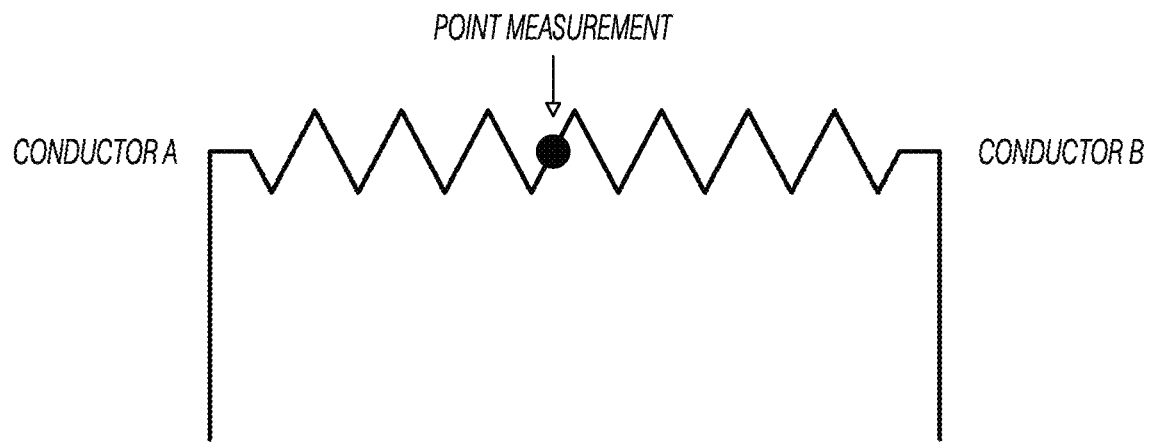
FIGS. 20A and 20B illustrate two examples of heating coils comprising different component conductors coupled to result in resistive heater from which a temperature measurement may be determined using a Seebeck sensing circuit as described herein.
Figure 20B:
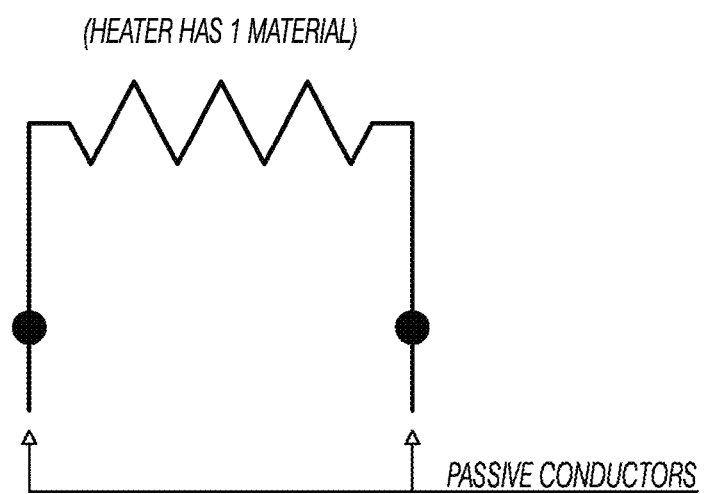

In any of the apparatuses described herein, the heater may be configured as a thermocouple junction. See, e.g., FIGS. 20A and 20B. Thus, a thermocouple junction (comprising materials having dissimilar thermoelectric properties) may be used to measure temperature at a point along the heater coil. As discussed above, this may allow an apparatus to resistively determine temperature along the heater coil using the thermoelectric properties described above. Thus, similar to what is described above, the heating element performs both as a heater and a temperature sensor. For example, a resistive heater may comprised of two dissimilar conductors (e.g., stainless steel and titanium) welded together, as shown in FIG. 20A. When the heater (heating coil) heats up, the dissimilar material will be heated differentially, resulting in a temperature gradient and a resulting offset voltage (EMF), due to the Seebeck effect discussed above, at the junction of the two dissimilar materials. This effect may be used to determine the temperature at that junction (whereas typically, we determine the average temperature of the entire heater by using TCR, temperature coefficient of resistance, as also discussed above.

The Seebeck effect also occurs at the junction between the heater end poles and passive electrical conduits. Although the correction circuits discussed above are aimed at correcting for the effect, it may also be possible to take advantage of the effect for a more localized temperature measurement. Compare, FIG. 20B to FIG. 20A, for example. In FIG. 20A, the junction is located in the middle of the heating element, and determining the offset voltage in this case, which is based on the temperature, may allow accurate temperature determination. This embodiment may be particularly relevant for a convection vaporizer, where you likely have a (relatively) large heater and you care about the temperature at just the air outlet end.

In vaporization systems where the heating element is connected to the device through extension leads, if Seebeck coefficients are known for both materials, the measured Seebeck EMF can be used to determine the net temperature gradient across the heating element. With some modeling, this measurement could be used to approximately control maximum heating element temperature instead of or in addition to average heating element temperature. This measurement can also be used to perform quality control where the heating element assembly is manufactured. In vaporization systems where the heating element is connected to the device through extension leads and the heating element is used to primarily heat air, if Seebeck coefficients are known for both materials, Seebeck EMF can be used to determine the net temperature gradient across the heating element, which with a known air flow path and thermal modeling of the system can be used to predict average air temperature at some point down-stream of the heating element. As mentioned above, this may be particularly advantageous in convection (hot-air) vaporization systems as two measurements (resistance and Seebeck EMF) taken from the actuator can allow for accurate temperature control of air flowing from the outlet of the heating element without additional sensors in the air path or connected to the heating element.

As shown in FIG. 20A, the Seebeck effect alone or the Seebeck effect in conjunction with resistance measurement can be used for temperature control of a heating element that has a material transition (junction) at the position where temperature is to be controlled. This is essentially creating a thermocouple out of resistive heating alloys so that the Seebeck EMF can be measured in order to control temperature at the hot junction of the thermocouple resistive heater. The junction could be positioned where the heating element is expected to be hottest to control maximum temperature of the heating element. The control algorithm could use a target average temperature of the heating element (calculated using resistance and EMF measurements) as well as a maximum acceptable max temperature of the heating element (calculated using just the EMF measurement). A device that knows both the average temperature of the heating element and the maximum temperature of the heating element could know more about the temperature gradient along the heating element and be better at predicting mass of material vaporized while heating than a device that only knows either maximum or average heating element temperature (device knowing precise mass of material vaporized is critical for dose-control in vaporizers). If extensions are used in such a system, they could be the same material as the intended heating element but much larger gauge for reduced losses in the extensions. Alternatively, extensions with Seebeck coefficients that are very similar to the Seebeck coefficients of the two heating element sections could be used so that Seebeck EMF is still usable for temp control of the hot junction (small contribution of heating element/extension junctions to net Seebeck EMF).

Vaporizers without Cartridges

Any of the features described herein may be incorporated into a vaporizer apparatus that does not require the uses of a separate (e.g., removable cartridge), including vaporizer apparatuses such as loose-leaf vaporizer apparatuses.

Such apparatuses are described, for example, in each of the following applications, herein incorporated by reference in their entirety: U.S. patent application Ser. No. 13/837,438, filed on Mar. 15, 2013, Publication No. US 2013-0312742 A1; U.S. patent application Ser. No. 15/166,001, filed on May 26, 2016, Publication No. US 2016-0262459 A1; U.S. patent application Ser. No. 14/581,666, filed on Dec. 23, 2014, Publication No. US 2015-0208729 A1; U.S. patent application Ser. No. 15/053,927, filed on Feb. 25, 2016, Publication No. US 2016-0174611 A1; U.S. patent application Ser. No. 15/257,748, filed on Sep. 6, 2016; U.S. patent application Ser. No. 15/257,760, filed on Sep. 6, 2016, Publication No. US 2016-0374399 A1; and U.S. patent application Ser. No. 15/257,768, filed on Sep. 6, 2016, Publication No. US 2016-0366947 A1.

For example such a device may include preset and allow the user to enter temp set mode by holding down on a button (on or under the mouthpiece) for >0.6 seconds. Pressing the button again cycles through the 4+1 presets. To exit temp set, again hold the button for >0.6 sec. The presets may be, e.g.,: 180 C, 193 C, 204 C, 216 C.

Any of the apparatuses described herein may include haptic feedback that may include distinct profiles for different events: For example:

⟋\—trapezoid—power on, and Bluetooth connect

‖—quick click—manual power off, and Bluetooth disconnect

⊓⊓—2 long clicks—temp reached

⊓—1 long click—entered low temp standby, and auto shutoff

Also the user may change the intensity of these envelopes via the app.

Although the disclosure, including the figures, described herein may described and/or exemplify these different variations separately, it should be understood that all or some, or components of them, may be combined.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge device comprising:
   a cartridge body extending in a distal to proximal axis and having a width and a diameter that are transverse to the distal to proximal axis, the cartridge body further having a proximal body end and a distal body end opposite the proximal body end along the distal to proximal axis;
   a reservoir formed within the cartridge body, the reservoir configured to contain a vaporizable material;
   a back piece forming a distal reservoir end of the reservoir and being sealed to the cartridge body from within the cartridge body;
   a mouthpiece at the proximal body end of the cartridge body;
   a bottom cover plate forming a distal end of the cartridge device, the bottom cover plate opposite the mouthpiece, the bottom cover plate comprising an external surface of the cartridge device, wherein an air chamber is formed between the back piece and the bottom cover plate;

an air flow path extending between the air chamber and the mouthpiece, the air flow path extending through the reservoir;

a heater within the air flow path;

a pair of electrical contacts in electrical communication with the heater; and one or more air openings on the external surface of the cartridge device, wherein the one or more air openings are fluidly connected with the air flow path.

2. The cartridge device of claim 1, wherein the pair of electrical contacts are positioned at the distal end of the cartridge device.

3. The cartridge device of claim 2, wherein the cartridge body comprises internal sidewalls, and wherein the air chamber is formed between the bottom cover plate and the internal sidewalls.

4. The cartridge device of claim 3, wherein the air chamber is enclosed within the distal body end of the cartridge body.

5. The cartridge device of claim 4, wherein the heater comprises a heating element and a wicking structure configured to draw the vaporizable material into the heater, and wherein the heater is configured to heat and cause vaporization of the vaporizable material into the air flow path to form an aerosol, and wherein the mouthpiece is configured to deliver the aerosol to a user.

6. The cartridge device of claim 5, further comprising a housing piece configured to form a vaporization chamber comprising at least a portion of the heater that is separated from the reservoir, and wherein the wicking structure is in fluid communication with the vaporizable material in the reservoir.

7. The cartridge device of claim 1, wherein the back piece is configured to be inserted into the distal body end of the cartridge body, and wherein the back piece is sealed to the cartridge body by one or more seals, wherein the one or more seals comprises an o-ring.

8. The cartridge device of claim 1, wherein the one or more air openings are formed through the bottom cover plate.

9. The cartridge device of claim 1, further comprising one or more absorbent pads within the air chamber, wherein the one or more absorbent pads are configured to capture deposited and/or condensed liquid without requiring air to pass through the one or more absorbent pads.

10. The cartridge device of claim 9, wherein the one or more absorbent pads are parallel with one another, wherein a gap is formed between the one or more absorbent pads, wherein the one or more absorbent pads extend off-axis relative to the air flow path, and wherein the one or more absorbent pads are positioned within the air chamber along the diameter, off-axis relative to the air flow path.

11. A vaporizer device comprising:

a cartridge device according to claim 1;

a vaporizer device body having a proximal device end and a distal device end, the proximal device end including an opening into a cartridge receiver region configured to insertably receive the cartridge device, wherein the vaporizer device body comprises a shell having air inlets configured to allow airflow into the cartridge receiver region, the air inlets formed through opposing sides of the shell, and the air inlets in fluid communication with the air flow path when the cartridge device is insertably received within the cartridge receiver region, and wherein the vaporizer device body comprises a pair of connectors configured to electrically communicate with the pair of electrical contacts of the cartridge device.

12. A vaporizer device comprising:

a cartridge comprising:

a reservoir configured to contain a vaporizable material;

a mouthpiece configured to deliver an aerosol comprising the vaporizable material to a user, the mouthpiece at a proximal end of the cartridge;

an air flow path having an air flow path axis;

an air inlet via which air from outside the cartridge enters the cartridge;

a heating element configured to heat and cause vaporization of the vaporizable material into air drawn into the cartridge along the air flow path, the air flow path connecting the air inlet and the mouthpiece, the air flow path passing proximate to the heating element; and an overflow leak chamber at a distal end of the cartridge, opposite the mouthpiece; and a vaporizer device body having a proximal device end and a distal device end, the proximal device end including an opening into a cartridge receiver region configured to insertably receive the cartridge.

13. The vaporizer device of claim 12, wherein the cartridge further comprises a pair of electrical contacts on the distal end of the cartridge, the pair of electrical contacts in electrical communication with the heating element, and wherein the vaporizer device body further comprises a pair of connectors configured to electrically communicate with the pair of electrical contacts.

14. The vaporizer device of claim 13, wherein the cartridge further comprises sidewalls and a bottom cover plate, wherein the overflow leak chamber is formed between the sidewalls and the bottom cover plate.

15. The vaporizer device of claim 14, wherein the cartridge further comprises a back piece, wherein the bottom cover plate forms a distal end of the cartridge, the bottom cover plate opposite the mouthpiece, and wherein the overflow leak chamber is formed between the back piece and the bottom cover plate.

16. The vaporizer device of claim 15, wherein the reservoir is configured to contain a vaporizable material within an internal volume of the reservoir, the internal volume being at least partially defined by the vaporizer device body and a proximal portion of the back piece.

17. The vaporizer device of claim 14, wherein the bottom cover plate comprises an external surface of the cartridge, and wherein the bottom cover plate further comprises one or more air openings fluidly connected with the air flow path.

18. The vaporizer device of claim 12, wherein the air flow path extends between the overflow leak chamber and the mouthpiece, wherein the cartridge further comprises an air tube extending through the reservoir, and wherein the air flow path extends through the air tube.

19. The vaporizer device of claim 12, wherein the overflow leak chamber is enclosed within the distal end of the cartridge.

20. The vaporizer device of claim 12, wherein the cartridge further comprises one or more absorbent pads within the overflow leak chamber and off-axis from the air flow path axis, wherein the one or more absorbent pads are configured to capture deposited and/or condensed liquid without requiring air to pass through the one or more absorbent pads, wherein the one or more absorbent pads is biased against a respective sidewall of the cartridge.

* * * * *